United States Patent
Achinivu et al.

(10) Patent No.: US 11,884,620 B2
(45) Date of Patent: Jan. 30, 2024

(54) USE OF POLYAMINES IN THE PRETREATMENT OF BIOMASS

(71) Applicants: THE REGENTS OF THE UNIVERSITY OF CALIFORNIA, Oakland, CA (US); NATIONAL TECHNOLOGY AND ENGINEERING SOLUTIONS OF SANDIA, LLC, Albuquerque, NM (US)

(72) Inventors: Ezinne Achinivu, Alexandria, VA (US); Mood Mohan, Emeryville, CA (US); Hemant Choudhary, Emeryville, CA (US); Lalitendu Das, Emeryville, CA (US); Venkataramana R. Pidatala, Emeryville, CA (US); Harsha D. Magurudeniya, Newport News, VA (US); Kaixuan Huang, Albany, CA (US); John M. Gladden, Alameda, CA (US); Blake A. Simmons, San Francisco, CA (US)

(73) Assignees: THE REGENTS OF THE UNIVERSITY OF CALIFORNIA, Oakland, CA (US); NATIONAL TECHNOLOGY & ENGINEERING SOLUTIONS OF SANDIA, LLC, Albuquerque, NM (US)

( * ) Notice: Subject to any disclaimer, the term of this patent is extended or adjusted under 35 U.S.C. 154(b) by 0 days.

(21) Appl. No.: 17/547,134

(22) Filed: Dec. 9, 2021

(65) Prior Publication Data
US 2022/0194877 A1 Jun. 23, 2022

Related U.S. Application Data

(60) Provisional application No. 63/124,660, filed on Dec. 11, 2020.

(51) Int. Cl.
*C07C 7/08* (2006.01)

(52) U.S. Cl.
CPC ..................... *C07C 7/08* (2013.01)

(58) Field of Classification Search
CPC ... C07C 7/08; C07G 1/00; C12P 19/02; C12P 19/14; C12P 2201/00
See application file for complete search history.

(56) References Cited

U.S. PATENT DOCUMENTS

| 6,177,575 B1 | 1/2001 | Arduengo, III et al. |
| 7,985,567 B2 | 7/2011 | Chou et al. |

(Continued)

FOREIGN PATENT DOCUMENTS

| WO | 2009/006386 A2 | 1/2009 |
| WO | 2009/006429 A1 | 1/2009 |

(Continued)

OTHER PUBLICATIONS

Galbe et al., "Pretreatment for biorefneries: a review of common methods for efcient utilisation of lignocellulosic materials", Biotechnol Biofuels, 12, 294 (2019), 26 pages.

(Continued)

*Primary Examiner* — Ellen M McAvoy
*Assistant Examiner* — Chantel Graham
(74) *Attorney, Agent, or Firm* — Robin C. Chiang; LAWRENCE BERKELEY NATIONAL LABORATORY

(57) ABSTRACT

The present invention provides for a method to deconstruct a biomass: the method comprising: (a) introducing a solvent comprising a polyamine, or a mixture of polyamines, to a biomass to dissolve at least part of solid biomass in the solvent, wherein the polyamine is a Brønsted or Lewis base, and/or the polyamine is a hydrogen bond donor and/or acceptor; (b) optionally introducing an enzyme and/or a microbe to the solubilized biomass mixture such that the (Continued)

enzyme and/or microbe produces a sugar from the solubilized biomass mixture; (c) optionally separating the sugar from the solubilized biomass mixture; and (d) optionally separating the lignan from the solubilized biomass mixture.

5 Claims, 32 Drawing Sheets

(56) References Cited

U.S. PATENT DOCUMENTS

| | | | |
|---|---|---|---|
| 8,420,833 B2 | 4/2013 | Katz et al. | |
| 8,852,902 B2 | 10/2014 | Katz et al. | |
| 9,109,175 B2 | 8/2015 | Lee et al. | |
| 9,200,298 B2 | 12/2015 | Lee et al. | |
| 9,322,042 B2 | 4/2016 | Sapra et al. | |
| 9,334,514 B2 | 5/2016 | Fortman et al. | |
| 9,376,691 B2 | 6/2016 | Peralta-Yahya et al. | |
| 9,376,728 B2 | 6/2016 | Zhang et al. | |
| 9,382,553 B2 | 7/2016 | Kirby et al. | |
| 9,624,482 B2 | 4/2017 | Sapra et al. | |
| 9,631,210 B2 | 4/2017 | Chou et al. | |
| 9,725,749 B2 | 8/2017 | Chen et al. | |
| 9,765,044 B2 | 9/2017 | Socha et al. | |
| 9,803,182 B2 | 10/2017 | Gladden et al. | |
| 9,862,982 B2 | 1/2018 | Zhang et al. | |
| 9,951,345 B2 | 4/2018 | Steen et al. | |
| 10,155,735 B2 | 12/2018 | Socha et al. | |
| 10,167,488 B2 | 1/2019 | Keasling et al. | |
| 2004/0097755 A1 | 5/2004 | Abbott et al. | |
| 2010/0196967 A1 | 8/2010 | Edye et al. | |
| 2015/0094459 A1* | 4/2015 | Kroon | D21C 3/003 530/507 |
| 2021/0317481 A1* | 10/2021 | Das | C12P 7/10 |

FOREIGN PATENT DOCUMENTS

| | | |
|---|---|---|
| WO | 2009/006430 A1 | 1/2009 |
| WO | 2009/134899 A2 | 12/2009 |
| WO | 2010/124266 A2 | 10/2010 |
| WO | 2010/127318 A2 | 11/2010 |
| WO | 2012/050931 A2 | 4/2012 |
| WO | 2012/058686 A2 | 5/2012 |
| WO | 2012/064740 A1 | 5/2012 |
| WO | 2012/071439 A1 | 5/2012 |
| WO | 2012/135389 A2 | 10/2012 |
| WO | 2012/151214 A1 | 11/2012 |
| WO | 2014/093402 A2 | 6/2014 |
| WO | 2015/013674 A2 | 1/2015 |
| WO | 2016/070125 A1 | 5/2016 |
| WO | 2016/105538 A1 | 6/2016 |
| WO | 2017/087982 A2 | 5/2017 |
| WO | 2017/091781 A1 | 6/2017 |
| WO | 2017/214159 A1 | 12/2017 |
| WO | 2017/214332 A1 | 12/2017 |
| WO | 2018/200888 A1 | 1/2018 |
| WO | 2018/119152 A1 | 6/2018 |
| WO | 2019/050990 A1 | 3/2019 |

OTHER PUBLICATIONS

Chang, "Harnessing energy from plant biomass" Curr. Opin. Chem. Biol., 11, 677-684 (2007).
Rodionova et al., "Biofuel production: Challenges and opportunities" Int. J. Hydrogen Energy, 42, 8450-8461 (2017).
Achinivu et al., "Lignin extraction from biomass with protic ionic liquids", Green Chem., 16, 1114-1119 (2014).
Upton et al., "Strategies for the Conversion of Lignin to High-Value Polymeric Materials: Review and Perspective" Chem. Rev., 116, 2275-2306 (2016).
Kumar et al., "Methods for Pretreatment of Lignocellulosic Biomass for Efficient Hydrolysis and Biofuel Production" Ind Eng Chem Res, 48, 3713-3729 (2009).
Kautto et al., "Economic analysis of an organosolv process for bioethanol production" BioRes, 9, 6041-6072 (2014).
Zhang et al., "Organosolv Pretreatment of Plant Biomass for Enhanced Enzymatic Saccharification " Green Chem., 18, 360-381 (2016).
Borand et al., "Effects of organosolv pretreatment conditions for lignocellulosic biomass in biorefinery applications: A review" J. Renewable Sustainable Energy, 10, 033104 (2018).
Zhao et al., "Evaluation of the mass transfer effects on delignification kinetics of atmospheric acetic acid fractionation of sugarcane bagasse with a shrinking-layer model" Biofuels, Bioprod. Bioref., 11, 567-590 (2017).
Chen et al. "Distillable Ionic Liquids: reversible Amide O Alkylation", Angewandte Comm. 52:13392-13396 (2013).
King et al. "Distillable Acid-Base Conjugate Ionic Liquids for Cellulose Dissolution and Processing", Angewandte Comm. 50:6301-6305 (2011).
Vijayaraghavan et al. "CO2-based Alkyl Carbamate Ionic Liquids as Distillable Extraction Solvents", ACS Sustainable Chem. Engin. 2:31724-1728 (2014).
Idris et al. "Distillable Protic Ionic Liquids for Keratin Dissolution and Recovery", ACS Sustainable Chem. Engin. 2:1888-1894 (2014).
Chen et al., "A comparison of several organosolv pretreatments for improving the enzymatic hydrolysis of wheat straw: Substrate digestibility, fermentability and structural features" Appl. Energy, 150, 224-232 (2015).
Cheng et al., "Using Solubility Parameter Analysis to Understand Delignification of Poplar and Rice Straw with Catalyzed Organosolv Fractionation Processes" BioRes, 14, 486-499 (2019).
Zhao et al., "Organosolv pretreatment of lignocellulosic biomass for enzymatic hydrolysis" Appl. Microbiol. Biotechnol., 82, 815-827 (2009).
Qin et al., "Optimization of ethylenediamine pretreatment and enzymatic hydrolysis to produce fermentable sugars from corn stover" Ind. Crops Prod., 102, 51-57 (2017).
Cheng et al., "Lignocellulosic biomass delignification using aqueous alcohol solutions with the catalysis of acidic ionic liquids: A comparison study of solvents" Bioresour. Technol., 249, 969-975 (2018).
Sun et al. "One-pot integrated biofuel production using low-cost biocompatible protic ionic liquids", Green Chem. 19 (13):3152-3163 (2017)☐.
Ye et al., "Application of solubility parameter theory to organosolv extraction of lignin from enzymatically hydrolyzed cornstalks" Bioresources, 9, 3417-3427 (2014).
Quesada-Medina et al., "Organosolv extraction of lignin from hydrolyzed almond shells and application of the d-value theory" Bioresour. Technol., 101, 8252-8260 (2010).
Soh et al., "Green Solvents in Biomass Processing" ACS Sustain. Chem. Eng., 4, 5821-5837 (2016).
Kwok et al., "Pretreatment Efficacy and Lignin Solubility of Organic Solvents on Juvenile Slash Pine Chips for Lignin Value Prior to Pulping" Bommarius, BioRes, 14, 5988-6003 (2019).
Novo et al., "Hansen Solubility Parameters: A Tool for Solvent Selection for Organosolv Delignification" Ind Eng Chem Res, 58, 14520-14527 (2019).
Balaji et al., "COSMO-RS Based Predictions for the Extraction of Lignin from Lignocellulosic Biomass Using Ionic Liquids: Effect of Cation and Anion Combination" J. Solution Chem., 41, 1610-1630 (2012).
Casas et al., "Comparison of lignin and cellulose solubilities in ionic liquids by COSMO-RS analysis and experimental validation" Ind. Crops Prod., 37, 155-163 (2012).
Casas et al., "Relation between differential solubility of cellulose and lignin in ionic liquids and activity coefficients" RSC advances, 3, 3453-3460 (2012).
Zhang et al., "Genomic and phenotypic diversity of carbapenemase-producing enterobacteriaceae isolates from bacteremia in china: A multicenter epidemiological, microbiological, and genetic study" ACS Sustain. Chem. Eng., 7, 8678-8686 (2019).
Zhang et al., "A DFT study on lignin dissolution in imidazolium-based ionic liquids", Rsc Advances, 7, 12670-12681 (2017).
Ji et al., "Mechanism of Lignin Dissolution and Regeneration in Ionic Liquid" Energy Fuels, 26, 6393-6403 (2012).

(56) References Cited

OTHER PUBLICATIONS

Thielemans et al.,"Lignin Esters for Use in Unsaturated Thermosets: Lignin Modification and Solubility Modeling" and R. P. Wool, Biomacromolecules, 6, 1895-1905 (2005).
Hoy, "Solubility Parameter as a Design Parameter for Water Borne Polymers and Coatings" Journal of Coated Fabrics, 19, 53-67 (1989).
Mohan et al., "Multiscale modelling strategies and experimental insights for the solvation of cellulose and hemicellulose in ionic liquids" Mol. Phys., 116, 1-21 (2018).
Kahlen et al., "Modelling cellulose solubilities in ionic liquids using COSMO-RS" Green Chemistry, 12, 2172-2181 (2010).
Liu et al., "Predictive screening of ionic liquids for dissolving cellulose and experimental verification" Green Chemistry, 18, 6246-6254 (2016).
Liu et al., "Enhanced Enzymatic Hydrolysis and Lignin Extraction of Wheat Straw by Triethylbenzyl Ammonium Chloride/Lactic Acid-Based Deep Eutectic Solvent Pretreatment", ACS Omega, 4, 19829-19839 (2019).
Song et al.,"Effect of Liquid Viscosity on the Liquid Phase Mass Transfer Coefficient of Packing" Energy Procedia, 63, 1268-1286 (2014).
Song et al., "Effect of Liquid Viscosity on Mass Transfer Area and Liquid Film Mass Transfer Coefficient for GT-OPTIMPAK 250Y" Energy Procedia, 114, 2713-2727 (2017).
Zhao et al., "Evaluation of the mass transfer effects on delignification kinetics of atmospheric acetic acid fractionation of sugarcane bagasse with a shrinkinglayer model" Bioresour. Technol., 261, 52-61 (2018).
Simão et al., "Heterogeneous studies in pulping of wood: Modelling mass transfer of dissolved lignin", Chemical Engineering Journal, 170, 264-269 (2011).
Hartono et al., "Density, viscosity, and excess properties of aqueous solution of diethylenetriamine (DETA)" The Journal of Chemical Thermodynamics, 41, 973-979 (2009).
Padmanabhan et al., "Delignification of miscanthus using ethylenediamine (EDA) with or without ammonia and subsequent enzymatic hydrolysis to sugars", 3 Biotech, 6, 23 (2016), 10 pages.
Popelier, "Characterization of a Dihydrogen Bond on the Basis of the Electron Density", J. Phys. Chem. A, 102, 1873-1878 (1998).
Hanwell et al., "Avogadro: an advanced semantic chemical editor, visualization, and analysis platform" J. Cheminform., 2012, 4, 17 (2012), 17 pages.
Mohan et al., "Solid Liquid Equilibrium of Cellobiose, Sucrose, and Maltose Monohydrate in Ionic Liquids: Experimental and Quantum Chemical Insights" Journal of Chemical & Engineering Data, 61, 2923-2932 (2016).
Gonzalez-Miquel et al., "Excess Enthalpy of Monoethanolamine + Ionic Liquid Mixtures: How Good are COSMO-RS Predictions?" J. Phys. Chem. B, 118, 11512-11522 (2014).
Mohan et al., "Solubility of glucose, xylose, fructose and galactose in ionic liquids: Experimental and theoretical studies using a continuum solvation model", Fluid Phase Equilib., 395, 33-43 (2015).
Anantharaj et al., "COSMO-RS-Based Screening of Ionic Liquids as Green Solvents in Denitrification Studies" Ind Eng Chem Res, 49, 8705-8725 (2010).
Li et al., "Effects of thermal pretreatment on acidification phase during two-phase batch anaerobic digestion of kitchen waste" Renew. Energy, 77, 550-557 (2015).
Eckert et al., "Fast Solvent Screening via Quantum Chemistry: COSMO-RS Approach" AIChE Journal, 2002, 48, 369-385 (2002).
Kurnia et al., "Evaluation of the Conductor-like Screening Model for Real Solvents for the Prediction of the Water Activity Coefficient at Infinite Dilution in Ionic Liquids" Ind Eng Chem Res, 53, 12466-12475 (2014).
Grimme et al.,"Effect of the damping function in dispersion corrected density functional theory", J. Comput. Chem., 32, 1456-1465 (2011).
Ding e al., "Theoretical and experimental investigation on dissolution and regeneration of cellulose in ionic liquid" Carbohydr. Polym., 89, 7-16 (2012).
Mohan et al., "Solubility of glucose in tetrabutylammonium bromide based deep eutectic solvents: Experimental and molecular dynamic simulations" Fluid Phase Equilibria, 448, 168-177 (2017).
Guo et al., "Probing anion-cellulose interactions in imidazolium-based room temperature ionic liquids: a density functional study" Carbohydr. Res., 345, 2201-2205 (2010).
Espinosa et al., "Hydrogen bond strengths revealed by topological analyses of experimentally observed electron densities" Chem. Phys. Lett., 285, 170-173 (1998).
Lu et al., "Multiwfn: A Multifunctional Wavefunction Analyze" J. Comput. Chem., 33, 580-592 (2012).
Humphrey et al., "VMD: Visual molecular dynamics", J Mol Graph, 14, 33-8, 27 (1996).
Loschen et al., "COSMOquick: A Novel Interface for Fast σ-Profile Composition and Its Application to COSMO-RS Solvent Screening Using Multiple Reference Solvents" Ind Eng Chem Res, 51, 14303-14308 (2012).
Niederquell et al., "New prediction methods for solubility parameters based on molecular sigma profiles using pharmaceutical materials" Int. J. Pharm., 546, 137-144 (2018).
Yu et al.,"Selective Separation of Wood Components Based on Hansen's Theory of Solubility" Ind Eng Chem Res, 50, 7513-7519 (2011).
Yao et al.,"Insights of Ethanol Organosolv Pretreatment on Lignin Properties of Broussonetia papyrifera" ACS Sustain. Chem. Eng., 6, 14767-14773 (2018).
Sluiter et al., "Determination of Structural Carbohydrates and Lignin in Biomass" NREL, TP-510-42618 (2008).
Greaves et al. "Protic Ionic Liquids: Properties and Applications" Chem. Rev. 108(1):206-237 (2008).
Vanholme et al., "Lignin Biosynthesis and Structure", Plant Physiol., 153, 895-905 (2010).

* cited by examiner

Pretreament Solvents (a) −133.37 kJ/mol
(b) −122.45 kJ/mol
(c) −114.94 kJ/mol
(d) −90.26 kJ/mol
(e) −60.58 kJ/mol (a)

(b)

(a) 1,5-diaminopentane (b) Diethylenetriamine (c) 1,3-diaminopropane (d) 2,2-dimethyl-1,3-propanediamine (e) 2-ethoxyethanol (f) benzyl alcohol (a) Lignin-2-ethoxy ethanol-1
E = -1420.50316587

(b) Lignin-2-ethoxy ethanol-2
E = -1420.5006484

(c) Lignin-2-ethoxy ethanol-3
E = -1420.49843929

(d) Lignin-2-ethoxy ethanol-4
E = -1420.49841527

(e) Lignin-2-ethoxy ethanol-5
E = -1420.49726424

(f) Lignin-2-ethoxy ethanol-6
E = -1420.4965459

(g) Lignin-2-ethoxyethanol-7
E = -1420.49530012

(a) Lignin-furfuryl alcohol-1
E = -1456.19460258

(b) Lignin-furfuryl alcohol-2
E = -1456.19115991

(c) Lignin-furfuryl alcohol-3
E = -1456.18603716

(d) Lignin-furfuryl alcohol-4
E = -1456.18559915

(e) Lignin-furfuryl alcohol-5
E = -1456.18031223

(f) Lignin-furfuryl alcohol-6
E = -1456.17917738

(g) Lignin-furfuryl alcohol-7
E = -1456.17756777

(a) Lignin-isobutyl acetate -1
E = -1497.98931539

(b) Lignin-isobutyl acetate -2
E = -1497.98696768

(c) Lignin-isobutyl acetate -3
E = -1497.98696767

(d) Lignin-isobutyl acetate -4
E = -1497.98661456

(e) Lignin-isobutyl acetate -5
E = -1497.98661456

(f) Lignin-isobutyl acetate -6
E = -1497.98247558

USE OF POLYAMINES IN THE PRETREATMENT OF BIOMASS

CROSS-REFERENCE TO RELATED APPLICATIONS

This application claims priority to U.S. Provisional Patent Application Ser. No. 63/124,660, filed Dec. 11, 2020, which is hereby incorporated by reference.

STATEMENT OF GOVERNMENTAL SUPPORT

The invention was made with government support under Contract Nos. DE-AC02-05CH11231 awarded by the U.S. Department of Energy. The government has certain rights in the invention.

THE NAMES OF THE PARTIES TO A JOINT RESEARCH AGREEMENT

The present claimed invention was generated through a joint research agreement which The Regents of the University of California and Sandia National Laboratories are party to.

FIELD OF THE INVENTION

The present invention is in the field of biomass pretreatment.

BACKGROUND OF THE INVENTION

Lignocellulosic biomass is one of the primary natural resources that can be utilized as a renewable source of key intermediates to produce bioenergy, chemicals, and biomaterials.[1,2] However, the distinctive physical and chemical diversity of its major constituents (cellulose, hemicellulose, and lignin), along with its complex microstructure and chemical linkages make it difficult to be effectively processed or fractionated into its various constituents. This key hurdle must be overcome for the development of sustainable biorefineries and a robust bio-based economy.[1,3] To effectively accomplish this, the cross-linked matrix of lignin and hemicelluloses that surrounds the cellulose fibers must be disrupted.[4] In particular, the extraction of lignin, the component that predominantly makes the biomass recalcitrant to deconstruction, is necessary to enable the efficient conversion of lignocellulosic intermediates into valuable products (fuels and/or chemicals).[1,4-7]

There are several different pretreatment strategies that have been investigated for the separation of pure lignin and amongst them four chemical industrial processes are noteworthy: sulfite, kraft, soda and organosolv pretreatments.[6,8] Out of these methods, the organosolv fractionation process has been widely accepted as one of the most promising techniques for biomass fractionation due to its comparatively low environmental impact, high delignification efficiency, and the diversity of products that are released.[1,9,10] Organosolv pulping or fractionation is one of the methods of biomass fractionation that can produce high-quality cellulose biofuels (via momoreic sugar precursors), along with a high purity lignin. Unlike other pretreatment methods, the organosolv process is sulfur free, thereby, resulting in products with a high level of purity, structure of the resulting fragments, and molecular weight of the isolated degraded lignin. Additionally, this approach is particularly appealing because of the possibility of recovery and recycling of the organic solvent.[11-13] In a typical organosolv process, an organic solvent is used to pretreat lignocellulosic biomass with or without the addition of external catalysts.[12,13] Organic solvents such as short alkyl chain aliphatic alcohols (e.g., methanol, ethanol), polyols (e.g., glycerol, ethylene glycol, triethylene glycol), amines, alkanolamines, organic acids, acetone, dioxanes, and phenols have been widely used for the organosolv process.[11,14] In most cases, the biomass pretreated by organic solvents is very susceptible to hydrolysis (via enzymes) and can be readily deconstructed to yield monomeric sugars.[11,13,15] Cheng et al. studied the ability of 12 organic solvents including alcohols, alcohol ethers, lactones, and alkanolamines, to fractionate poplar and rice straw and reported at least 70% delignification.[16] Zhai et al. also reported >90% conversion of the polysaccharides (cellulose/hemicelluloses) for alcohol-pretreated biomasses,[17] and, Qin et al. reported that ethylenediamine can be applied to corn stover, resulting in glucose and xylose yields of 92% and 70% respectively after enzymatic digestion.[18]

Despite the promise for the organosolv processes, the near limitless possibilities for solvent selection has not been fully explored within the context of a robust multi-product biorefinery. Solvents like alcohols and diols have dominated the organosolv literature,[9,14,19] yet many other possible solvents may exist with better performance and/or recyclability. The identification of these solvents would be greatly accelerated by the development of a computational toolset that could predict lignin solubilization and be systematic and efficient. Nevertheless, researchers still require guidelines to be established for the choice of successful solvent systems to become methodical. These guidelines or design rules should offer insights into the key chemical functionalities within a solvent that promote lignin dissolution, as well as the structural and conformational variations within a solvent group that can affect it. Lastly, it would be ideal if this toolset could aid in revealing the mechanistic factors that control lignin dissolution, which would help further refine the design/development of new and effective solvent systems for lignin.

Alongside experimental studies, molecular simulations have also been employed to understand the dissolution mechanism of biomass and its components. Researchers have adopted quantum chemical (QC) and molecular dynamics (MD) simulations, which provide fundamental insights of the molecular systems (e.g. lignin and ionic liquids). Solubility parameters such as Hildebrand[20-22] and Hansen solubility parameters (HSP)[16,23-26] and the COSMO-RS (COnductor like Screening MOdel for Real Solvents) model have been widely used to design and develop effective solvents for biomass delignification.[27-30] Balaji et al.[27] and Casas et al.[28,29] screened various ionic liquids (ILs) to understand the lignin dissolution ability by predicting Hildebrand solubility parameters and thermodynamic parameters namely excess enthalpy and activity coefficient using COSMO-RS. Casas reported that the strong exothermic behavior of excess enthalpy and lower activity coefficients are beneficial for higher lignin dissolution.[28,29] However, in both studies, only lignin's monomeric structures were employed as a model component. Later, Zhang et al.[31] and Ji et al.[32] performed quantum chemical (density functional theory) simulations to reveal the mechanism of lignin dissolution in imidazolium-based ionic liquids. It has been reported that the stronger H-bonding interaction between lignin and IL is responsible for the greater ability to dissolve lignin. These molecular simulation techniques can help in identifying new potential effective solvents for biomass pretreatment. However, the dissolution mechanism of lignin from lignocellulosic biomass using molecular solvents and the development of a predictive model for lignin removal has not yet been fully addressed. There is still a need to develop a predictive model for lignin removal, which can describe the solubility, while exploring the relationship between lignin dissolution and pretreatment effectiveness.

SUMMARY OF THE INVENTION

The present invention provides for a method to deconstruct a biomass: the method comprising: (a) introducing a solvent comprising a polyamine, or a mixture of polyamines, to a biomass to dissolve at least part of solid biomass in the solvent, wherein the polyamine is a Brønsted or Lewis base, and/or the polyamine is a hydrogen bond donor and/or acceptor; (b) optionally introducing an enzyme and/or a microbe to the solubilized biomass mixture such that the enzyme and/or microbe produces a sugar from the solubilized biomass mixture; (c) optionally separating the sugar from the solubilized biomass mixture; and (d) optionally separating the lignan from the solubilized biomass mixture.

In some embodiments, the polyamine has the chemical structure:

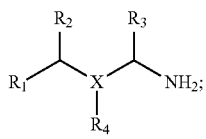

wherein X is C or N; and $R_1$, $R_2$, $R_3$, and $R_4$, are each independently —H, —$NH_2$, alkyl, alkenyl, alkynyl, aryl, alkyl amine, alkenyl amine, alkynyl amine, or aryl amine.

In some embodiments, the polyamine comprises at least 2, 3, 4, or 5 N atoms or amines. In some embodiments, the polyamine comprises at least 2, 3, 4, 5, 6, 7, 8, 9, 10, 20, or 30 carbon atoms total, or having a longest chain having at least 2, 3, 4, 5, 6, 7, 8, 9, 10, 15, or 20 carbon or nitrogen atoms.

In some embodiments, each alkyl, alkenyl, alkynyl, aryl, alkyl amine, alkenyl amine, alkynyl amine, or aryl amine independently comprises at least 1, 2, 3, 4, 5, 6, 7, 8, 9, or 10 carbon atoms total, or has a longest chain having at least 1, 2, 3, 4, 5, 6, 7, 8, 9, or 10 carbon or nitrogen atoms.

In some embodiments, the polyamine is a diamine, triamine, 1,5-diaminopentane, 1,4-diaminobutane, 1,3-diaminopropane, 1,2-diaminoethane, 1,2-diaminopropane, and 1,4-diaminobutane, ethylenediamine (ethane-1,2-diamine), diethylenetriamine, 1,3-diaminopropane (trimethylenediamine), 1,4-diaminobutane (putrescine), 1,5-diaminopentane (cadaverine), 1,2-diaminopropane, spermine (N1, N1'-(butane-1,4-diyl)bis(propane-1,3-diamine)), spermidine (Ni-(3-aminopropyl)butane-1,4-diamine), 2,2-dimethyl-1,3-propanediamine, or any one of the following polyamines shown in Table 1, or a mixture thereof.

TABLE 1

| Polyamines suitable for use in the invention | |
|---|---|
| Chemical Name | Chemical Structure |
| diethylenetriamine | H₂N–⁀–N(H)–⁀–NH₂ |
| propane-1,3-diamine | H₂N–⁀–NH₂ |
| butane-1,4-diamine | H₂N–⁀⁀–NH₂ |
| pentane-1,5-diamine | H₂N–⁀⁀⁀–NH₂ |
| pentylamine | H₂N–⁀⁀ |
| propane-1,2-diamine | CH(NH₂)–CH₂NH₂ |
| spermine | H₂N–⁀⁀⁀–N(H)–⁀⁀–N(H)–⁀⁀⁀–NH₂ |
| spermidine | H₂N–⁀⁀⁀–N(H)–⁀⁀⁀⁀–NH₂ |
| 2,2-dimethylpropane-1,3-diamine | H₂N–C(CH₃)₂–NH₂ |

In some embodiments, the solvent has a viscosity having a value equal to or less than about 0.001 cP, 0.01 cp, 0.1 cP, 1 cP, 10 cP, 20 cP, 30 cP, 40 cP, or 50 cP, or within a range of any two of the preceding values, at a temperature of about 25° C. In some embodiments, the solvent has a viscosity having a value equal to or less than about 0.001 cP, 0.01 cp, 0.1 cP, 1 cP, 10, cP, 50 cP, 100 cP, 150 cP, 200 cP, 250 cP, 300 cP, 350 cP, 400 cP, 450 cP, 500 cP, 550 cP, or 600 cP, or within a range of any two of the preceding values, at a temperature of about 90° C. In some embodiments, the solvent has a viscosity having a value equal to or less than about 40 cP, 45 cp, 50 cP, 55 cP, or 60 cP at a temperature of about 90° C.

In some embodiments, the solvent has a boiling point having a value equal to or less than about 40° C., 50° C., 60° C., 70° C., 80° C., 90° C., 100° C., 110° C., 120° C., 130° C., 140° C., 150° C., 160° C., 170° C., 180° C., 190° C., or 200° C., or within a range of any two of the preceding values.

In some embodiments, the solvent or polyamine has excess enthalpy having a $H^E$ values equal to or more than about −1.8, −1.7, −1.6, −1.5, −1.4, −1.3, or −1.2, or within a range of any two of the preceding values.

Hansen solubility parameter and thermodynamic parameters (excess enthalpy and activity coefficient) the polyamine (diethylenetriamine) was identified as an effective lignin solvent (with an excess enthalpy, $H^E$ value≥−1.5)

In some embodiments, the method further comprises recovering the polyamine from the solvent, such as through low pressure or vacuum distillation. In some embodiments, the method further comprises separating the polyamine from the solubilized biomass mixture by distillation. In some embodiments, the distillation is low pressure distillation or vacuum distillation.

In some embodiments, the solvent further comprises an IL, or components thereof, and/or components that can form a deep eutectic solvent (DES).

In some embodiments, the one or more individual components are selected from the group consisting of molecules that can form ILs: cations (such as an amine containing molecules such as ethanolamine, choline, and the like) and anions (such as mineral and organic acids, such as sulfuric acid, acetic acid, and the like). In some embodiments, the introducing step (a) comprises introducing two or individual components to the biomass, wherein the two or individual components form an IL, or mixture thereof. In some embodiments, the components already present in the biomass are components that are naturally found in a biomass.

In some embodiments, the one or more individual components are selected from the group consisting of molecules that can form DES, such as halide and organic salts (such as choline chloride, zinc chloride, ammonium acetate, and the like), organic acids (such as acetic, lactic, tartaric, etc.), polyols (such as ethylene glycol, propanediol, glycerol, glucose, etc.), amines (such as urea, acetamine, thiourea, and the like).

In some embodiments, the introducing step (a) comprises introducing two or individual components to the biomass, wherein the two or individual components form a DES, or mixture thereof. In some embodiments, the introducing step (a) comprises introducing each individual component separately to the biomass.

In some embodiments, the method further comprises (b) introducing an enzyme and/or a microbe to the solubilized biomass mixture such that the enzyme and/or microbe produces a sugar from the solubilized biomass mixture. In some embodiments, the method further comprises (c) separating the sugar from the solubilized biomass mixture. In some embodiments, the method results in a yield of equal to or more than about 80%, 85%, 90%, or 95% of sugar from the biomass.

In some embodiments, step (a) does not comprise, or lacks, introducing or adding any water to the biomass or mixture. In some embodiments, the amount of water in the mixture, excluding or including water or moisture naturally found in the biomass is no more than about 10%, 9%, 8%, 7%, 6%, 5%, 4%, 3%, 2%, 1%, 0.5%, or 0.1% by weight or volume of the mixture.

The present invention provides for compositions and methods described herein. In some embodiments, the compositions and methods further comprise steps, features, and/or elements described in U.S. patent application Ser. No. 16/737,724, hereby incorporated by reference in its entirety.

In some embodiments, the method, or one-pot method, does not require any solid-liquid separation step. In some embodiments, the one-pot method does not require adjustment of the pH level in the one-pot composition. In some embodiments, the one-pot method does not require any dilution, or addition of water or medium, after pretreatment and/or before saccharification and fermentation. In some embodiments, the reaction of the enzyme and the growth of the microbe occur in the same one-pot composition. In some embodiments, the polyamine, IL, DES, or mixture thereof, is renewable as it can be continuous in use. In some embodiments, the one-pot method can produce a yield of sugar that is equal to or more than about 50%, 60%, 70%, 75%, or 80%, or any other value described herein.

In some embodiments, using bio-compatible solvents enables a one-pot biomass conversion which eliminates the needs of mass transfer between reactors and the separation of solid and liquid. In some embodiments, the method does not require recycling any catalyst and/or enzyme. In some embodiments, the method requires less water usage than current biomass pretreatment. The method can produce fuels/chemicals at a higher titer and/or yield in a single vessel without any need for intermediate units of mass transfer and/or solid/liquid separation.

The present invention provides for compositions and methods described herein.

The present invention has one or more of the following advantages: (1) Exploitation of the multiple distinct functionality of a neutral chemical molecule (polyamine) for biomass pretreatment. (2) Selective lignin extraction (high lignin solubility but very low cellulose/hemicellulose solubility). (3) Recycling and recovery via vacuum distillation.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
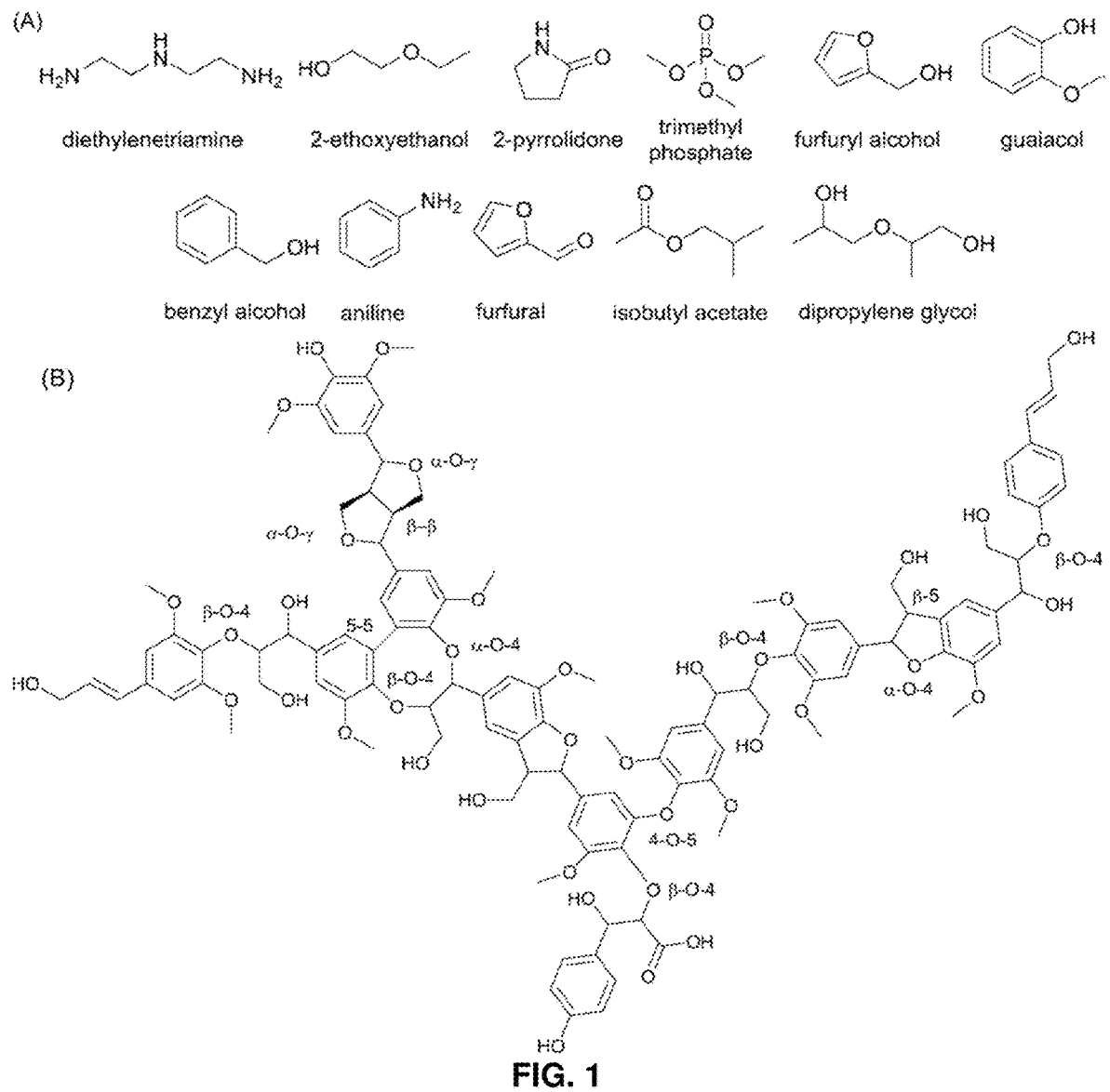
FIG. 1 Chemical structures of (A) the organic solvents screened (B) the lignin model used in this study for COSMO-RS calculations.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" when applied to a value, describes a value that includes up to 10% more than the value described, and up to 10% less than the value described.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The present invention is a unique approach to biomass pretreatment involving the use of diamines or polyamines for the deconstruction of lignocellulosic biomass. Diamines or polyamines are organic Brønsted/Lewis bases and hydrogen bond donors/acceptors molecules exhibiting manifold physicochemical. Depending on the specific multiamine being utilized, desired physical properties such as low viscosity, low to medium boiling point can also be leveraged to enable the use of environmentally benign conditions for effective lignin removal. Preliminary results show that the diamines and polyamines are capable of effectively pretreating biomass in order to selectively extract about 50%, 60%, 70%, or 80% lignin, while releasing about equal to or more than about 50%, 60%, 70%, 80%, or 90% sugars from the pretreated biomass. This represents an at least about 1-, 2-, 3-, 4-, or 5-fold increase in sugar release compared to the untreated biomass. This approach enables the cost-effective production of fermentable sugars and lignin—a major hurdle for producing commercially viable bioenergy from waste biomass.

This present invention provides for an approach to biomass pretreatment involving the use of organic amine bases with two or more amine functional groups (diamines or polyamines) for the deconstruction of different kinds of biomass into fermentable sugars and lignin. An exemplary compounds with this functional group is ethylenediamine (also known as ethane-1,2-diamine), however, analogous compounds such as diethylenetriamine, 1,3-diaminopropane (trimethylenediamine), 1,4-diaminobutane (putrescine), 1,5-diaminopentane (cadaverine), 1,2-diaminopropane, spermine (N1,N1'-(butane-1,4-diyl)bis(propane-1,3-diamine)), spermidine (N1-(3-aminopropyl)butane-1,4-diamine), 2,2-dimethyl-1,3-propanediamine are also suitable for this process.

Depending on the number of carbons on the backbone, and/or the isomeric conformation adopted, several key properties can be leveraged related to their performance as effective pretreatment solvents: (1) The ability to function as either Brønsted or Lewis base. (2) The ability to function as a Hydrogen bond donor and/or acceptor. (3) Low to medium Boiling Point for easy recovery via distillation. (4) Low viscosity.

Preliminary results show that the diamines and polyamines are capable of effectively pretreating biomass (2 mm Sorghum, 140° C., 3 h, 20% solids loading) by selectively extracting lignin. These chemicals can remove lignin from the raw biomass at a rate equal to or more than about 50%, 60%, 70%, or 80% while leaving about equal to or more than about 50%, 60%, 70%, 80%, or 90% of the hemicellulose and cellulose present. The pretreated biomass (when hydrolyzed using 10 mg Ctec3/Htec3 9/1 per gram of biomass) can release about equal to or more than about 50%, 60%, 70%, 80%, or 90% sugars (based on a total process yield)—which can represent an at least about 1-, 2-, 3-, 4-, or 5-fold increase in sugar release compared to the untreated biomass. Also, a major constraint of the biomass pretreatment state of art is the loss of hemicellulose along with the lignin after pretreatment. Interestingly, unlike conventional pretreatment using bases, hemicellulose was retained in the biomass when di- or polyamines were employed. This presents an opportunity for developing selective biomass fractionation techniques. The potential uses for this invention could include converting waste biomass (from agricultural residues, wood/paper/pulping, grasses) into biofuels and/or bioproducts. This process helps in achieving high concentration of fermentable sugars while leaving the residual lignin for valuable chemicals.

In some embodiments, the introducing step (a) comprises contacting a biomass and one or more individual components of an IL and/or DES. In some embodiments, the contacting step comprises introducing, adding and/or mixing the biomass with the one or more individual components of an IL and/or DES, or vice versa.

In some embodiments, the introducing one or more individual components of an IL and/or DES to a biomass takes place in a vessel and homogenized. In some embodiments, the loading is solid loading and controlled at about 5%, 10%, 15%, 20%, 25%, 30%, 35%, or 40%, or a range within any two preceding values. In some embodiments, the biomass and IL and/or DES components are heated, such as to 100° C., 110° C., 120° C., 130° C., 140° C., 150° C., 160° C., 170° C., 180° C., 190° C., 200° C., 200° C., 212° C., or a range within any two preceding values, for a period of time, such as about 1 h, 2 h, 3 h, 4 h, or 5 h, or a range within any two preceding values. In some embodiments, after pretreatment, the mixture is cooled, such as for a period of about at least 30 mins, such as at room temperature, or about 25° C., and/or then washed at least about 1×, 2×, 3×, 4×, or 5× with water, such as deionized water. In some embodiments, the resulting solid is recovered, such as separating the solid portion with the liquid portion.

In some embodiments, the biomass is a lignocellulosic biomass. In some embodiments, the vessel is made of a material that is inert, such as stainless steel or glass, that does not react or interfere with the reactions in the pretreatment mixture.

In some embodiments, the method uses a one-pot methodology, for example, using method steps and compositions as taught in U.S. patent application Ser. No. 16/737,724 (which is incorporated by reference). In some embodiments, the method further comprises heating the one-pot composition, optionally also comprising the enzyme and/or microbe, to a temperature that is equal to, about, or near the optimum temperature for the enzymatic activity of the enzyme and/or growth of the microbe. In some embodiments, the enzyme is a genetically modified host cell capable of converting the cellulose in the biomass into a sugar. In some embodiments, there is a plurality of enzymes. In some embodiments, the microbe is a genetically modified host cell capable of converting a sugar produced from the biomass into a biofuel and/or chemical compound. In some embodiments, there is a plurality of microbes. In some embodiments, the method produces a sugar and a lignin from the biomass. The lignin can further be processed to produce an IL or DES. The sugar is used for growth by the microbe.

In some embodiments, the solubilizing is full, near full (such as at least about 70, 80, or 90%), or partial (such as at least about 10, 20, 30, 40, 50, or 60%). In some embodiments, the one-pot composition is a slurry. When the step (a), and optionally steps (c) and/or (d), are continuous, the one-pot composition is in a steady state.

Ionic Liquid

Ionic liquids (ILs) are salts that are liquids rather than crystals at room temperatures. It will be readily apparent to those of skill that numerous ILs can be used in the present invention. In some embodiments of the invention, the IL is suitable for pretreatment of the biomass and for the hydrolysis of cellulose by thermostable cellulase. Suitable ILs are taught in ChemFiles (2006) 6(9) (which are commercially available from Sigma-Aldrich, Milwaukee, Wis.). Such suitable ILs include, but are not limited to, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is a methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

In some embodiments, the IL includes, but is not limited to, 1-ethyl-3-methylimidazolium acetate (EMIN Acetate), 1-ethyl-3-methylimidazolium chloride (EMIN Cl), 1-ethyl-3-methylimidazolium hydrogensulfate (EMIM $HOSO_3$), 1-ethyl-3-methylimidazolium methylsulfate (EMIM $MeOSO_3$), 1-ethyl-3-methylimidazolium ethylsulfate (EMIM $EtOSO_3$), 1-ethyl-3-methylimidazolium methanesulfonate (EMIM $MeSO_3$), 1-ethyl-3-methylimidazolium tetrachloroaluminate (EMIM $AiCl_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM $HOSO_3$), 1-butyl-3-methylimidazolium methanesulfonate (BMIM $MeSO_3$), 1-butyl-3-methylimidazolium methylsulfate (BMIM $MeOSO_3$), 1-butyl-3-methylimidazolium tetrachloroaluminate (BMIM AlCl4), 1-butyl-3-methylimidazolium thiocyanate (BMIM SCN), 1-ethyl-2,3-dimethylimidazolium ethylsulfate (EDIM $EtOSO_3$), Tris(2-hydroxyethyl)methylammonium methylsulfate (MTEOA $MeOSO_3$), 1-methylimidazolium chloride (MIM Cl), 1-methylimidazolium hydrogensulfate (MIM $HOSO_3$), 1,2,4-trimethylpyrazolium methylsulfate, tributylmethylammonium methylsulfate, choline acetate, choline salicylate, and the like.

In some embodiments, the ionic liquid is a chloride ionic liquid. In other embodiments, the ionic liquid is an imidazolium salt. In still other embodiments, the ionic liquid is a 1-alkyl-3-imidazolium chloride, such as 1-ethyl-3-methylimidazolium chloride or 1-butyl-3-methylimidazolium chloride.

In some embodiments, the ionic liquids used in the invention are pyridinium salts, pyridazinium salts, pyrimidium salts, pyrazinium salts, imidazolium salts, pyrazolium salts, oxazolium salts, 1,2,3-triazolium salts, 1,2,4-triazolium salts, thiazolium salts, isoquinolium salts, quinolinium salts isoquinolinium salts, piperidinium salts and pyrrolidinium salts. Exemplary anions of the ionic liquid include, but are not limited to halogens (e.g., chloride, floride, bromide and iodide), pseudohalogens (e.g., azide and isocyanate), alkyl carboxylate, sulfonate, acetate and alkyl phosphate.

Additional ILs suitable for use in the present invention are described in U.S. Pat. Nos. 6,177,575; 9,765,044; and, 10,155,735; U.S. Patent Application Publication Nos. 2004/0097755 and 2010/0196967; and, PCT International Patent Application Nos. PCT/US2015/058472, PCT/US2016/063694, PCT/US2017/067737, and PCT/US2017/036438 (all of which are incorporated in their entireties by reference). It will be appreciated by those of skill in the art that others ILs that will be useful in the process of the present invention are currently being developed or will be developed in the future, and the present invention contemplates their future use. The ionic liquid can comprise one or a mixture of the compounds.

In some embodiments, the IL is a protic ionic liquid (PIL). Suitable protic ionic liquids (PILs) include fused salts with a melting point less than 100° C. with salts that have higher melting points referred to as molten salts. Suitable PPILs are disclosed in Greaves et al. "Protic Ionic Liquids: Properties and Applications" Chem. Rev. 108(1):206-237 (2008). PILs can be prepared by the neutralization reaction of certain Brønsted acids and Brønsted bases (generally from primary, secondary or tertiary amines, which are alkaline) and the fundamental feature of these kinds of ILs is that their cations have at least one available proton to form hydrogen bond with anions. In some embodiments, the protic ionic liquids (PILs) are formed from the combination of organic ammonium-based cations and organic carboxylic acid-based anions. PILs are acid-base conjugate ILs that can be synthesized via the direct addition of their acid and base precursors. In some embodiments, the PIL is a hydroxyalkylammonium carboxylate. In some embodiments, the hydroxyalkylammonium comprises a straight or branched C1, C2, C3, C4, C5, C6, C7, C8, C9, or C10 chain. In some embodiments, the carboxylate comprises a straight or branched C1, C2, C3, C4, C5, C6, C7, C8, C9, or C10 chain. In some embodiments, the carboxylate is substituted with one or more hydroxyl groups. In some embodiments, the PIL is a hydroxyethylammonium acetate.

In some embodiments, the protic ionic liquid (PIL) is disclosed by U.S. Patent Application Publication No. 2004/0097755, hereby incorporated by reference.

Suitable salts for the method include combinations of organic ammonium-based cations (such as ammonium, hydroxyalkylammonium, or dimethylalkylammonium) with organic carboxylic acid-based anions (such as acetic acid derivatives (C1-C8), lactic acid, glycolic acid, and DESs such as ammonium acetate/lactic acid).

Suitable IL, such as distillable IL, are disclosed in Chen et al. "Distillable Ionic Liquids: reversible Amide O Alkylation", Angewandte Comm. 52:13392-13396 (2013), King et al. "Distillable Acid-Base Conjugate Ionic Liquids for Cellulose Dissolution and Processing", Angewandte Comm. 50:6301-6305 (2011), and Vijayaraghavan et al. "$CO_2$-based Alkyl Carbamate Ionic Liquids as Distillable Extraction Solvents", ACS Sustainable Chem. Engin. 2:31724-1728 (2014), all of which are hereby incorporated by reference.

Suitable PIL, such as distillable PIL, are disclosed in Idris et al. "Distillable Protic Ionic Liquids for Keratin Dissolution and Recovery", ACS Sustainable Chem. Engin. 2:1888-1894 (2014) and Sun et al. "One-pot integrated biofuel production using low-cost biocompatible protic ionic liquids", *Green Chem.* 19(13):3152-3163 (2017), all of which are hereby incorporated by reference.

In some embodiments, the PILs are formed with the combination of organic ammonium-based cations and organic carboxylic acid-based anions. PILs are acid-base conjugate ILs that can be synthesized via the direct addition of their acid and base precursors. Additionally, when sufficient energy is employed, they can dissociate back into their neutral acid and base precursors, while the PILs are re-formed upon cooling. This presents a suitable way to recover and recycle the ILs after their application. In some embodiments, the PIL (such as hydroxyethylammonium acetate—[Eth][OAc]) is an effective solvent for biomass pretreatment and is also relatively cheap due to its ease of synthesis (Sun et al., *Green Chem.* 19(13):3152-3163 (2017)).

Deep Eutectic Solvent (Des)

DESs are systems formed from a eutectic mixture of Lewis or Brønsted acids and bases which can contain a variety of anionic and/or cationic species. DESs can form a eutectic point in a two-component phase system. DESs are formed by complexation of quaternary ammonium salts (such as, choline chloride) with hydrogen bond donors (HBD) such as amines, amides, alcohols, or carboxylic acids. The interaction of the HBD with the quaternary salt reduces the anion-cation electrostatic force, thus decreasing the melting point of the mixture. DESs share many features of conventional ionic liquid (IL), and promising applications would be in biomass processing, electrochemistry, and the like. In some embodiments, the DES is any combination of Lewis or Brønsted acid and base. In some embodiments, the Lewis or Brønsted acid and base combination used is distillable.

In some embodiments, DES is prepared using an alcohol (such as glycerol or ethylene glycol), amines (such as urea), and an acid (such as oxalic acid or lactic acid). The present invention can use renewable DESs with lignin-derived phenols as HBDs. Both phenolic monomers and phenol mixture readily form DES upon heating at 100° C. with specific molar ratio with choline chloride. This class of DES does not require a multistep synthesis. The DES is synthesized from lignin which is a renewable source.

Both monomeric phenols and phenol mixture can be used to prepare DES. DES is capable of dissolving biomass or lignin, and can be utilized in biomass pretreatment and other applications. Using DES produced from biomass could lower the cost of biomass processing and enable greener routes for a variety of industrially relevant processes.

The DES, or mixture thereof, is bio-compatible: meaning the DES, or mixture thereof, does not reduce or does not significantly reduce the enzymatic activity of the enzyme, and/or is not toxic, and/or does not reduce or significantly reduce, the growth of the microbe. A "significant" reduction is a reduction to 70, 80, 90, or 95% or less of the enzyme's enzymatic activity and/or the microbe's growth (or doubling time), if the DES, or mixture thereof, was not present.

In some embodiments, the DES, or mixture thereof, comprises a quaternary ammonium salt and/or glycerol. In some embodiments, the DES, or mixture thereof, comprises a quaternary ammonium salt and/or glycerol. In some embodiments, the quaternary ammonium salt and/or glycerol have a molar ratio of about 1:1 to about 1:3. In some embodiments, the quaternary ammonium salt and/or glycerol have a molar ratio of about 1:1.5 to about 1:2.5. In some embodiments, the quaternary ammonium salt and/or glycerol have a molar ratio of about 1:1.8 or 1:1.9 to about 1:2.1 or 1:2.2. In some embodiments, the quaternary ammonium salt and/or glycerol have a molar ratio of about 1:2. In some embodiments, the quaternary ammonium salt is a choline halide, such choline chloride.

In some embodiments, the DES is distillable if the DES can be recovered at least equal to or more than about 50%, 55%, 60%, 65%, 70%, 75%, 80%, or 85% yield by distilling over vacuum at a temperature at about 100° C., 110° C., 120° C., 130° C., 140° C., 150° C., or 160° C., or any temperature between any two of the preceding temperatures.

In some embodiments, the DES can be one taught in WO 2018/204424 (Seema Singh et al.), which is hereby incorporated in its entirety by reference.

In some embodiments, the method further comprises heating the one-pot composition, optionally also comprising the enzyme and/or microbe, to a temperature that is equal to, about, or near the optimum temperature for the enzymatic activity of the enzyme and/or growth of the microbe. In some embodiments, the enzyme is a genetically modified host cell capable of converting the cellulose in the biomass into a sugar. In some embodiments, there is a plurality of enzymes. In some embodiments, the microbe is a genetically modified host cell capable of converting a sugar produced from the biomass into a biofuel and/or chemical compound. In some embodiments, there is a plurality of microbes. In some embodiments, the introducing step(s) produce a sugar and a lignin from the biomass. The lignin can further be processed to produce a DES. The sugar is used for growth by the microbe.

In some embodiments, the solubilizing is full, near full (such as at least about 70, 80, or 90%), or partial (such as at least about 10, 20, 30, 40, 50, or 60%). In some embodiments, the one-pot composition is a slurry. When the steps described herein are continuous, the one-pot composition is in a steady state.

In some embodiments, the introducing step can further comprise heating the mixture comprises increasing the temperature of the solution to a value within a range of about 75° C. to about 125° C. In some embodiments, the heating step comprises increasing the temperature of the solution to a value within a range of about 80° C. to about 120° C. In some embodiments, the heating step comprises increasing the temperature of the solution to a value within a range of about 90° C. to about 110° C. In some embodiments, the heating step comprises increasing the temperature of the solution to about 100° C.

Enzyme

In some embodiments, the enzyme is a cellulase. In some embodiments, the enzyme is thermophilic or hyperthermophilic. In some embodiments, the enzyme is any enzyme taught in U.S. Pat. Nos. 9,322,042; 9,376,728; 9,624,482; 9,725,749; 9,803,182; and 9,862,982; and PCT International Patent Application Nos. PCT/US2015/000320, PCT/US2016/063198, PCT/US2017/036438, PCT/US2010/032320, and PCT/US2012/036007 (all of which are incorporated in their entireties by reference).

Microbe

In some embodiments, the microbe is any prokaryotic or eukaryotic cell, with any genetic modifications, taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/US2011/058660, PCT/US2011/059784, PCT/

US2011/061900, PCT/US2012/031025, and PCT/US2013/074214 (all of which are incorporated in their entireties by reference).

Generally, although not necessarily, the microbe is a yeast or a bacterium. In some embodiments, the microbe is *Rhodosporidium toruloides* or *Pseudomonas putida*. In some embodiments, the microbe is a Gram negative bacterium. In some embodiments, the microbe is of the phylum Proteobactera. In some embodiments, the microbe is of the class Gammaproteobacteria. In some embodiments, the microbe is of the order Enterobacteriales. In some embodiments, the microbe is of the family Enterobacteriaceae. Examples of suitable bacteria include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus* taxonomical classes. Suitable eukaryotic microbes include, but are not limited to, fungal cells. Suitable fungal cells are yeast cells, such as yeast cells of the *Saccharomyces* genus.

Yeasts suitable for the invention include, but are not limited to, *Yarrowia, Candida, Bebaromyces, Saccharomyces, Schizosaccharomyces* and *Pichia* cells. In some embodiments, the yeast is *Saccharomyces cerevisae*. In some embodiments, the yeast is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis* and *C. zeylenoides*. In some embodiments, the yeast is *Candida tropicalis*. In some embodiments, the yeast is a non-oleaginous yeast. In some embodiments, the non-oleaginous yeast is a *Saccharomyces* species. In some embodiments, the *Saccharomyces* species is *Saccharomyces cerevisiae*. In some embodiments, the yeast is an oleaginous yeast. In some embodiments, the oleaginous yeast is a Rhodosporidium species. In some embodiments, the Rhodosporidium species is Rhodosporidium toruloides.

In some embodiments the microbe is a bacterium. Bacterial host cells suitable for the invention include, but are not limited to, *Escherichia, Corynebacterium, Pseudomonas, Streptomyces*, and *Bacillus*. In some embodiments, the *Escherichia* cell is an *E. coli, E. albertii, E. fergusonii, E. hermanii*, E. *marmotae*, or *E. vulneris*. In some embodiments, the *Corynebacterium* cell is *Corynebacterium glutamicum, Corynebacterium kroppenstedtii, Corynebacterium alimapuense, Corynebacterium amycolatum, Corynebacterium diphtheriae, Corynebacterium efficiens, Corynebacterium jeikeium, Corynebacterium macginleyi, Corynebacterium matruchotii, Corynebacterium minutissimum, Corynebacterium renale, Corynebacterium striatum, Corynebacterium ulcerans, Corynebacterium urealyticum*, or *Corynebacterium* uropygiale. In some embodiments, the *Pseudomonas* cell is a *P. putida, P. aeruginosa, P. chlororaphis, P. fluorescens, P. pertucinogena, P. stutzeri, P. syringae, P. cremoricolorata, P. entomophila, P. fulva, P. monteilii, P. mosselii, P. oryzihabitans, P. parafluva*, or *P. plecoglossicida*. In some embodiments, the *Streptomyces* cell is a *S. coelicolor, S. lividans, S. venezuelae, S. ambofaciens, S. avermitilis, S. albus*, or S. scabies. In some embodiments, the *Bacillus* cell is a *B. subtilis, B. megaterium, B. licheniformis, B. anthracis, B. amyloliquefaciens*, or *B. pumilus*.

Biofuel

In some embodiments, the biofuel produced is ethanol, or any other organic molecule, described produced in a cell taught in U.S. Pat. Nos. 7,985,567; 8,420,833; 8,852,902; 9,109,175; 9,200,298; 9,334,514; 9,376,691; 9,382,553; 9,631,210; 9,951,345; and 10,167,488; and PCT International Patent Application Nos. PCT/US14/48293, PCT/US2018/049609, PCT/US2017/036168, PCT/US2018/029668, PCT/US2008/068833, PCT/US2008/068756, PCT/US2008/068831, PCT/US2009/042132, PCT/US2010/033299, PCT/US2011/053787, PCT/US2011/058660, PCT/US2011/059784, PCT/US2011/061900, PCT/US2012/031025, and PCT/US2013/074214 (all of which are incorporated in their entireties by reference).

Biomass

The biomass can be obtained from one or more feedstock, such as softwood feedstock, hardwood feedstock, grass feedstock, and/or agricultural feedstock, or a mixture thereof.

Softwood feedstocks include, but are not limited to, *Araucaria* (e.g. *A. cunninghamii, A. angustifolia, A. araucana*); softwood Cedar (e.g. *Juniperus virginiana, Thuja plicata, Thuja occidentalis, Chamaecyparis thyoides Callitropsis nootkatensis*); Cypress (e.g. *Chamaecyparis, Cupressus Taxodium, Cupressus arizonica, Taxodium distichum, Chamaecyparis obtusa, Chamaecyparis lawsoniana, Cupressus* sempervirens); Rocky Mountain Douglas fir; European Yew; Fir (e.g. *Abies balsamea, Abies alba, Abies procera, Abies amabilis*); Hemlock (e.g. *Tsuga canadensis, Tsuga mertensiana, Tsuga heterophylla*); Kauri; Kaya; Larch (e.g. *Larix decidua, Larix kaempferi, Larix laricina, Larix occidentalis*); Pine (e.g. *Pinus nigra, Pinus banksiana, Pinus contorta, Pinus radiata, Pinus ponderosa, Pinus resinosa, Pinus sylvestris, Pinus strobus, Pinus monticola, Pinus lambertiana, Pinus taeda, Pinus palustris, Pinus rigida, Pinus echinata*); Redwood; Rimu; Spruce (e.g. *Picea abies, Picea mariana, Picea rubens, Picea sitchensis, Picea glauca*); Sugi; and combinations/hybrids thereof.

For example, softwood feedstocks which may be used herein include cedar; fir; pine; spruce; and combinations thereof. The softwood feedstocks for the present invention may be selected from loblolly pine (*Pinus taeda*), radiata pine, jack pine, spruce (e.g., white, interior, black), Douglas fir, *Pinus silvestris, Picea abies*, and combinations/hybrids thereof. The softwood feedstocks for the present invention may be selected from pine (e.g. *Pinus radiata, Pinus taeda*); spruce; and combinations/hybrids thereof.

Hardwood feedstocks include, but are not limited to, Acacia; Afzelia; Synsepalum duloificum; *Albizia*; Alder (e.g. *Alnus glutinosa, Alnus rubra*); Applewood; Arbutus; Ash (e.g. *F. nigra, F. quadrangulata, F. excelsior, F. pennsylvanica lanceolata, F. latifolia, F. profunda, F. americana*); Aspen (e.g. *P. grandidentata, P. tremula, P. tremuloides*); Australian Red Cedar (*Toona ciliata*); Ayna (Distemonanthus benthamianus); Balsa (Ochroma pyramidale); Basswood (e.g. *T. americana, T. heterophylla*); Beech (e.g. *F. sylvatica, F. grandifolia*); Birch; (e.g. *Betula populifolia, B. nigra, B. papyrifera, B. lenta, B. alleghaniensis*/B. *lutea, B. pendula, B. pubescens*); Blackbean; Blackwood; Bocote; Boxelder; Boxwood; Brazilwood; Bubing a; Buckeye (e.g. *Aesculus hippocastanum, Aesculus glabra, Aesculus flava/Aesculus octandra*); Butternut; *Catalpa*; Chemy (e.g. *Prunus serotina, Prunus pennsylvanica, Prunus avium*); Crabwood; Chestnut; Coachwood; Cocobolo; Corkwood; Cottonwood (e.g. *Populus balsamifera, Populus deltoides, Populus sargentii, Populus heterophylla*); Cucumbertree; Dogwood (e.g. *Cornus florida, Cornus nuttallii*); Ebony (e.g. *Diospyros kurzii, Diospyros melanida, Diospyros* crassiflora); Elm (e.g. *Ulmus americana, Ulmus procera, Ulmus thomasii, Ulmus rubra, Ulmus glabra*); *Eucalyptus*; Greenheart; Grenadilla; Gum (e.g. *Nyssa sylvatica, Eucalyptus globulus, Liquidambar styraciflua, Nyssa aquatica*);

Hickory (e.g. *Carya alba*, *Carya glabra*, *Carya ovata*, *Carya laciniosa*); Hornbeam; Hophornbeam; Ipe; Iroko; Ironwood (e.g. Bangkirai, *Carpinus caroliniana*, *Casuarina equisetifolia*, Choricbangarpia subargentea, Copaifera spp., Eusideroxylon zwageri, Guajacum *officinale*, Guajacum sanctum, Hopea *odorata*, Ipe, Krugiodendronferreum, Lyonothamnus lyonii (L. floribundus), Mesua *ferrea*, Olea spp., Olneya tesota, *Ostrya virginiana*, *Parrotia persica*, *Tabebuia* serratifolia); *Jacaranda*; Jotoba; Lacewood; Laurel; Limba; Lignum vitae; Locust (e.g. *Robinia* pseudacacia, *Gleditsia triacanthos*); Mahogany; Maple (e.g. *Acer saccharum*, *Acer nigrum*, *Acer negundo*, *Acer rubrum*, *Acer saccharinum*, *Acer pseudoplatanus*); Meranti; Mpingo; Oak (e.g. *Quercus macrocarpa*, *Quercus alba*, *Quercus stellata*, *Quercus bicolor*, *Quercus virginiana*, *Quercus michauxii*, *Quercus prinus*, *Quercus muhlenbergii*, *Quercus chrysolepis*, *Quercus lyrata*, *Quercus robur*, *Quercus petraea*, *Quercus rubra*, *Quercus velutina*, *Quercus laurifolia*, *Quercus falcata*, *Quercus nigra*, *Quercus phellos*, *Quercus texana*); Obeche; Okoum6; Oregon Myrtle; California Bay Laurel; Pear; Poplar (e.g. *P. balsamifera*, *P. nigra*, Hybrid Poplar (Populusxcanadensis)); Ramin; Red cedar; Rosewood; Sal; Sandalwood; *Sassafras*; Satinwood; Silky Oak; Silver Wattle; Snakewood; Sourwood; Spanish cedar; American sycamore; Teak; Walnut (e.g. *Juglans nigra*, *Juglans regia*); Willow (e.g. *Salix nigra*, *Salix alba*); Yellow poplar (*Liriodendron tulipifera*); Bamboo; Palmwood; and combinations/hybrids thereof.

For example, hardwood feedstocks for the present invention may be selected from Acacia, Aspen, Beech, *Eucalyptus*, Maple, Birch, Gum, Oak, Poplar, and combinations/hybrids thereof. The hardwood feedstocks for the present invention may be selected from *Populus* spp. (e.g. *Populus tremuloides*), *Eucalyptus* spp. (e.g. *Eucalyptus globulus*), *Acacia* spp. (e.g. *Acacia dealbata*), and combinations thereof.

Grass feedstocks include, but are not limited to, $C_4$ or $C_3$ grasses, e.g. Switchgrass, Indiangrass, Big Bluestem, Little Bluestem, Canada Wildrye, Virginia Wildrye, and Goldenrod wildflowers, etc, amongst other species known in the art.

Agricultural feedstocks include, but are not limited to, agricultural byproducts such as husks, stovers, foliage, and the like. Such agricultural byproducts can be derived from crops for human consumption, animal consumption, or other non-consumption purposes. Such crops can be corps such as corn, wheat, sorghum, rice, soybeans, hay, potatoes, cotton, or sugarcane. The feedstock can arise from the harvesting of crops from the following practices: intercropping, mixed intercropping, row cropping, relay cropping, and the like.

In some embodiments, the biomass is an ensiled biomass. In some embodiment, the biomass is ensiled by placing the biomass in an enclosed container or room, such as a silo, or by piling it in a heap covered by an airproof layer, such as a plastic film. The biomass undergoing the ensiling, known as the silage, goes through a bacterial fermentation process resulting in production of volatile fatty acids. In some embodiment, the ensiling comprises adding ensiling agents such as sugars, lactic acid or inculants. In some embodiments, the ensiled biomass comprises one or more toxic compounds. In some embodiments, when ensiled biomass comprises one or more toxic compounds, the microbe is resistant to the one or more toxic compounds.

REFENCES CITED HEREIN

1. M. Galbe and O. Wallberg, *Biotechnol* Biofuels, 2019, 12, 294.
2. M. C. Y. Chang, *Curr. Opin. Chem. Biol.*, 2007, 11, 677-684.
3. S. I. Mussatto and G. M. Dragone, in Biomass fractionation technologies for a lignocellulosic feedstock based biorefinery, Elsevier, 2016, pp. 1-22.
4. M. V. Rodionova, R. S. Poudyal, I. Tiwari, R. A. Voloshin, S. K. Zharmukhamedov, H. G. Nam, B. K. Zayadan, B. D. Bruce, H. J. M. Hou, and S. I. Allakhverdiev, *Int. J. Hydrogen Energy*, 2017, 42, 8450-8461.
5. E. C. Achinivu, R. M. Howard, G. Li, H. Gracz, and W. A. Henderson, *Green Chem.*, 2014, 16, 1114-1119.
6. Z. Strassberger, S. Tanase, and G. Rothenberg, *RSC Adv.*, 2014, 4, 25310-25318.
7. B. M. Upton and A. M. Kasko, *Chem. Rev.*, 2016, 116, 2275-2306.
8. P. Kumar, D. M. Barrett, M. J. Delwiche, and P. Stroeve, *Ind Eng Chem Res*, 2009, 48, 3713-3729.
9. L. Yao, C. Chen, C. G. Yoo, X. Meng, M. Li, Y. Pu, A. J. Ragauskas, C. Dong, and H. Yang, *ACS Sustain. Chem. Eng.*, 2018, 6, 14767-14773.
10. J. Kautto, M. J. Realff, A. Ragauskas, and T. Kässi, *BioRes*, 2014, 9, 6041-6072.
11. Z. Zhang, M. D. Harrison, D. W. Rackemann, W. O. S. Doherty, and I. M. O'Hara, *Green Chem.*, 2016, 18, 360-381.
12. M. N. Borand and F. Karaosmanoğlu, *J. Renewable Sustainable Energy*, 2018, 10, 033104.
13. X. Zhao, S. Li, R. Wu, and D. Liu, *Biofuels, Bioprod. Bioref*, 2017, 11, 567-590.
14. A. Rodriguez, E. Espinosa, J. Dominguez-Robles, R. Sánchez, I. Bascón, and A. Rosal, in Pulp and paper processing, ed. S. N. Kazi, InTech, 2018.
15. H. Chen, J. Zhao, T. Hu, X. Zhao, and D. Liu, *Appl. Energy*, 2015, 150, 224-232.
16. F. Cheng, T. Ouyang, J. Sun, T. Jiang, and J. Luo, *BioRes*, 2019, 14, 486-499.
17. X. Zhao, K. Cheng, and D. Liu, *Appl. Microbiol. Biotechnol.*, 2009, 82, 815-827.
18. L. Qin, X. Li, J.-Q. Zhu, W.-C. Li, H. Xu, Q.-M. Guan, M.-T. Zhang, B.-Z. Li, and Y.-J. Yuan, *Ind. Crops Prod.*, 2017, 102, 51-57.
19. F. Cheng, X. Zhao, and Y. Hu, *Bioresour. Technol.*, 2018, 249, 969-975.
20. D. T. Balogh, A. A. S. Curvelo, and R. A. M. C. De Groote, *Holzforschung*, 1992, 46, 343-348.
21. Y. Ye, Y. Liu, and J. Chang, *Bioresources*, 2014, 9, 3417-3427.
22. J. Quesada-Medina, F. J. López-Cremades, and P. Olivares-Carrillo, *Bioresour. Technol.*, 2010, 101, 8252-8260.
23. L. Soh and M. J. Eckelman, *ACS Sustain. Chem. Eng.*, 2016, 4, 5821-5837.
24. T. T. Kwok, K. R. Bright, M. J. Realff, and A. S. Bommarius, *BioRes*, 2019, 14, 5988-6003.
25. L. P. Novo and A. A. S. Curvelo, *Ind Eng Chem Res*, 2019, 58, 14520-14527.
26. C. M. Hansen, Hansen Solubility Parameters: A User's Handbook, Second Edition, Crc Press, Boca Raton, 2nd edn., 2007.
27. C. Balaji, T. Banerjee, and V. V. Goud, *J. Solution Chem.*, 2012, 41, 1610-1630.
28. A. Casas, J. Palomar, M. V. Alonso, M. Oliet, S. Omar, and F. Rodriguez, *Ind. Crops Prod.*, 2012, 37, 155-163.

29. A. Casas, S. Omar, J. Palomar, M. Oliet, M. V. Alonso, and F. Rodriguez, *RSC advances*, 2013, 3, 3453-3460.
30. Q. Zhang, X. Tan, W. Wang, Q. Yu, Q. Wang, C. Miao, Y. Guo, X. Zhuang, and Z. Yuan, *ACS Sustain. Chem. Eng.*, 2019, 7, 8678-8686.
31. Y. Zhang, H. He, K. Dong, M. Fan, and S. Zhang, *Rsc Advances*, 2017, 7, 12670-12681.
32. W. Ji, Z. Ding, J. Liu, Q. Song, X. Xia, H. Gao, H. Wang, and W. Gu, *Energy Fuels*, 2012, 26, 6393-6403.
33. R. Vanholme, B. Demedts, K. Morreel, J. Ralph, and W. Boerjan, *Plant Physiol.*, 2010, 153, 895-905.
34. C. M. Hansen and A. Bjorkman, Holzforschung-International Journal of the Biology, Chemistry, Physics and Technology of Wood, 1998, 52, 335-344.
35. W. Thielemans and R. P. Wool, *Biomacromolecules*, 2005, 6, 1895-1905.
36. K. L. Hoy, *Journal of Coated Fabrics*, 1989, 19, 53-67.
37. D. W. van Krevelen and K. te Nijenhuis, *Properties of Polymers*, 4th Edition., 2009.
38. M. Mohan, P. Viswanath, T. Banerjee, and V. V. Goud, *Mol. Phys.*, 2018, 116, 1-21.
39. J. Kahlen, K. Masuch, and K. Leonhard, *Green Chemistry*, 2010, 12, 2172-2181.
40. Y.-R. Liu, K. Thomsen, Y. Nie, S.-J. Zhang, and A. S. Meyer, *Green Chemistry*, 2016, 18, 6246-6254.
41. Y. Liu, J. Zheng, J. Xiao, X. He, K. Zhang, S. Yuan, Z. Peng, Z. Chen, and X. Lin, ACS *Omega*, 2019, 4, 19829-19839.
42. D. Song, A. F. Seibert, and G. T. Rochelle, *Energy Procedia*, 2014, 63, 1268-1286.
43. D. Song, A. F. Seibert, and G. T. Rochelle, *Energy Procedia*, 2017, 114, 2713-2727.
44. X. Zhao, R. Wu, and D. Liu, *Bioresour. Technol.*, 2018, 261, 52-61.
45. J. P. F. Simio, M. G. V. S. Carvalho, and C. M. S. G. Baptista, *Chemical Engineering Journal*, 2011, 170, 264-269.
46. A. Hartono and H. F. Svendsen, *The Journal of Chemical Thermodynamics*, 2009, 41, 973-979.
47. S. Padmanabhan, P. Schwyter, Z. Liu, G. Poon, A. T. Bell, and J. M. Prausnitz, 3 *Biotech*, 2016, 6, 23.
48. U. Koch and P. L. Popelier, *The Journal of Physical Chemistry*, 1995, 99, 9747-9754.
49. P. L. A. Popelier, *J. Phys. Chem. A*, 1998, 102, 1873-1878.
50. Sluiter, Hames, Ruiz, Scarlata, Sluiter, and Templeton, *NREL*, 2008, TP-510-42618.
51. M. D. Hanwell, D. E. Curtis, D. C. Lonie, T. Vandermeersch, E. Zurek, and G. R. Hutchison, *J. Cheminform.*, 2012, 4, 17.
52. M. Mohan, T. Banerjee, and V. V. Goud, *Journal of Chemical & Engineering Data*, 2016, 61, 2923-2932.
53. M. Gonzalez-Miquel, M. Massel, A. DeSilva, J. Palomar, F. Rodriguez, and J. F. Brennecke, *J. Phys. Chem.*: B, 2014, 118, 11512-11522.
54. M. Mohan, V. V. Goud, and T. Banerjee, *Fluid Phase Equilib.*, 2015, 395, 33-43.
55. R. Anantharaj and T. Banerjee, *Ind Eng Chem Res*, 2010, 49, 8705-8725.
56. Y. Li and Y. Jin, *Renew. Energy*, 2015, 77, 550-557.
57. F. Eckert and A. Klamt, *AIChE Journal*, 2002, 48, 369-385.
58. K. A. Kurnia, S. P. Pinho, and J. A. P. Coutinho, *Ind Eng Chem Res*, 2014, 53, 12466-12475.
59. S. Grimme, S. Ehrlich, and L. Goerigk, *J. Comput. Chem.*, 2011, 32, 1456-1465.
60. R. Ditchfield, W. J. Hehre, and J. A. Pople, *J. Chem. Phys.*, 1971, 54, 724-728.
61. Z.-D. Ding, Z. Chi, W.-X. Gu, S.-M. Gu, J.-H. Liu, and H.-J. Wang, *Carbohydr. Polym.*, 2012, 89, 7-16.
62. M. Mohan, P. K. Naik, T. Banerjee, V. V. Goud, and S. Paul, *Fluid Phase Equilibria*, 2017, 448, 168-177.
63. J. Guo, D. Zhang, C. Duan, and C. Liu, *Carbohydr. Res.*, 2010, 345, 2201-2205.
64. R. F. W. Bader, *A Quantum Theory*, 1990.
65. T. A. Keith, TK Gristmill Software, Overland Park, KS, USA, 2019.
66. E. Espinosa, E. Molins, and C. Lecomte, *Chem. Phys. Lett.*, 1998, 285, 170-173.
67. T. Lu and F. Chen, *J. Comput. Chem.*, 2012, 33, 580-592.
68. W. Humphrey, A. Dalke, and K. Schulten, *J Mol Graph*, 1996, 14, 33-8, 27.
69. C. Loschen and A. Klamt, *Ind Eng Chem Res*, 2012, 51, 14303-14308.
70. A. Niederquell, N. Wyttenbach, and M. Kuentz, *Int. J. Pharm.*, 2018, 546, 137-144.
71. M. Diedenhofen, F. Eckert, A. Hellweg, H. C. Steffen, U. Huniar, A. Klamt, C. Loschen, L. Koch, J. Reinisch, J. Schwobel, M. Suray, S. Terzi, K. Wichmann, and T. R. Rosenbaum, *COSMOquick, Version* 1.7, COSMOlogic GmbH & Co. KG, Leverkusen, Germany, 2018.
72. H. Yu, J. Hu, and J. Chang, *Ind Eng Chem Res*, 2011, 50, 7513-7519.
73. C. M. Hansen, *Journal of Paint Technology*, 1967, 39, 104-117.

Example 1

A Predictive Tool-Set for the Identification of Effective Lignocellulosic Pretreatment Solvents: A Case Study of Solvents Tailored for Lignin Extraction Pretreatment of lignocellulosic biomass is essential for efficient conversion into biofuels and bioproducts. The present study develops a predictive toolset to computationally identify solvents that are able to efficiently dissolve lignin and therefore can be used to extract it from lignocellulose during pretreatment, a process known to reduce recalcitrance to enzymatic deconstruction and increase conversion efficiency. Two approaches were taken to examine the potential of eleven organic solvents to solubilize lignin, Hansen solubility parameters (HSP) and activity coefficients and excess enthalpies of solvent/lignin mixtures predicted by COSMO-RS (COnductor like Screening MOdel for Real Solvents). The screening revealed that diethylenetriamine was the most effective solvent, promoting the highest lignin removal (79.2%) and fermentable sugar yields (>72%). Therefore, a COSMO-RS-based predictive model for the lignin removal as a function of number and type of amines was developed. Among the fitted models, non-linear regression model predicts the lignin solubility more accurately than the linear model. Experimental results demonstrated a >65% lignin removal and >70% of sugar yield from several amine-based solvents tested, which aligned very well with the model's prediction.

Finally, to help understand the dissolution mechanism of lignin by these solvents, quantum theory of atoms in molecules (QTAIM) and quantum chemical calculations (interaction energies and natural bond orbital (NBO) analysis) was performed and suggest that amines exhibit strong electrostatic interactions and hydrogen bonding strengths with lignin leading to higher lignin removal. Together, these computational tools provide an effective approach for rapidly identifying solvents that are tailored for effective biomass pretreatment.

The present study attempts to develop both predictive models to identify the best solvents for lignin dissolution and multiscale simulation approaches tailored to provide mechanistic insights into how these solvents interact with lignin. First, HSP were used to screen a wide range of molecular solvents and identify ones that may be effective at lignin extraction from lignocellulose, which were then tested experimentally to determine the accuracy of the HSP predictions. Next, COSMO-RS calculations were performed to examine the same solvents and study the solvent/lignin mixture's thermodynamic properties such as excess enthalpy, activity coefficient, and sigma potentials. The excess enthalpy and activity coefficients were then used as a method to rank these solvents ability to dissolve lignin, and this approach was compared to using HSP and found to have better predictability. The initial screening revealed that solvents containing amine were effective at dissolving lignin, so a broader class of amine-based solvents were screened using excess enthalpy and activity coefficients of solvent/lignin mixtures, and several amines were tested experimentally for their ability to extract lignin from biomass and promote efficient enzymatic saccharification of the lignocellulosic polysaccharides. This data was used to validate a COSMO-RS-based predictive model that was developed for the lignin removal as a function of number and type of amines, which can be used for future screening efforts of amine-based solvents. Finally, to gain a deeper mechanistic understanding of how these solvents act to dissolve lignin, quantum chemical simulations are performed to study the solvent's interactions with lignin. Quantum theory of atom in the molecule (QTAIM), reduced density gradient (RDG), and natural bonding orbital (NBO) analysis were also carried out to investigate the strength and nature of H-bonding present in the lignin/molecular solvents. This analysis provided key insights into lignin dissolution and revealed that H-bonding between solvent and lignin is a major driver of lignin dissolution. The predictive toolset developed in this study combined with the mechanistic insights into lignin dissolution lay a strong foundation for rapidly identifying effective solvents for biomass pretreatment and developing cost-effective lignocellulosic conversion technologies.

2. Results and Discussions 2.1. Screening of Molecular Solvents for Lignin Dissolution Lignin is a complex and random polymer that is held together with strong bonds, such as ether linkages (carbon-oxygen) and carbon-carbon bonds, as well as, weak inter- and intra-molecular forces, such as hydrogen bonds.[33] The complete (or near-complete) dissolution of lignin and its removal from lignocellulosic biomass is challenging owing to the scarcity of effective, efficient, economic, and environmentally benign solvents. Therefore, methods that enable rapid identification of effective lignin solvents could be instrumental in expanding the list of available solvents and identifying those that can be incorporated into cost-effective lignocellulose conversion technologies.

Hansen solubility parameters (HSP) could possibly be used to provide an expedient route to identifying a short list of good potential solvents for lignin dissolution. HSP values for many molecular solvents have been determined and these values are readily available. In addition, Hansen and Bjdrkman report relative energy difference (RED) values for many solvents compared to lignin.[26] RED values can be used to estimate a solvent's ability to dissolve a solute. If the RED value is less than 1, then the affinity between the solute and the solvent is said to be higher and will result in a higher dissolution capacity. If the RED is greater than 1, the affinity between the solvent and solute is lower, resulting in poor dissolution. These RED values were used as an initial screen to identify a short list of solvents with RED values less than 1 that could be tested experimentally for lignin dissolution. The solvents were intentionally selected to have different molecular functionalities to maximize the chemical space covered. Functional groups included amines (diethylenetriamine), lactams (2-pyrrolidone), alcohols (dipropylene glycol, benzyl alcohol, furfuryl alcohol, guaiacol, and 2-ethoxyethanol), ethers (2-ethoxyethanol and dipropylene glycol), esters (isobutyl acetate and trimethyl phosphate), and aromatics (benzyl alcohol, furfuryl alcohol, guaiacol, and furfural) (FIG. 1 (Panel A)).

While the Hansen and Björkman reported HSP and RED values for extracted woody lignin (14.9 for polar ($\delta_p$), 16.9 for hydrogen-bonded ($\delta_h$), and 21.9 for dispersion ($\delta_d$) contributor) are readily available, they are also based on kraft lignin extracted from pine trees during paper pulping, which is unlikely to have the same properties as intact lignin within plant biomass.[26,34] In addition, it should be noted that the reported HSP values cannot be assumed to be universal for all lignin samples as there is an extensive chemical diversity that exists between the lignins from different biomass sources. In light of these issues, we sought to identify an alternate set of lignin HSP that could be used to calculate lignin RED values to accurately rank the selected solvent's ability to dissolve lignin. Thielemans and Wool have reported the HSP values for lignin as $\delta_p$=13.7, $\delta_h$=11.7, and $\delta_d$=16.7.[35] In their model, the solubility behavior of the modified lignin was described using the Flory-Huggins solubility theory, combined with the group contribution model developed by Hoy.[35-37] This is one of the more practical lignin models available because it has contributions for a large number of functional groups, and accounts for a variety of structural features, which is important for a complex polymer like lignin.

In an attempt to develop a more accurate set of RED values for lignin solvents, the Thielemans and Wool reported HSPs were used to calculate a new set of RED values for the same solvents identified by Hansen and Bjorkman using COSMOquick. In the new set of RED values, diethylenetriamine and trimethylphosphate have the lowest RED values and are expected to be the most suitable solvents for delignification, while the other solvents are expected to extract little to no lignin (Table 2). To validate these predictions, the grassy crop sorghum was pretreated with the solvents listed in Table 2 at 140° C. for 3 h at 20 wt % solids loading. Pretreatment with diethylenetriamine resulted in the highest lignin extraction (79.2%) as predicted, but pretreatment with trimethylphosphate resulted in an unexpectedly low-level lignin extraction (28.5%; Table 2). None of the other solvents were able to extract high levels of lignin from sorghum. Therefore, the calculated RED values do not appear to be very predictive for lignin extraction from lignocellulose, and screening solvents with these values will likely result in many false positives.

TABLE 2

Hansen Solubility Parameters and RED values for lignin and the investigated molecular solvents calculated based on the COSMOquick correlated with the experimental lignin removal.

| Lignin/Solvents | Lignin removal (%) | Hansen Solubility Parameters | | | | RED[a] | RED[b] |
|---|---|---|---|---|---|---|---|
| | | $\delta_D$ | $\delta_P$ | $\delta_H$ | $\delta_T$ | | |
| Lignin[a] | — | 16.7 | 13.7 | 11.7 | 24.57 | — | — |
| Diethylenetriamine | 79.20 | 16.7 | 13.3 | 14.3 | 25.70 | 0.192 | 0.785 |
| Trimethylphosphate | 30.32 | 16.7 | 15.9 | 10.2 | 25.21 | 0.194 | 0.913 |
| 2-pyrrolidone | 36.28 | 18.2 | 12.0 | 9.0 | 23.58 | 0.320 | 0.599 |
| 2-ethoxyethanol | 28.51 | 16.2 | 9.2 | 14.3 | 23.49 | 0.386 | 0.925 |
| Dipropylene glycol | 24.07 | 16.5 | 10.6 | 17.7 | 26.42 | 0.494 | 0.831 |
| Furfuryl alcohol | 22.37 | 17.4 | 7.6 | 15.1 | 24.26 | 0.520 | 0.821 |
| Guaiacol | 26.68 | 18.0 | 7.0 | 12.0 | 22.74 | 0.525 | 0.761 |
| Furfural | 12.72 | 18.6 | 14.9 | 5.1 | 24.37 | 0.563 | 0.989 |
| Benzyl alcohol | 19.82 | 18.4 | 6.3 | 13.7 | 23.79 | 0.612 | 0.800 |
| Aniline | 16.75 | 20.1 | 5.8 | 11.2 | 23.73 | 0.762 | 0.897 |
| Isobutyl acetate | 18.29 | 15.1 | 3.7 | 6.3 | 16.77 | 0.862 | 1.470 |

[a]taken from Thielemans and Wool[35]; [b]Hansen and Björkman [26,34]reported RED values for lignin It is unclear why the HSP values are not very predictive for lignin dissolution but one explanation is that HSP values are used to measure the intermolecular affinity between solvent and solute but do not account for their intramolecular affinities, which can affect their behavior. Therefore, in order to better understand both the inter- and intramolecular interactions in a lignin/solvent mixture, COSMO-RS calculations were performed to study the mixture's thermodynamic properties such as excess enthalpy, activity coefficient, and sigma potentials. Typically, monomeric and dimeric structures of lignin have been used as lignin models to perform these molecular simulations.[27-29] However, the monomeric and dimer structures of lignin do not directly represent the lignin molecule due to the absence of many different linkages present in lignin. Therefore, in order to obtain more realistic results, a lignin structure was generated based on the G/S ratio of grassy biomass and built by joining all the major lignin linkages (β-O-4, β-β, 4-O-5, α-O-4, and β-5) present in the native lignin (FIG. 1 (Panel B)). As mentioned earlier, lignin is a heterogeneous macromolecule, therefore, it is not possible to create a single lignin structure that can fully capture that heterogeneity or represent all lignins. However, many insights can be gained by simply ensuring coverage of the typical linkages found in lignin for the biomass used for pretreatment, which is this study is the grass sorghum.

Figure 2:
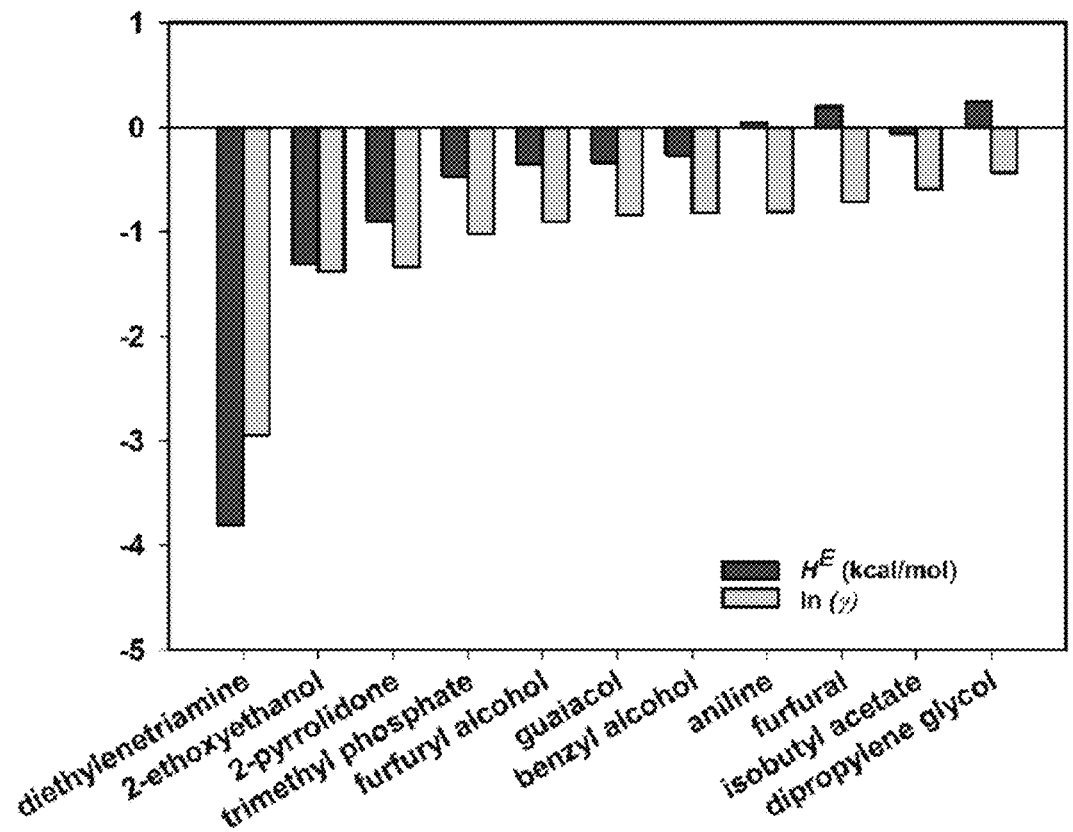
FIG. 2 COSMO-RS predicted excess enthalpy and logarithmic activity coefficients of lignin in molecular solvents.

Two thermodynamic properties in particular may be useful in predicting lignin dissolution in a solvent, excess enthalpy ($H^E$) and logarithmic activity coefficients ($\ln(\gamma)$). The $H^E$ is a useful thermodynamic property for measuring the difference in the strength of interactions between dissimilar species (i.e., lignin-solvents) in the mixture. While the $\ln(\gamma)$ values are often used as a quantitative descriptor for the dissolution power of a solvent. In the literature, $\ln(\gamma)$ has been reported as the dominating parameter in deciding the capability of a solvent and has also been successfully employed in previous studies to predict the solubility of cellulose in ILs.[28,38,39] Studies have reported that both $H^E$ and $\ln(\gamma)$ parameters are good indicators of cellulose and lignin solubility in a solvent.[28,29,40] Therefore, both $H^E$ and $\ln(\gamma)$ parameters were calculated for the model grass lignin in the same set of solvents screened by HSP to determine if they can be used to accurately predict lignin dissolution (FIG. 2). The solvent diethylenetriamine was determined to possess significantly lower $H^E$ and $\ln(\gamma)$ values (i.e., more negative) than the other solvents, including trimethylphosphate, which had a similar RED value as diethylenetriamine and was therefore predicted to be a good lignin solvent. The COSMO-RS predicted results are much more consistent with the experimental lignin removal than the HSP RED values (Table 2), suggesting the use of COSMO-RS to predict $H^E$ and $\ln(\gamma)$ parameters of lignin in solvents is a more realistic method to determine a solvents' ability to extract lignin from lignocellulose.

Figure 3:
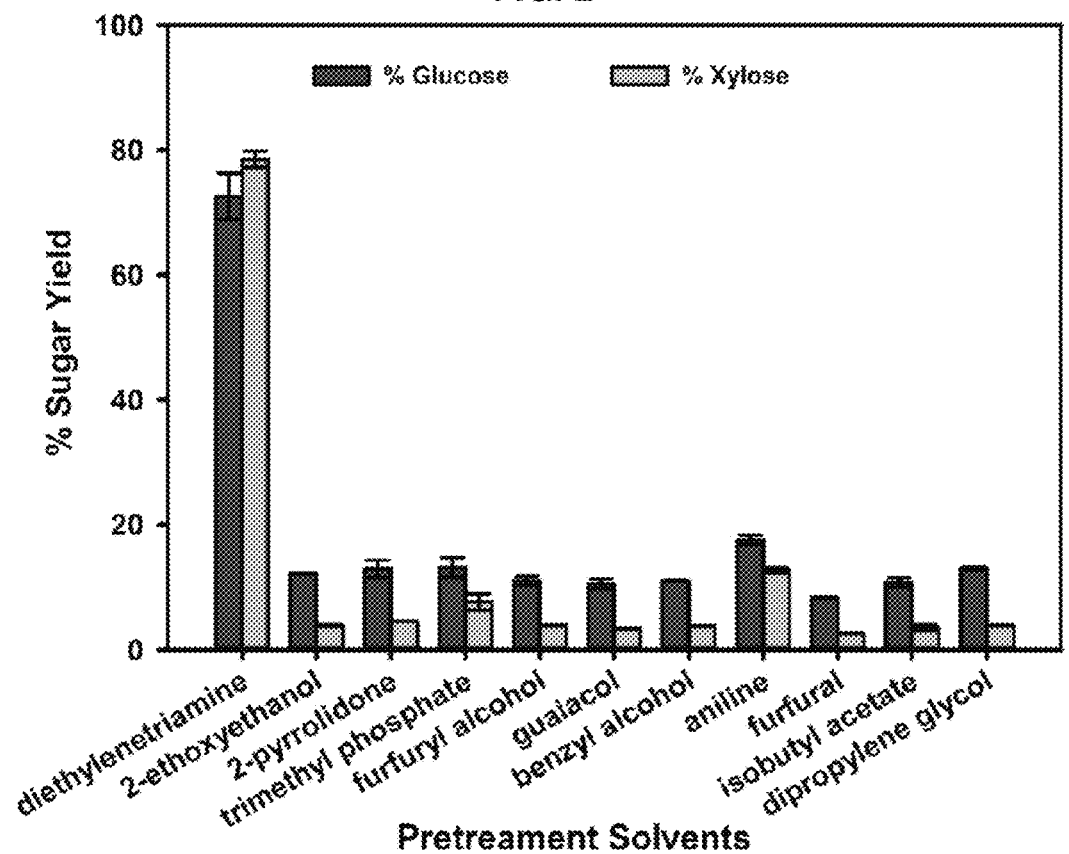
FIG. 3 Glucose and xylose yields of pretreated sorghum after enzymatic hydrolysis FIG. 4 Chemical structures of the amines evaluated in this study.
Figure 13:
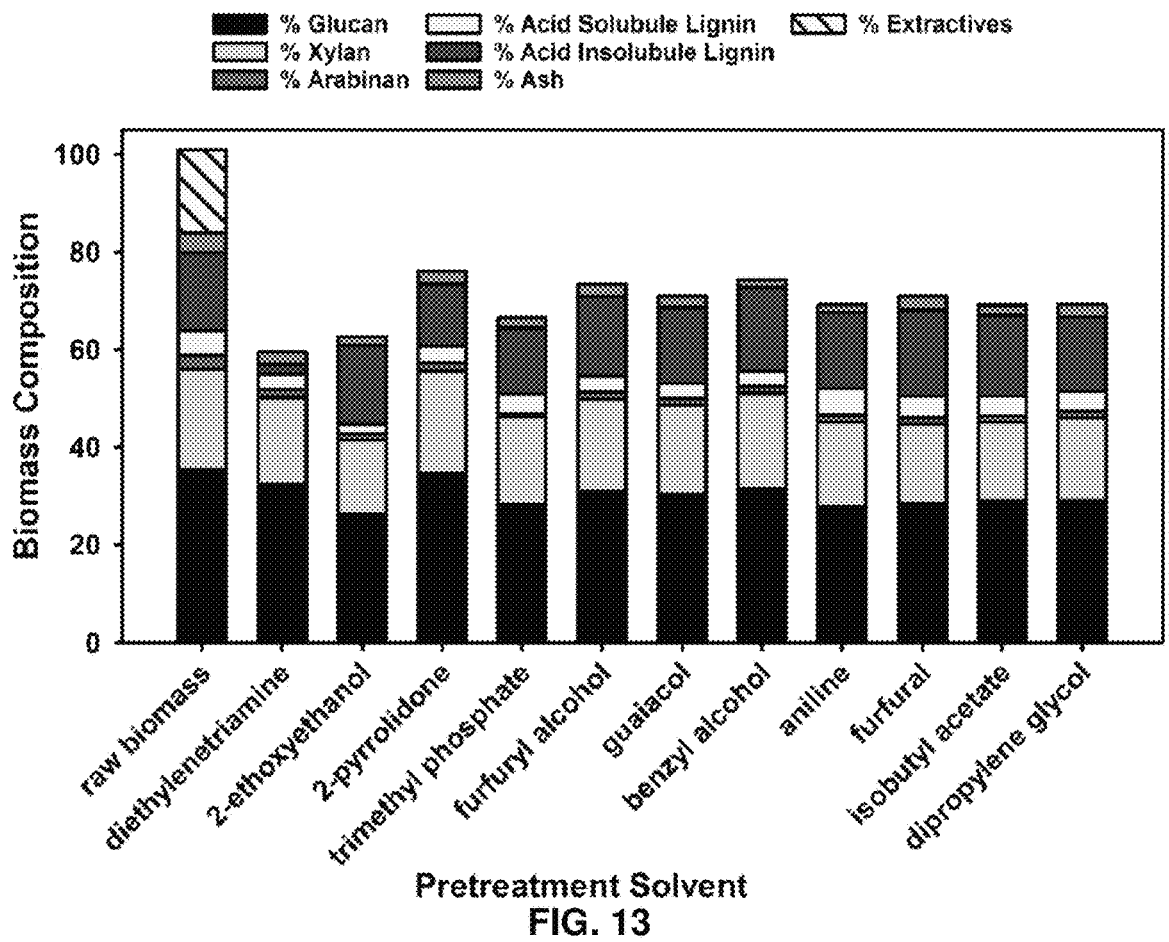
FIG. 13 Biomass yield and composition after pretreatment of sorghum with the organic solvents. The composition of the untreated "raw biomass" is also displayed.
Figure 14:
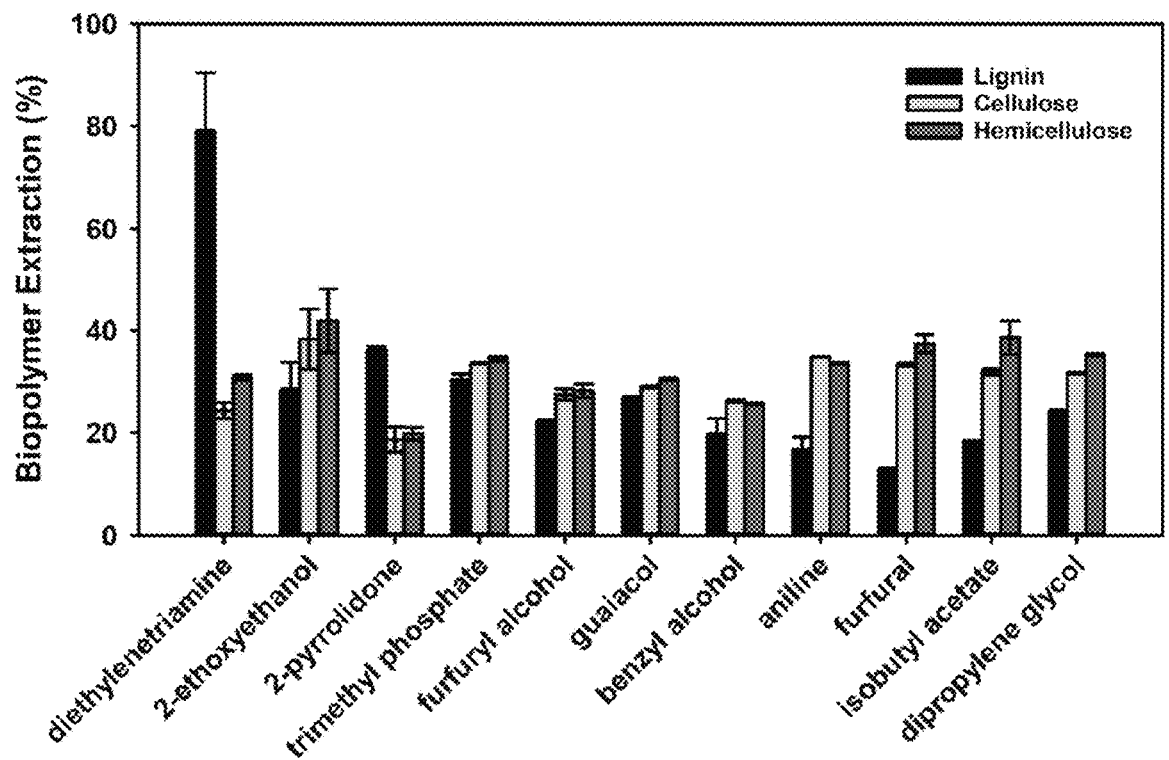
FIG. 14 Amount of each biopolymer (lignin, cellulose and hemicellulose) that was removed during pretreatment and solvent recovery.

The goal of lignin extraction from lignocellulose is to increase the efficiency of enzymatic digestion of the plant polysaccharides. Therefore, enzymatic hydrolysis of sorghum pretreated with these solvents was performed using commercial enzyme cocktails (FIG. 3). The pretreated sorghum was first washed to remove the solvent to prevent interference with enzymatic digestion and the sugar yields were calculated (equation 5) based on the recovered solids (FIGS. 13-14). These results indicate that there is a direct correlation between low $H^E$ and $\ln(\gamma)$ parameters of lignin in molecular solvents and saccharification efficiency. Diethylenetriamine had the lowest $H^E$ and $\ln(\gamma)$ parameters and promoted the highest lignin removal and highest glucose and xylose yields of 72.6% and 78.6%, respectively (FIG. 3). All other solvents investigated were unable to extract significant quantities of lignin (≤36%) and had low sugar yields (≤18% glucose and ≤13% xylose), indicating that amine solvents pretreat biomass more effectively than the other functional group categories investigated. The direct correlation between lignin removal efficacy during pretreatment and saccharification efficiency has been observed in many other studies in the literature.[16,17,41] Overall, these data suggest that a general rule can be postulated that solvents that enable high lignin solubility and subsequent plant polysaccharide digestibility will have a $H^E$ value for lignin of ≤−1.5.

Figure 15:
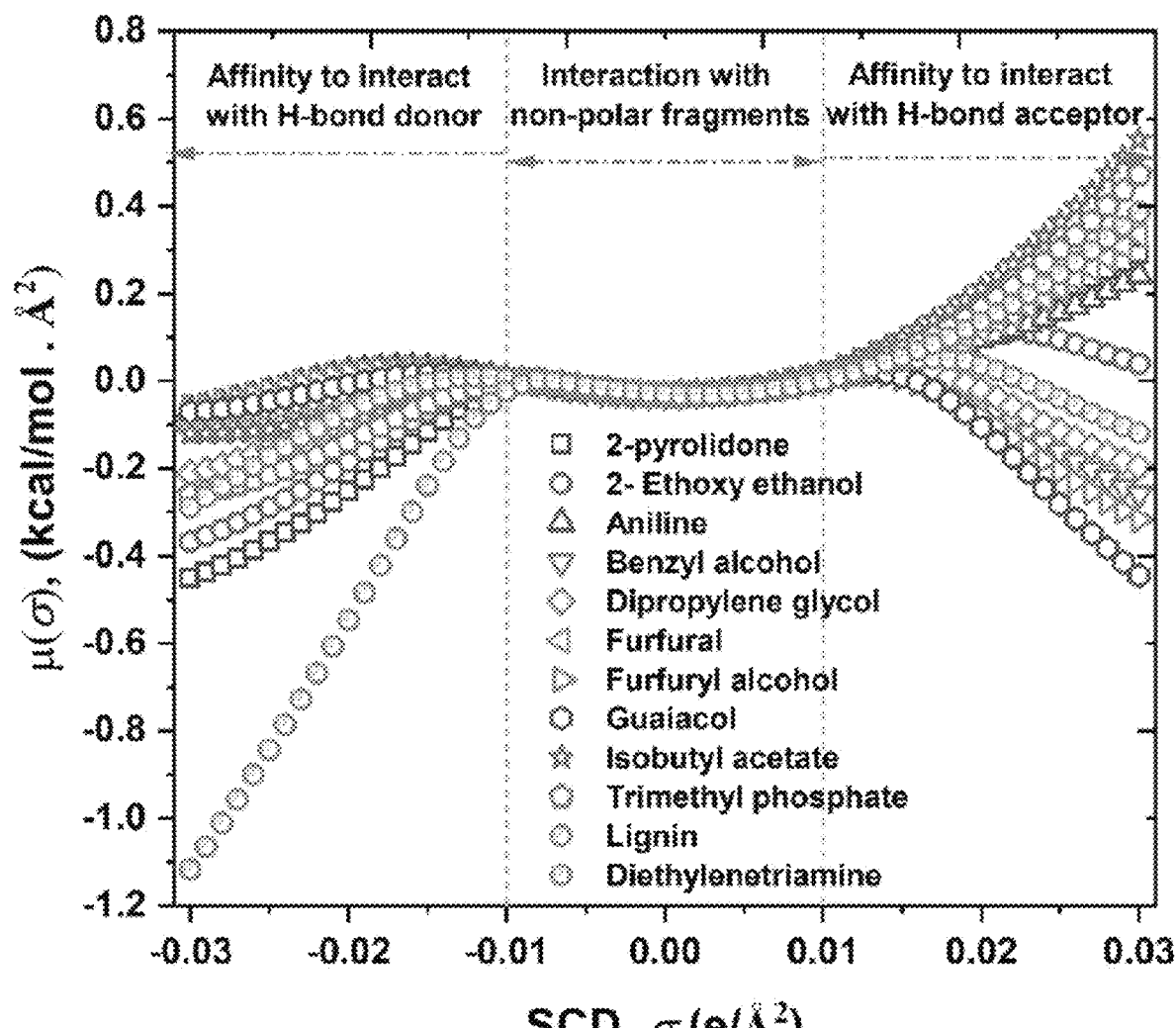
FIG. 15 (a) Sigma potentials of lignin and molecular solvents predicted by COSMO-RS. (b) COSMO cavity (surface polarity) diagram of diethylenetriamine (here the extent of screening charge varies from −0.03 e·Å$^{-2}$(red) to +0.03 e·Å$^{-2}$ (blue)). The intermediate (non-polar) region is represented by green and yellow colors.
Figure 15:
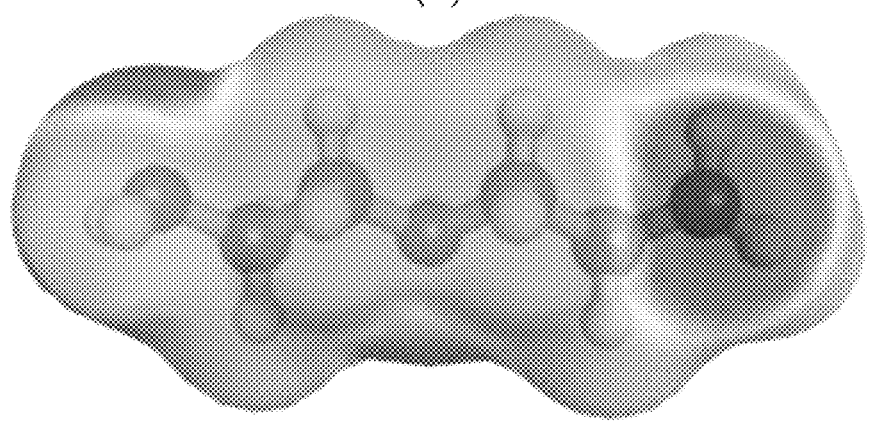

To better understand the experimental observations, sigma (σ)-potentials of the isolated molecules (solvents and lignin) were predicted using COSMO-RS. The σ-potential is a measure of the affinity of the system to a surface of polarity σ, which provides insights into a solvent's interactions with itself and with lignin. The σ-potential is divided into three regions: H-bond acceptor (σ>+0.01 e/Å$^2$), H-bond donor (σ<−0.01 e/Å$^2$), and non-polar (−0.01 e/Å$^2$<σ>+0.01 e/Å$^2$) regions. FIG. 15 (Panel a) depicts the σ-potentials of lignin and molecular solvents. On the negative side of screening charge density (SCD: σ>−0.01 e/Å$^2$), the σ-potential (μ(σ)) value of diethylenetriamine is more negative than the other solvents, which implies that diethylenetriamine has more affinity to interact with the H-bond donor surfaces (blue color in FIG. 15 (Panel b)) and has higher H-bond basicity, both of which would promote greater lignin solubility. In contrast, the μ(σ) value is positive in the region of large positive screening charge density values (σ>+0.01 e/Å$^2$), which reflects diethylenetriamine's lack of H-bond donor surfaces (FIG. 15 (Panel b)). Thus, the intramolecular interaction in diethylenetriamine is very weak, which enables the high interacting strength with the lignin. These results indicate that diethylenetriamine and potentially other amine-based solvents have an excellent ability to dissolve lignin from lignocellulosic biomass.

Figure 4:
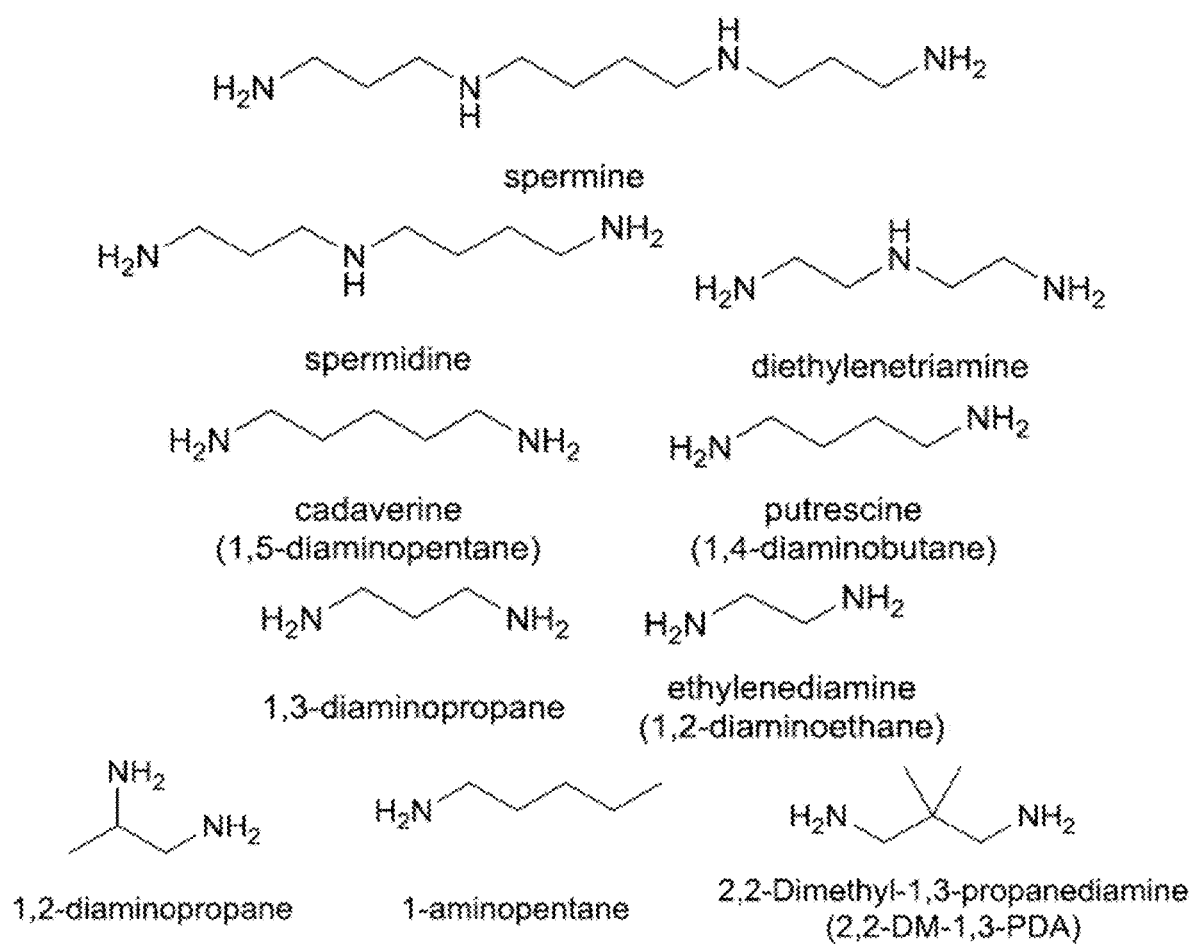

2.2. Development of COSMO-RS-Based Predictive Model for Lignin Solubility in Amines The initial solvent screen identified diethylenetriamine as an effective pretreatment solvent. This prompted a more in-depth analysis of amine-based solvents, including a broad class of amines with one or more amine functional groups. A diverse set of amines was selected to help develop a deeper understanding of the key structural features in the amines that contribute to lignin extraction and to enable the development of an effective predictive model for amine-based dissolution of lignin. The new set of solvents was selected that vary in the number, type, and position of amine groups, as well as the carbon chain length of the molecule. The amines selected include 1,3-diaminopropane, 1,4-diaminobutane, 1,5-diaminopentane, 1,2-diaminopropane, spermidine, spermine, 2,2-dimethyl-1,3-propanediamine, ethylenediamine, and pentylamine. They were compared to diethylenetriamine as the baseline (see FIG. 4).

Figure 5:
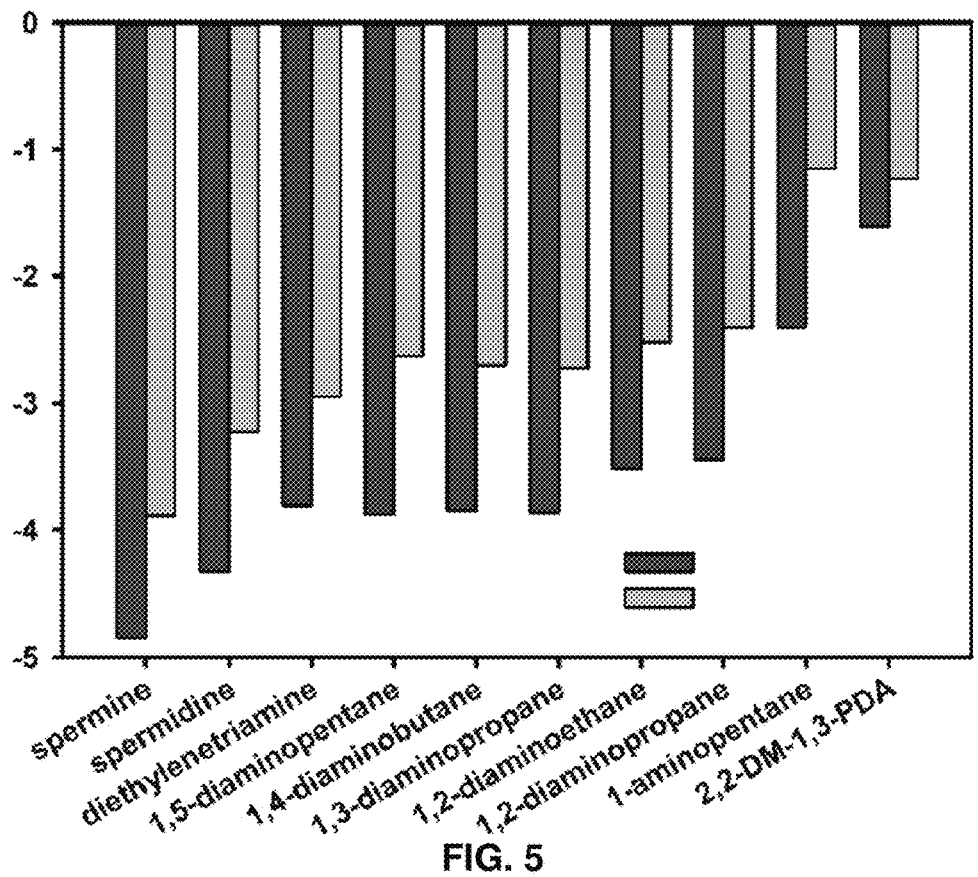
FIG. 5 COSMO-RS predicted excess enthalpy and logarithmic activity coefficients of lignin.
Figure 6:
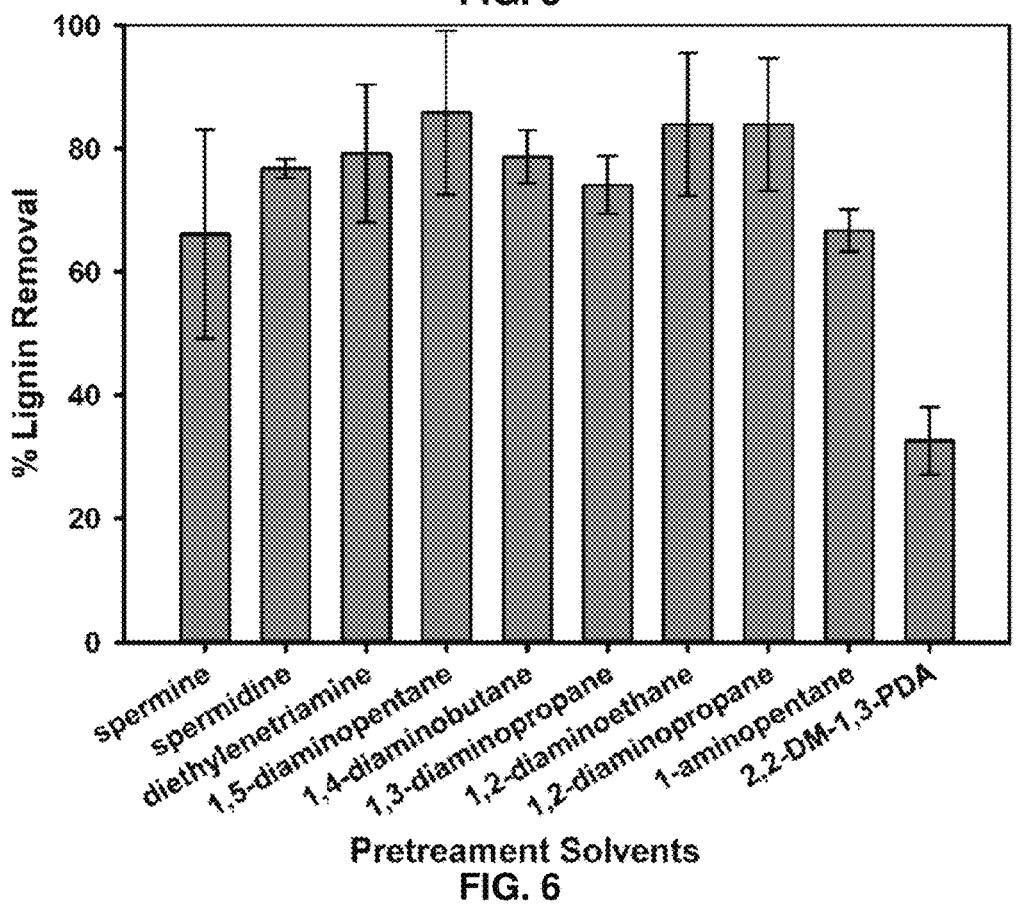
FIG. 6 Solubility of lignin measured after biomass pretreatment in amines. Pretreatment conditions: 20% solids loading, 140° C., and 3 h of reaction time.

FIG. 6 shows the COSMO-RS predicted $H^E$ and $\ln(\gamma)$ of lignin in these amine containing solvents. In the previous section, we established a general rule for lignin solubility and biomass digestibility as $H^E$ value≤−1.5. Since all the selected amines have values below this cutoff, there is a strong indication that they will all be effective solvents for lignin extraction, except possibly 2,2-dimethyl-1,3-propanediamine with a borderline $H^E$ value of −1.57 (FIG. 5). Spermine and spermidine have the lowest $H^E$ and $\ln(\gamma)$, indicating that they may be able to extract and solubilize the greatest amount of lignin. As the number of carbon and amine groups increases, the $H^E$ and $\ln(\gamma)$ are predicted to be more negative. The polyamines (compounds with >2 amine groups) have $H^E$≤−3.8 and are predicted to have the highest lignin solubility capacity, while the diamines, are expected to have a intermediate lignin dissolution ability −3.8≤$H^E$←2.5. Finally, the branched diamine (2,2-dimethyl-1,3-propanediamine) and monoamine (1-aminopentane) with −2.5<$H^E$<−1.5 are expected to have the lowest lignin extraction capacity.

Figure 16:
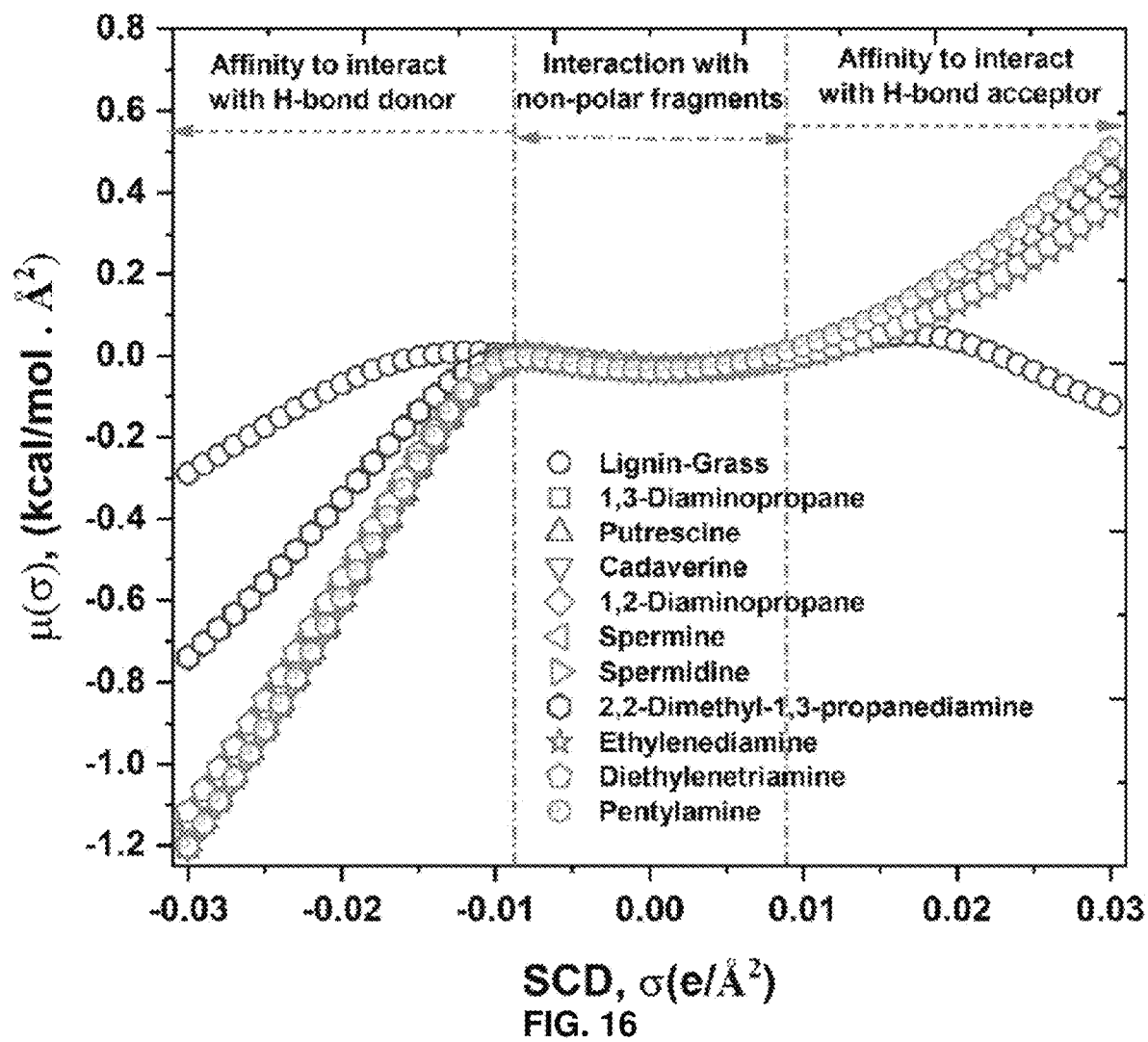
FIG. 16 COSMO-RS-based predicted sigma potentials of lignin and amines.
Figure 17:
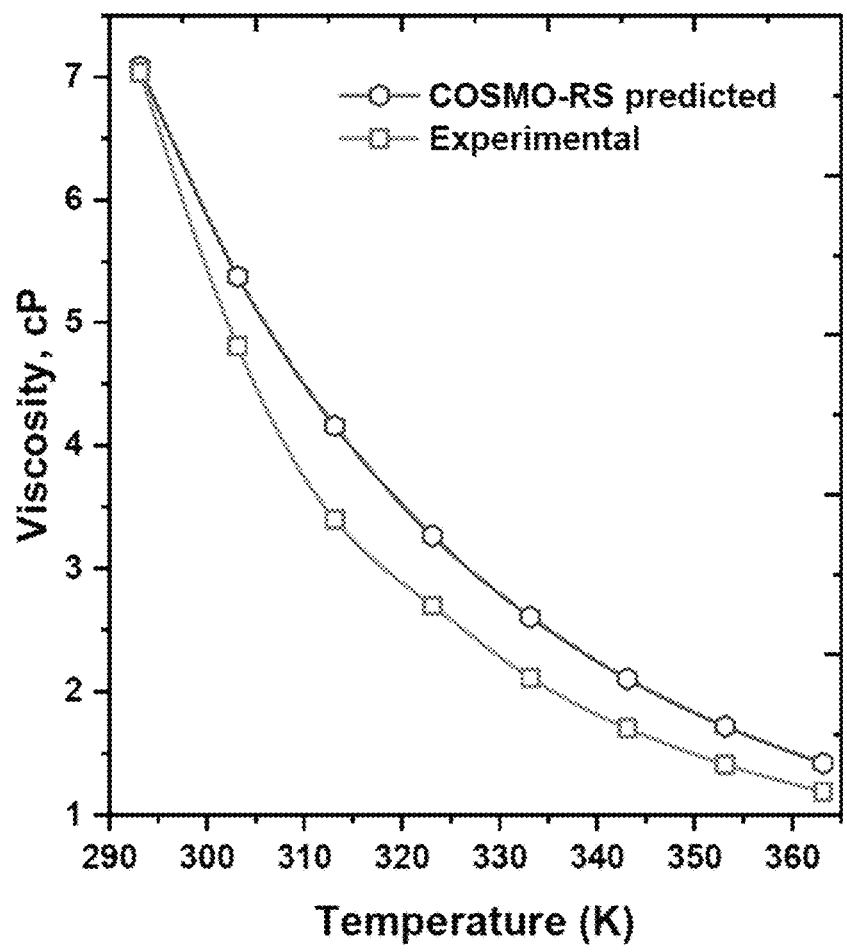
FIG. 17 Experimental and COSMO-RS predicted viscosities of diethylenetriamine at different temperatures.

To confirm these predictions, biomass pretreatment experiments using these solvents were performed in a similar manner as the prior round of screening. Overall, the results indicate that all the poly and diamines were effective solvents. However, an examination of the experimental averages of lignin removal suggest that the polyamines do not actually have the highest lignin extraction capacity (66.1%-79.2%), but rather the diamines (74.1%-85.8%) (FIG. 6). This is not completely unexpected as both spermine and spermidine have a higher viscosity (η) than the diamines (Table 4). Increases in a solvent's viscosity can limit effective mass transfer, which is known to have a negative effect on a pretreatment solvent's dissolution power.[42-45] Therefore, solvents with low $H^E$ values should also be cross checked for high viscosity when screening. In addition to viscosity, the basicity and polarity of the solvent is another indicator of their ability to dissolve lignin. For example, 2,2-dimethyl-1,3-propanediamine has a lower viscosity than spermine and spermidine but only extracted a relatively low amount of lignin (32.6%). This is likely due to the lower polarity and basicity of this solvent (see FIG. 16). Therefore, viscosity, polarity and basicity are important parameters to consider when attempting to predict dissolution. Since viscosities do have a notable impact, we demonstrated that we could predict the amine solvent viscosities using the COSMO-RS model and validated the predictions using the available experimental viscosity data for diethylenetriamine (FIG. 17).[46] This means COSMO-RS can be used to predict $H^E$, $\ln(\gamma)$, and η to facilitate identification of good lignin solvents.

TABLE 4

Predicted excess enthalpy, activity coefficient, and viscosity of amines for cellulose by COSMO-RS

| Solvent | $H^E$ (kcal/mol) | $\ln(\gamma)$ | Viscosity, cP |
|---|---|---|---|
| 1,3-diaminopropane | −1.57 | −5.01 | 0.63 |
| 1,4-diaminobutane (Putrescine) | −1.55 | −4.79 | 0.76 |
| 1,5-diaminopentane (Cadaverine) | −1.56 | −4.63 | 0.89 |
| 1,2-diaminopropane | −1.48 | −4.58 | 0.57 |
| Spermine | −1.57 | −4.64 | 6.82 |
| Spermidine | −1.55 | −4.60 | 2.26 |
| 2,2-dimethyl-1,3-propanediamine | −0.88 | −2.13 | 0.50 |
| Ethylenediamine | −1.46 | −4.84 | 0.54 |
| Diethylenetriamine | −1.42 | −4.50 | 1.42 |
| Pentylamine | 0.07 | −0.04 | 0.65 |
| Aniline | −1.43 | −3.04 | 0.37 |
| 2-ethoxy Ethanol | −0.07 | −0.32 | 1.47 |
| 2-pyrolidone | −0.54 | −2.25 | 0.78 |
| Trimethyl phosphate | −0.29 | −0.92 | 0.63 |
| Furfuryl alcohol | 0.01 | −0.12 | 1.51 |
| Guaiacol | 0.01 | −0.08 | 3.77 |
| Benzyl alcohol | 0.03 | 0.01 | 1.60 |
| Furfural | 0.01 | −0.21 | 0.64 |
| Isobutyl acetate | −0.11 | −0.05 | 0.36 |
| Dipropylene glycol | 0.00 | −0.06 | 8.27 |

Using these COSMO-RS-predicted quantities, three different lignin solubility prediction models (linear and non-linear; equations 1-3) were developed for the amines and then validated. To develop a predictive model, the parameters excess enthalpy (correlated to the interactions), activity coefficient (related to the dissolution capability), viscosity (associated with the mass transfer rate), and the dissociation constant ($pK_a$) related to the strength of acid/base were considered. The following equations were developed to predict the dissolution of lignin, but excluded pentylamine, which was used to validate the models.

Non-linear model 1: (1)

$$\text{Lignin } sol. (\%) = b_0 + \left(b_1 \times \exp(H^E)\right) + \left(\frac{b_2}{\ln(\gamma)}\right) + (b_3 \times \eta) + (b_4 \times pK_a)$$

$b_0 = 210.65; b_1 = -34.41; b_2 = 92.46;$ $b_3 = -3.72;$ and $b_4 = -9$

Non-linear model 2: (2)

$$\text{Lignin } sol. (\%) = b_0 + \left(b_1 \times \exp(H^E)\right) + \left(\frac{b_2}{\ln(\gamma)}\right) + (b_3 \times \eta)$$

$b_0 = 130.33; b_1 = -41.31; b_2 = 124.76;$ and $b_3 = -4.96$

Linear model 3:  (3)

$$\text{Lignin sol. (\%)} = b_0 + (b_1 \times H^E) + (b_2 \times \ln(\gamma)) + (b_3 \times \eta) + (b_4 \times pK_a)$$

$$b_0 = 89.24; b_1 = -45.63; b_2 = 34.23;$$

$$b_3 = -2.55; \text{ and } b_4 = -8.46$$

Here, the $b_0$, $b_1$, $b_2$, $b_3$, and $b_4$ are the fit coefficients (i.e., constants).

Figure 7:
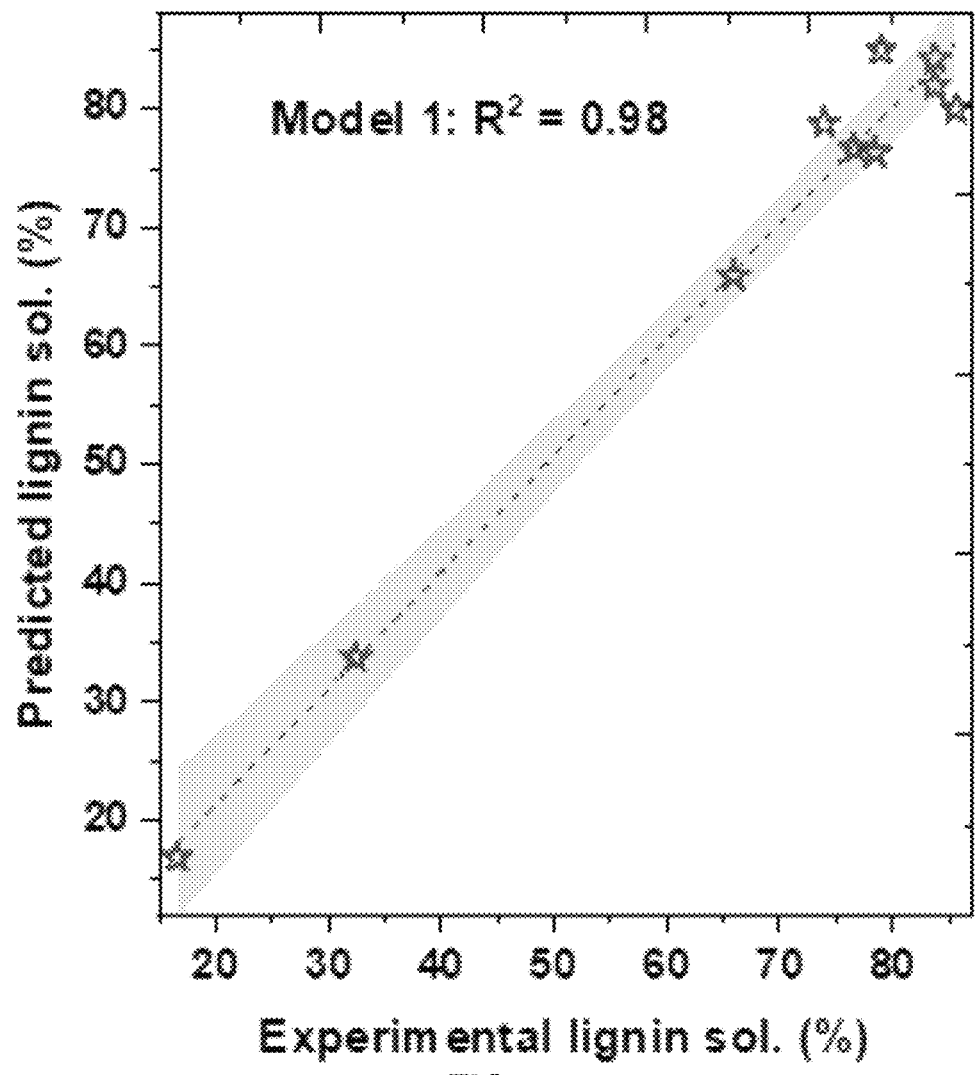
FIG. 7 Experimental data and COSMO-RS-based model 1 predicted lignin solubility for amines with 95% confidence error band.
Figure 18:
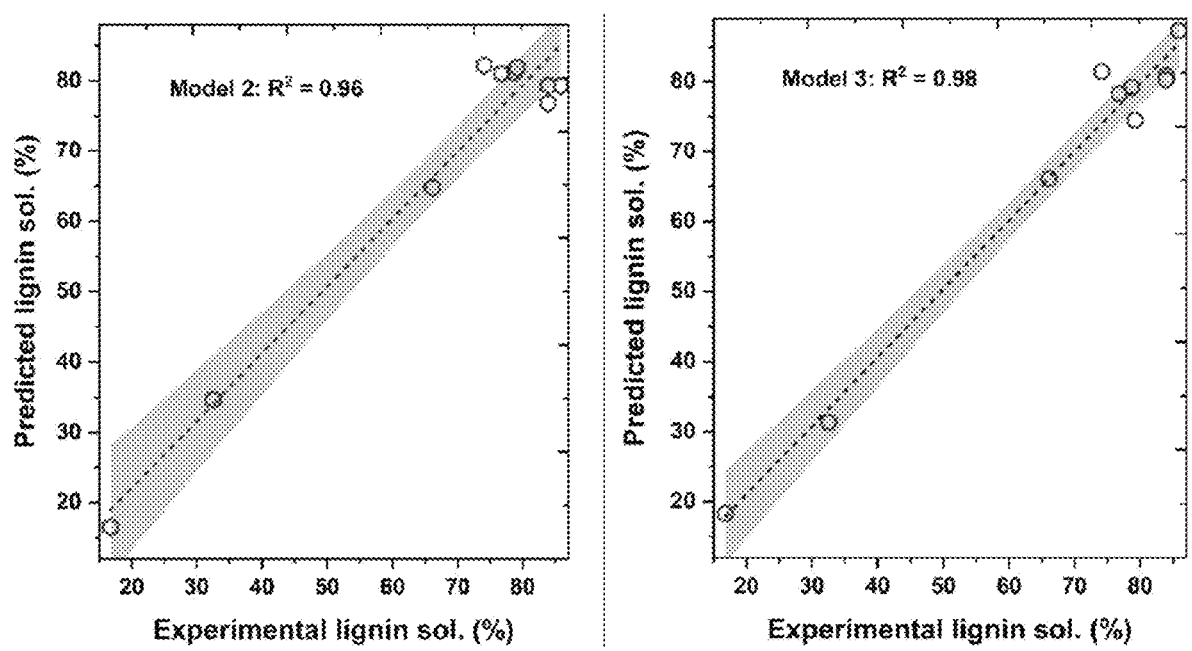
FIG. 18 Experimental and COSMO-RS-based developed models 2 & 3 predicted lignin solubility for amines with 95% confidence error band.

Experimental and predicted lignin solubility for amines based on these models are shown in FIG. 7 (model 1) and FIG. 18 (models 2 and 3). To assess the potential performance of the developed model equations, they were used to predict the solubility of lignin for pentylamine, which was excluded from the original training set. The predicted lignin solubility for models 1, 2, and 3 is 60.2%, 58.9%, and 53.1%, respectively while the experimental lignin solubility in pentylamine is 66.7±3.4%. Further, the predictive models were also evaluated with lignin solubility data from the literature where *Miscanthus* biomass was pretreated with ethylenediamine at higher temperature (180° C.).[47] The experimental lignin solubility was reported as ~71±4%, while the predicted solubility for models 1, 2, and 3 is 65.1%, 53.5%, and 96.1%, respectively. These data indicate that the non-linear model (1) predicts the lignin solubility more accurately than the linear models. This reveals that the relationship between the solvent type and lignin dissolution capacity (within the realm of biomass pretreatment) is not a simple linear relationship. When factors such as mass transfer and chemical reactivity are coupled, non-linear relationships have been more suitable at describing the experimental results. However, these developed lignin solubilities non-linear model could be applicable for amines only when $H^E \leq 0.2$ and $\ln(\gamma) \leq -0.75$.

Figure 8:
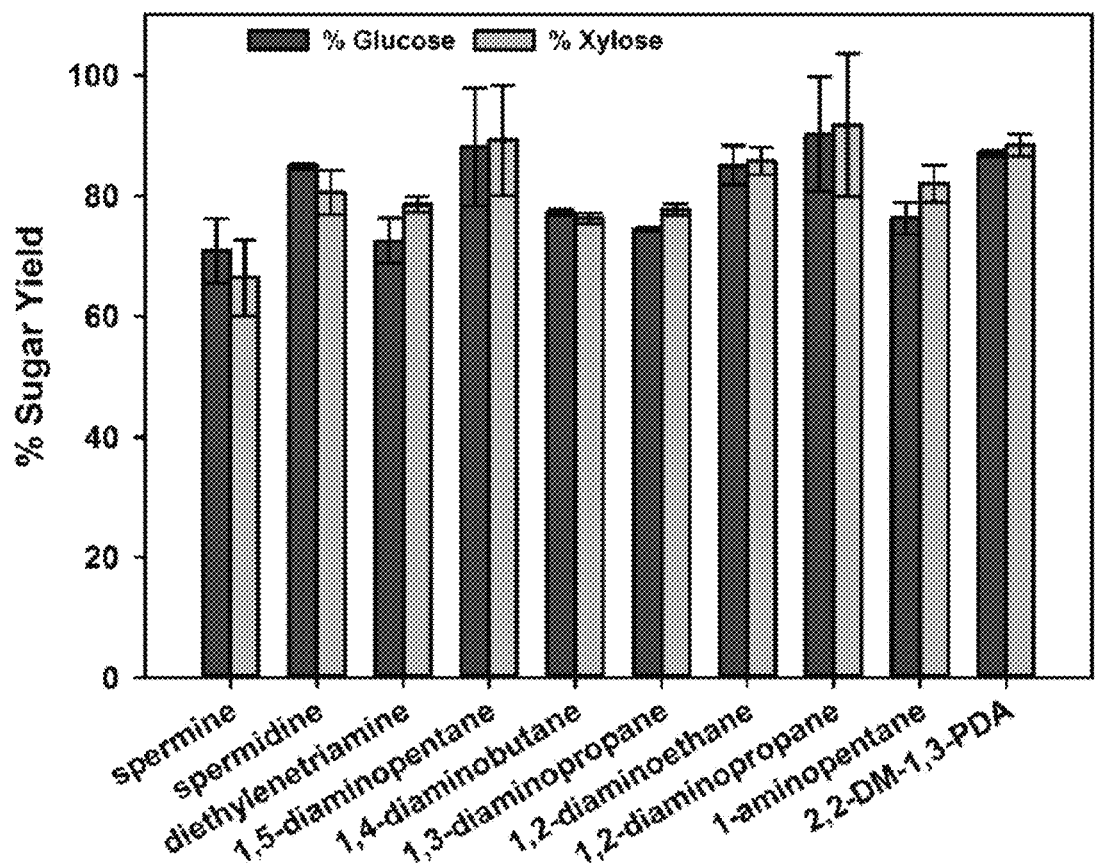
FIG. 8 Glucose and xylose yields after enzymatic hydrolysis of pretreated sorghum with amines.
Figure 19:
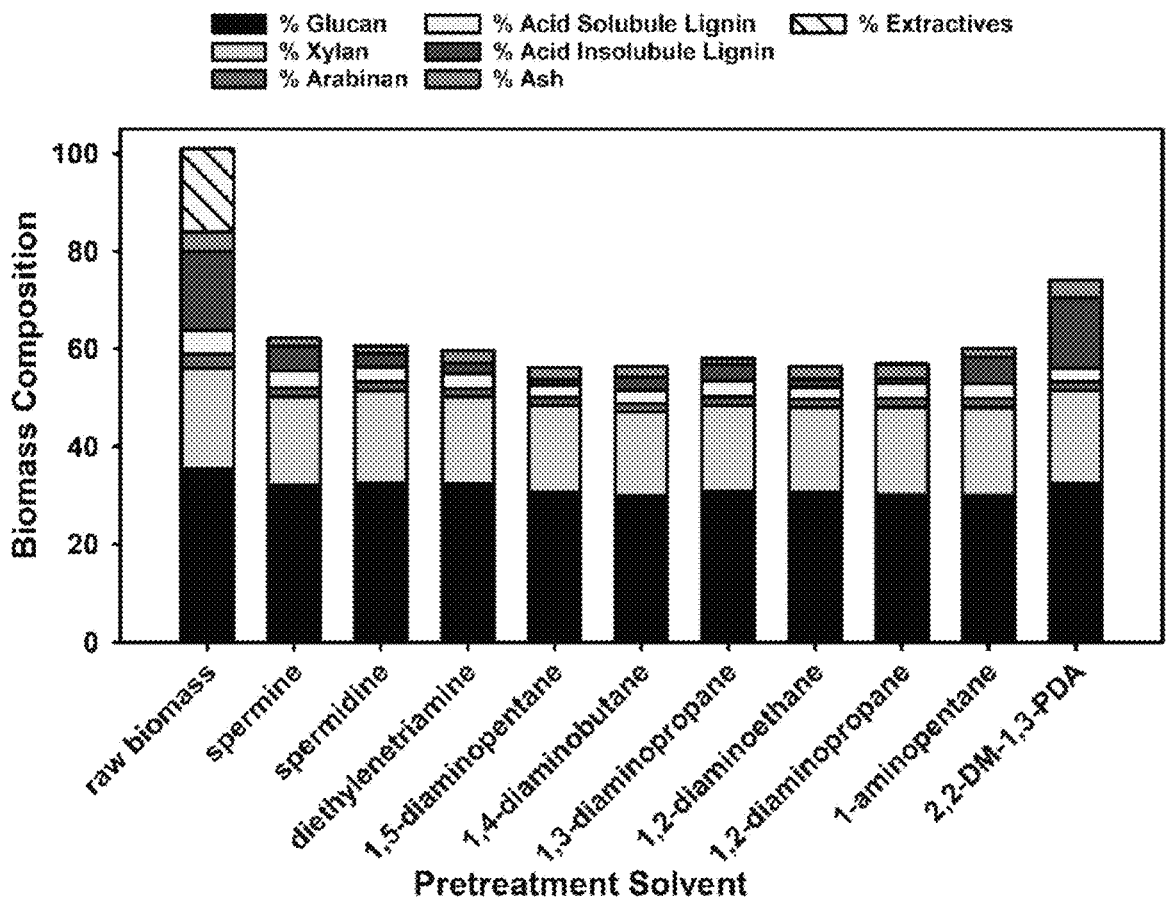
FIG. 19 Biomass yield and composition after pretreatment of sorghum with the amines. The composition of the untreated "raw biomass" is also displayed.
Figure 20:
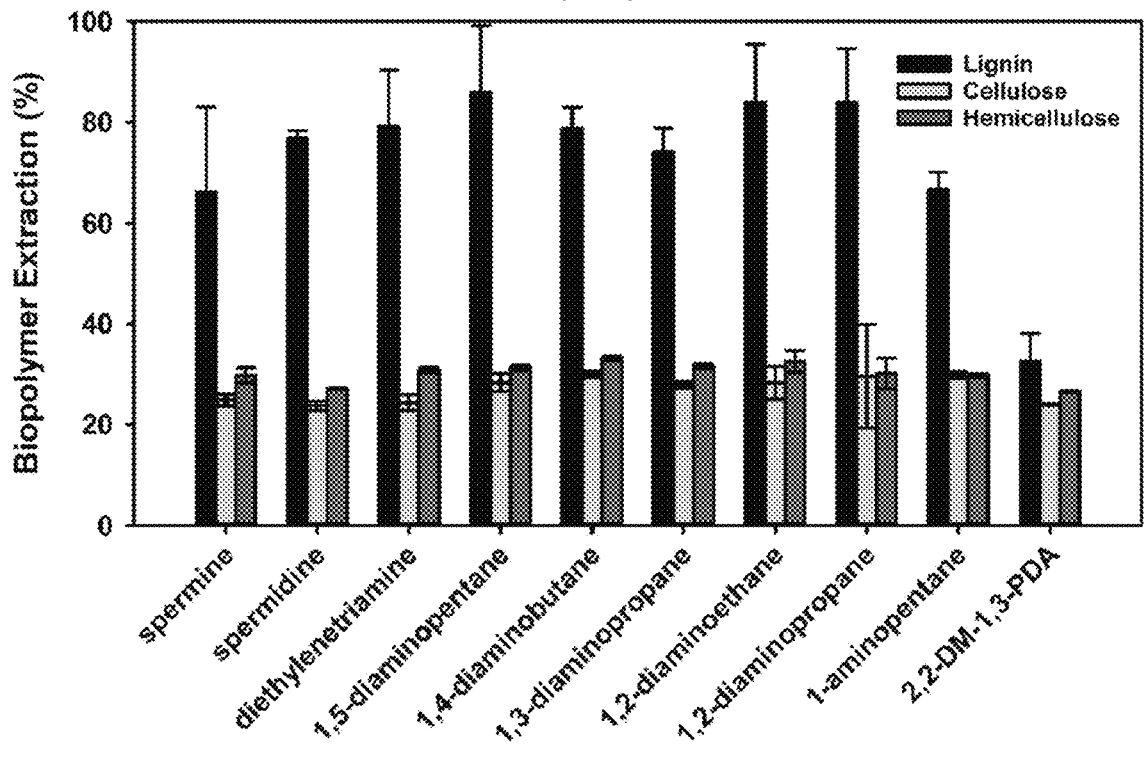
FIG. 20 Amount of each biopolymer (lignin, cellulose and hemicellulose) that was removed during pretreatment and solvent recovery.

2.3. Pretreatment with Amines and Enzymatic Saccharification of Residual Biomass As mentioned earlier, high lignin extraction has been directly correlated with an increase in enzymatic saccharification efficiency of pretreated lignocellulose. Therefore, we tested whether this correlation also holds for biomass pretreated with the new set of polyamines. Typically, efforts to extract lignin from biomass are not completely selective and some portion of polysaccharides are also extracted, so it is important to measure the solid recovery and composition post-pretreatment in order to fully understand the extent of this non-selective extraction and its impact on biomass deconstruction. For the set of amines studied, the solid recovery after pretreatment ranged from 61.5%-68.1% (FIG. 19). The composition of the residual biomass was relatively similar across the different pretreatments, with an average loss of 27.1±2.3% cellulose and 30.2±1.9% hemicellulose (xylan and arabinan) during pretreatment (FIGS. 19-20). In many cases, lignin extraction is accompanied by some extent of hemicellulose/cellulose removal, so these results are not surprising. In an actual biorefinery, these extracted polysaccharides would be returned to the saccharification reaction after solvent recovery. Nevertheless, all amines investigated in this study afforded >70% glucose yields, with the highest glucose yield of ~90% (FIG. 8). The glucose yields with these amines could be organized in the following order: 1,2-diaminopropane>1,5-diaminopentane>2,2-dimethyl-1,3-propanediamine>ethylenediamine>spermidine>1,4-diaminobutane>pentylamine>1,3-diaminopropane>diethylenetriamine>spermine. Similarly, >65% xylose yields were attained with these amines, with a highest xylose yield of ~92% obtained also for 1,2-diaminopropane. The xylose yields followed the similar order as of glucose (FIG. 8).

The efficiency of sugar release for most amines was as expected based on the extent of lignin removal. Interestingly, 2,2-dimethyl-1,3-propanediamine extracted relatively low amounts of lignin (32.6%) but still permitted high sugar yields. This was very unexpected and does not fit well with previously reported studies of pretreatment solvents that selectively extract lignin. However, while lignin extraction can drive increases in saccharification efficiency, it is not the only factor that influences the release of sugars from biomass. Lignocellulose is complicated, and there are many possible outcomes of solvent-based pretreatment that can impact enzymatic sugar release, such polysaccharide extraction, or modification of macrostructure of biomass to increase the accessible surface area for enzymatic hydrolysis, etc. This is an interesting observation and suggests that amines are potentially acting to reduce the recalcitrance to enzymatic digestion by other mechanisms than lignin dissolution.

2.4. Cellulose Structure and Allomorphs

Figure 9:
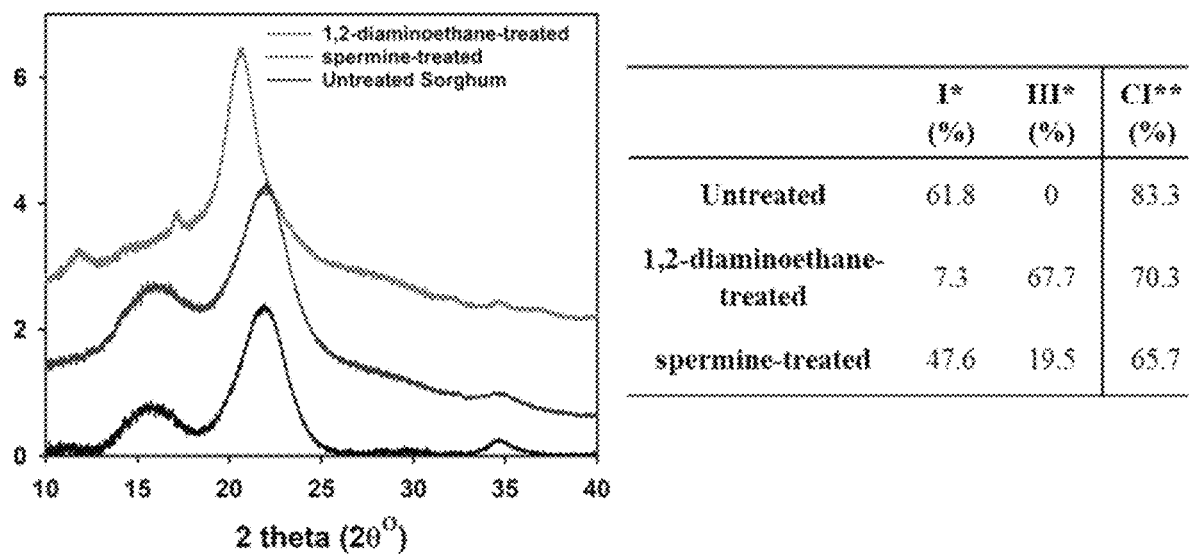
FIG. 9 X-ray diffraction profiles for untreated and treated sorghum including the relative percentage of each polymorph and crystallinity index (*measured by method or Segal et. al).
Figure 21:
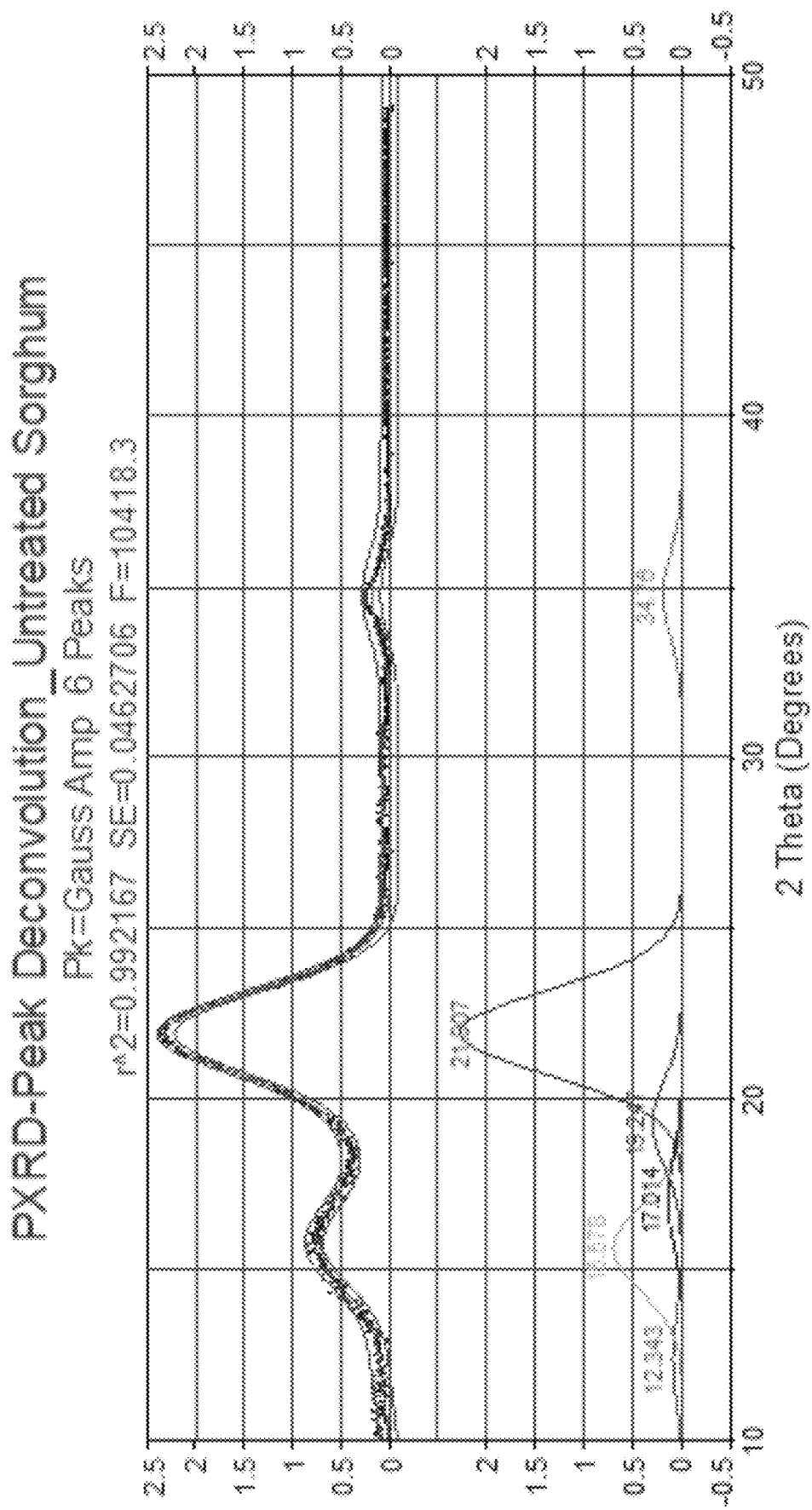
FIG. 21 X-ray diffraction profiles for untreated sorghum along with results from peak deconvolution.
Figure 22:
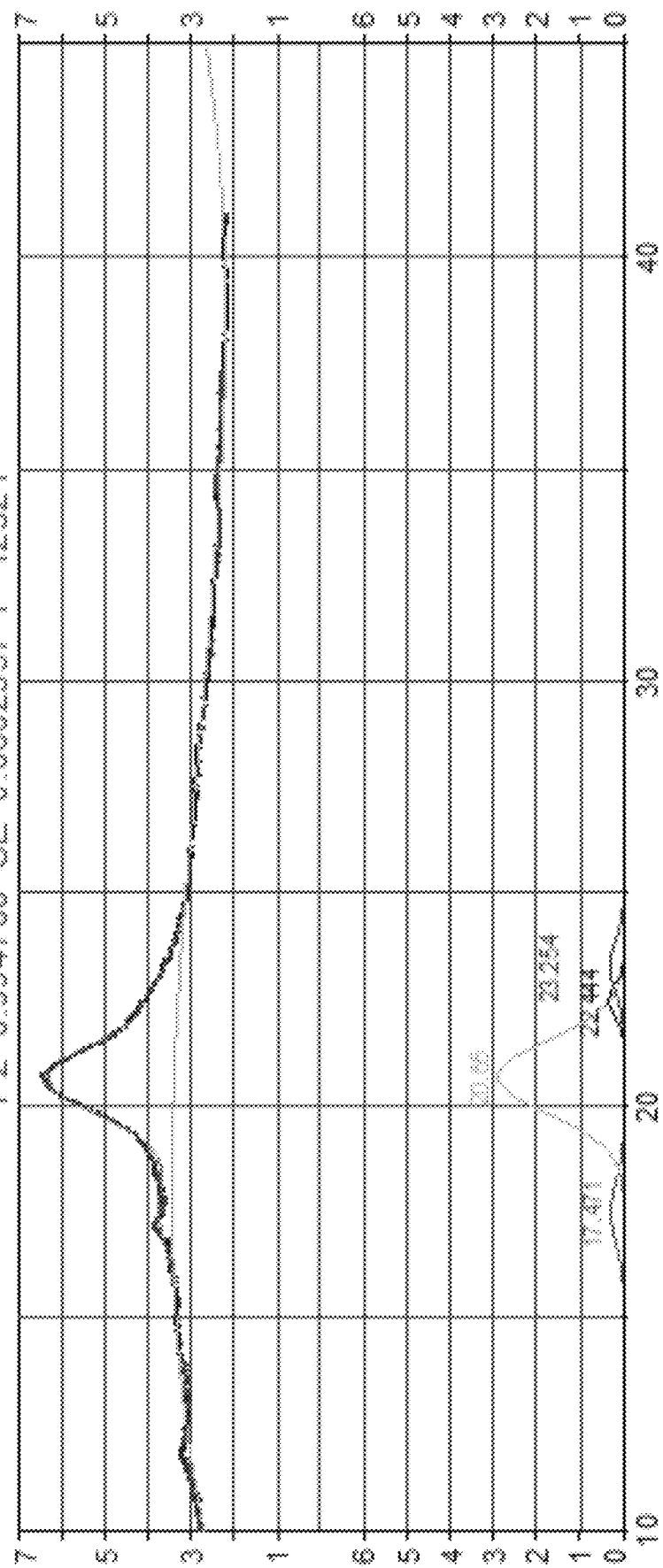
FIG. 22 X-ray diffraction profiles for ethylenediamine-treated sorghum along with results from peak deconvolution.
Figure 23:
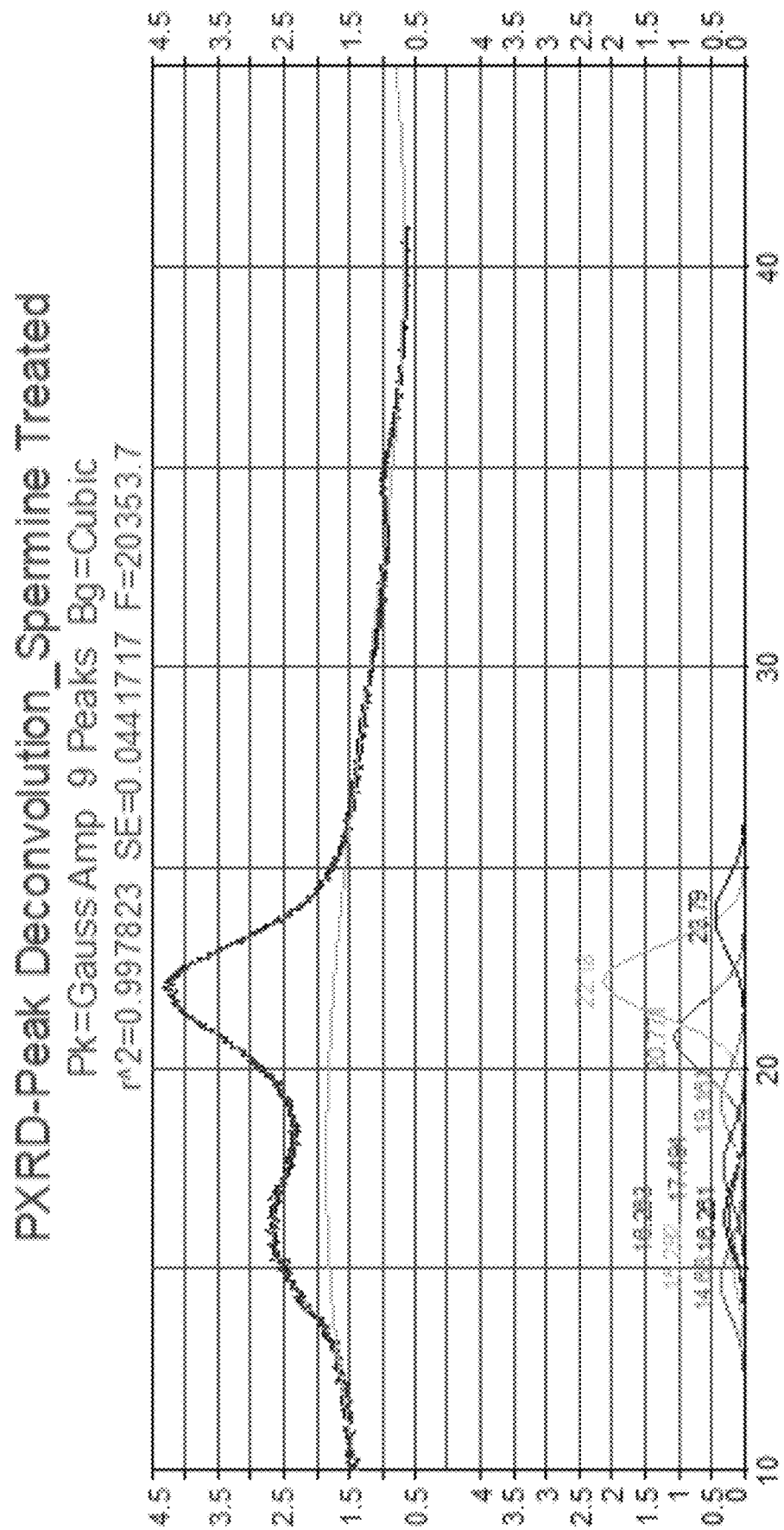
FIG. 23 X-ray diffraction profiles for spermine-treated sorghum along with results from peak deconvolution.
Figure 24:
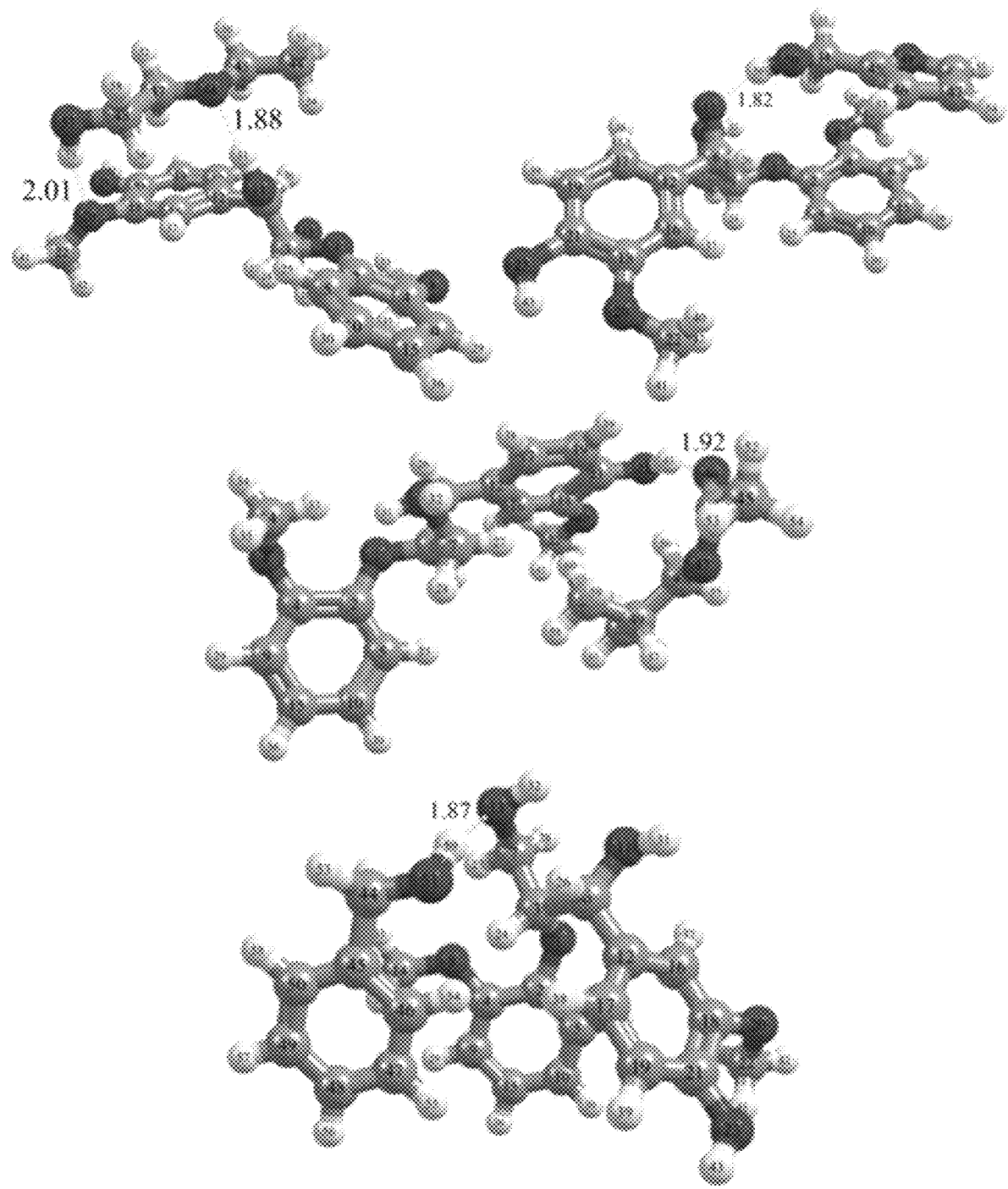
FIG. 24 Optimized geometries for lignin GGE-organic solvents (a) 2-ethoxyethanol, (b) furfuryl alcohol, (c) isobutyl acetate, and (d) benzyl alcohol. The H-bonds are indicated by dotted lines, the bond lengths are in Angstrom (Å) and given with corresponding atom numbers. The color scheme used for different atoms is C (gray), O (red), and H (white), respectively.
Figure 25:
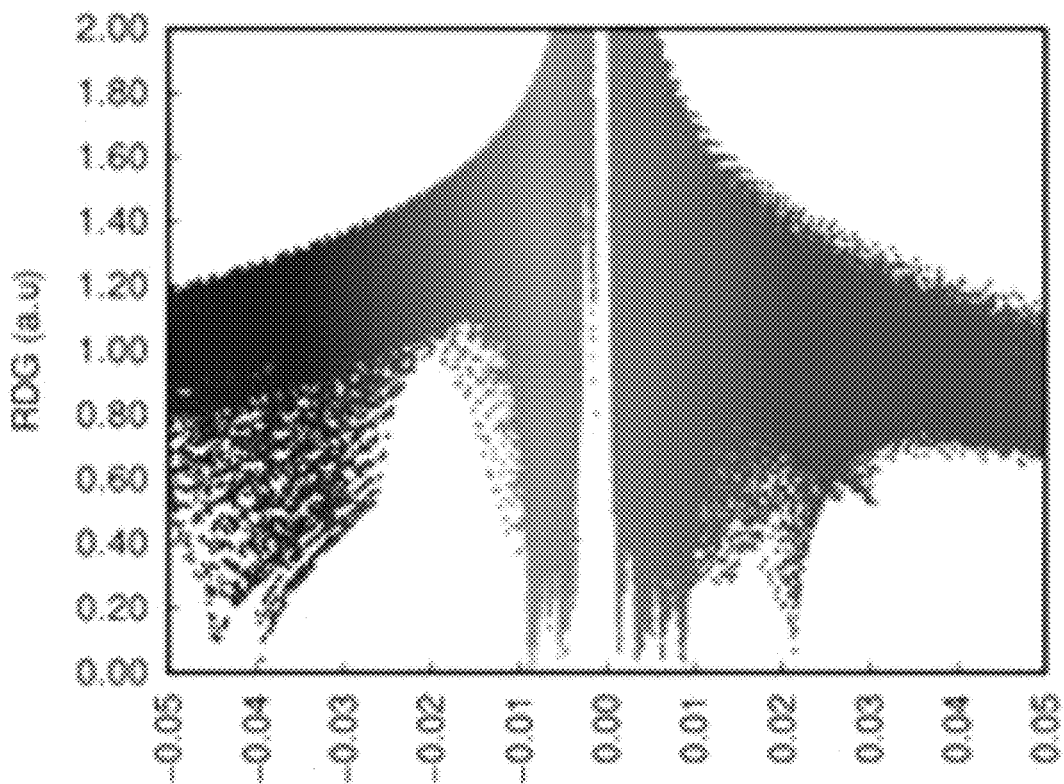
FIG. 25 RDG scatter plots (isovalue 0.5 a.u.) of lignin-amine/organic solvents. The RDG scatters are colored on a blue-green-red scale according to values of sign($\lambda_2$)$\rho(r)$, ranging from −0.045 to 0.025. Blue indicates strong attractive interactions, green indicates the vdW interaction, and red indicated steric repulsions.
Figure 25:
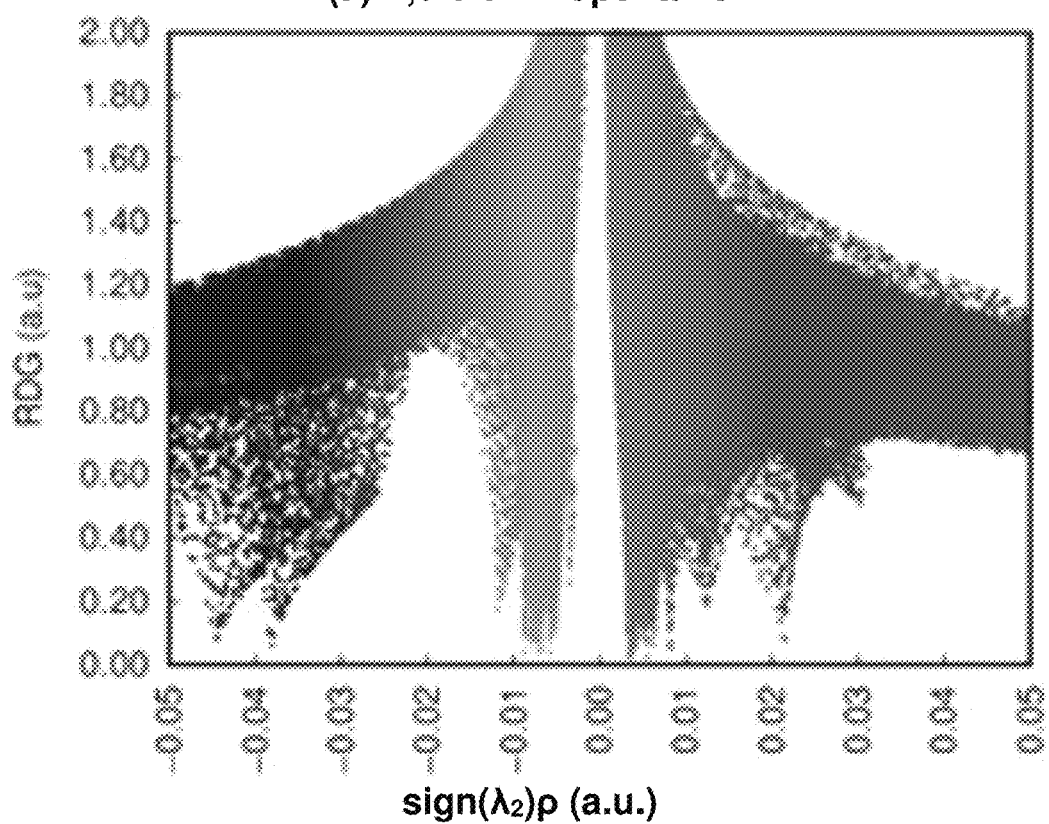
Figure 25:
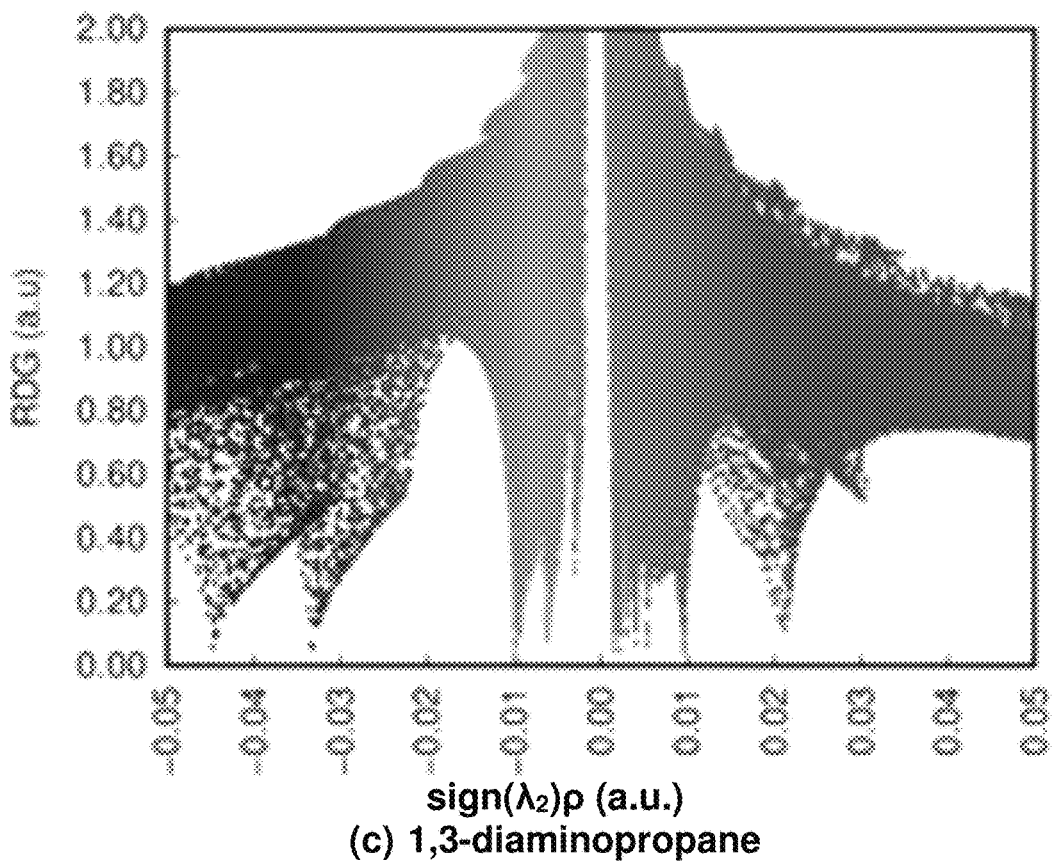
Figure 25:
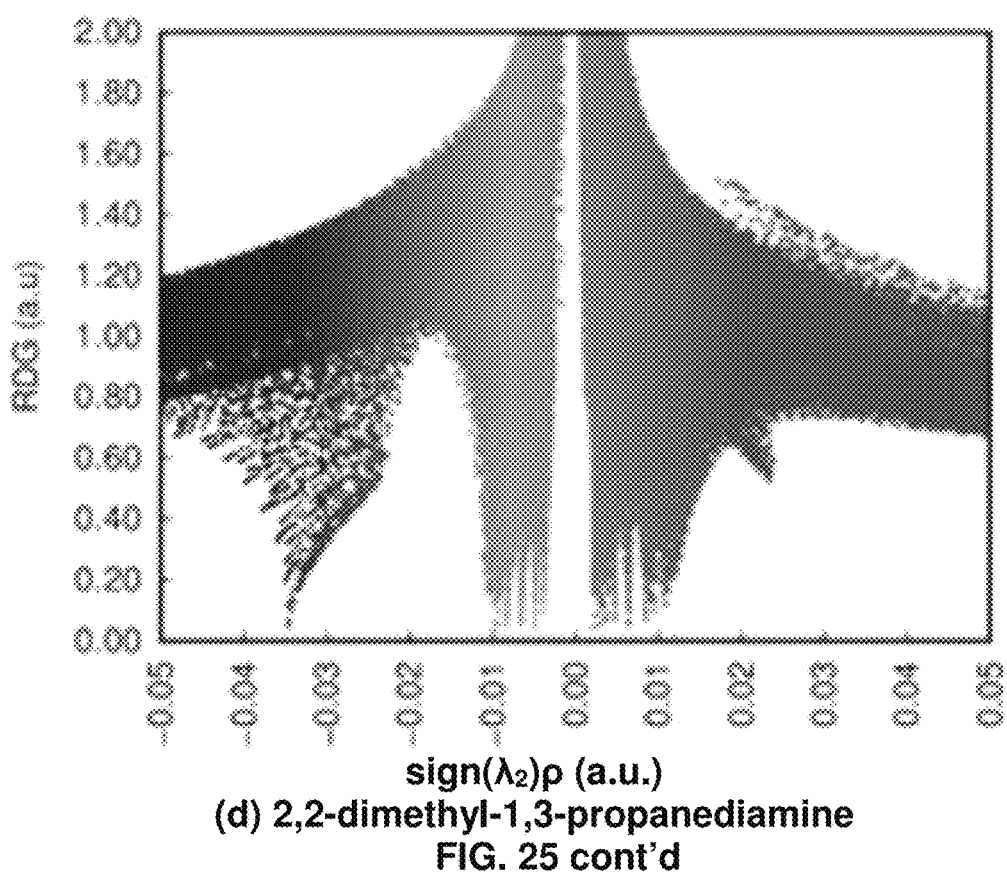
Figure 25:
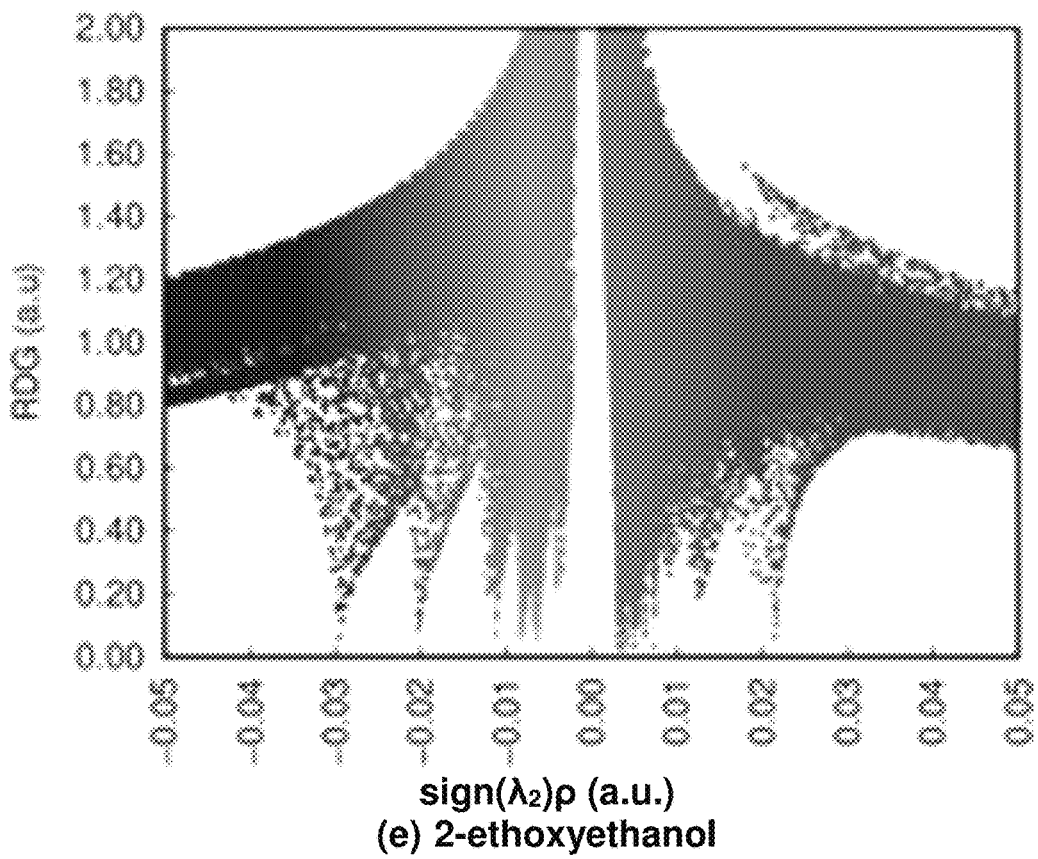
Figure 25:
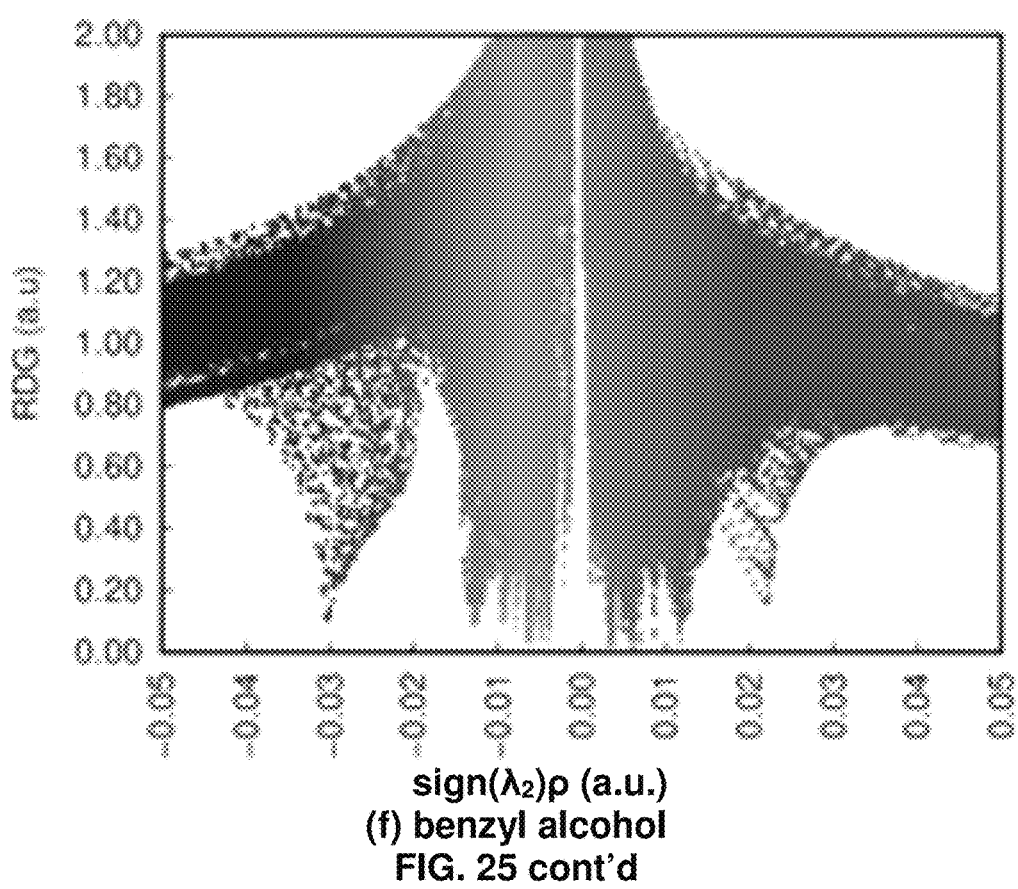
Figure 26:
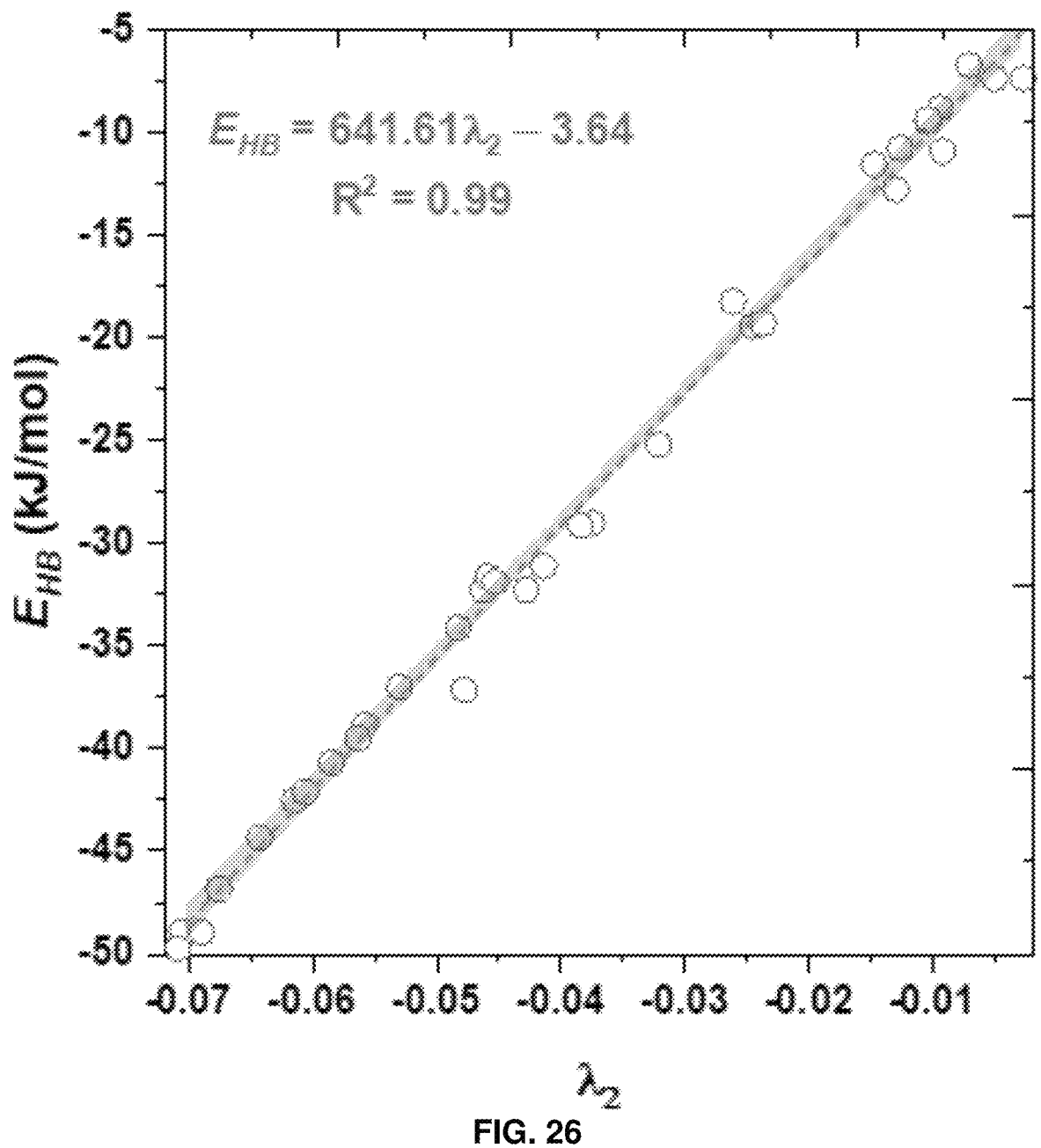
FIG. 26 Correlation between QTAIM-based Hessian second eigenvalue ($\lambda_2$) and H-bonding energies ($E_{HB}$) of lignin-amine/organic solvent systems.
Figure 27:
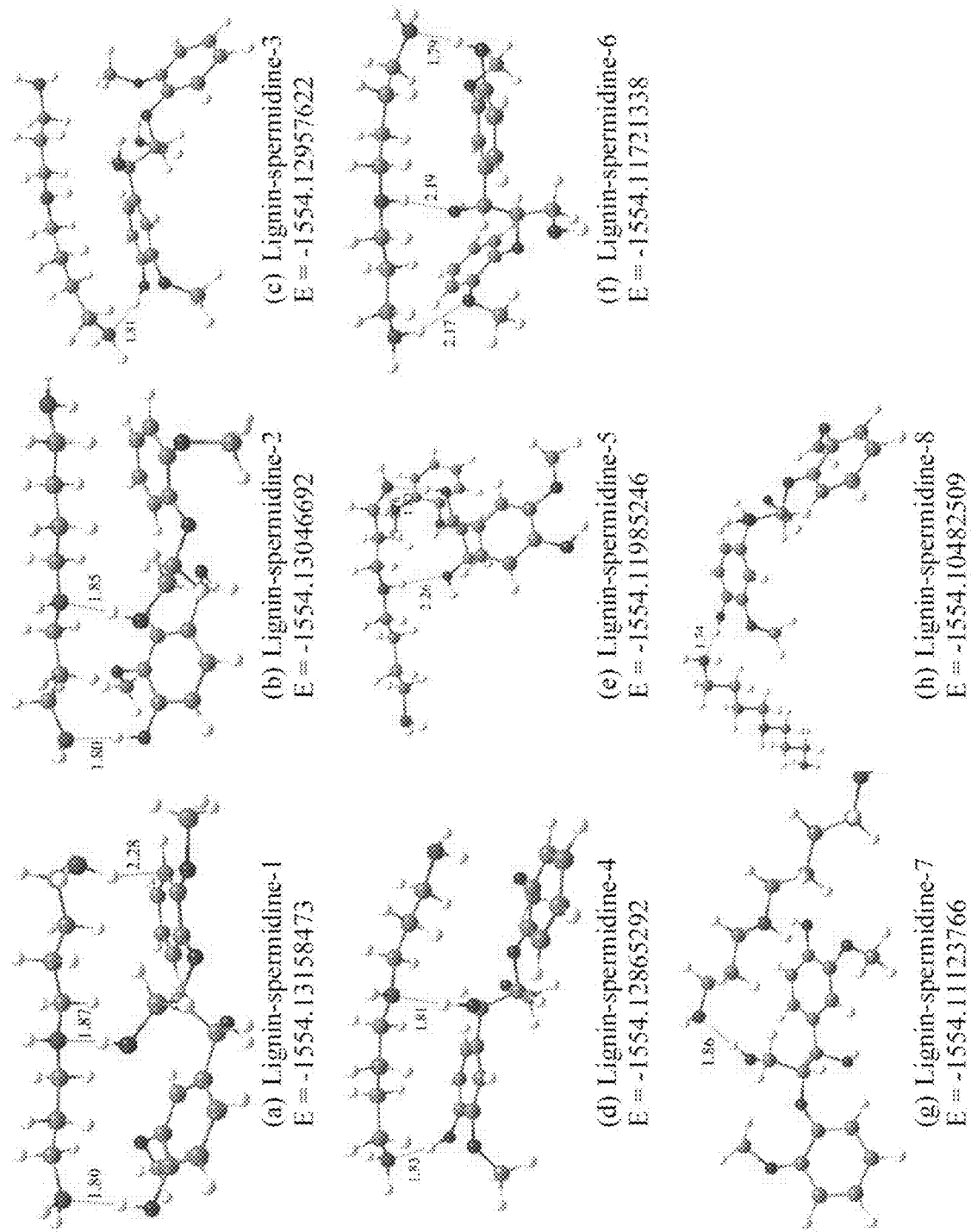
FIG. 27: The optimized configurations of lignin-spermidine-n (n=1-8) at B3LYP-GD3BJ/6-311+g(d,p) level. The hydrogen bonds are indicated by dashed lines and bond distances are given in Å.
Figure 28:
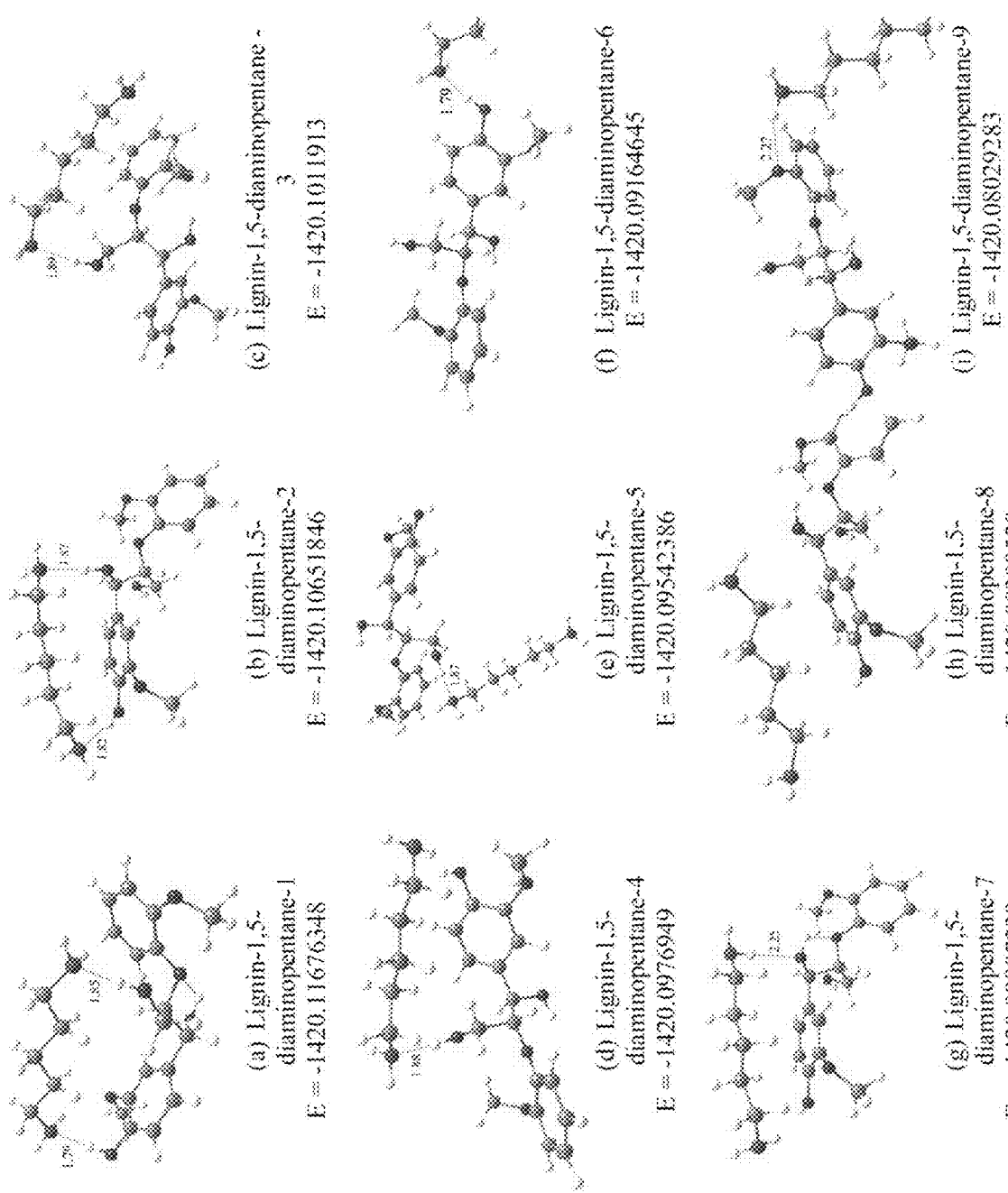
FIG. 28: The optimized configurations of lignin-1,5-diaminopentane-n (n=1-9) at B3LYP-GD3BJ/6-311+g(d,p) level. The hydrogen bonds are indicated by dashed lines and bond distances are given in A.
Figure 29:
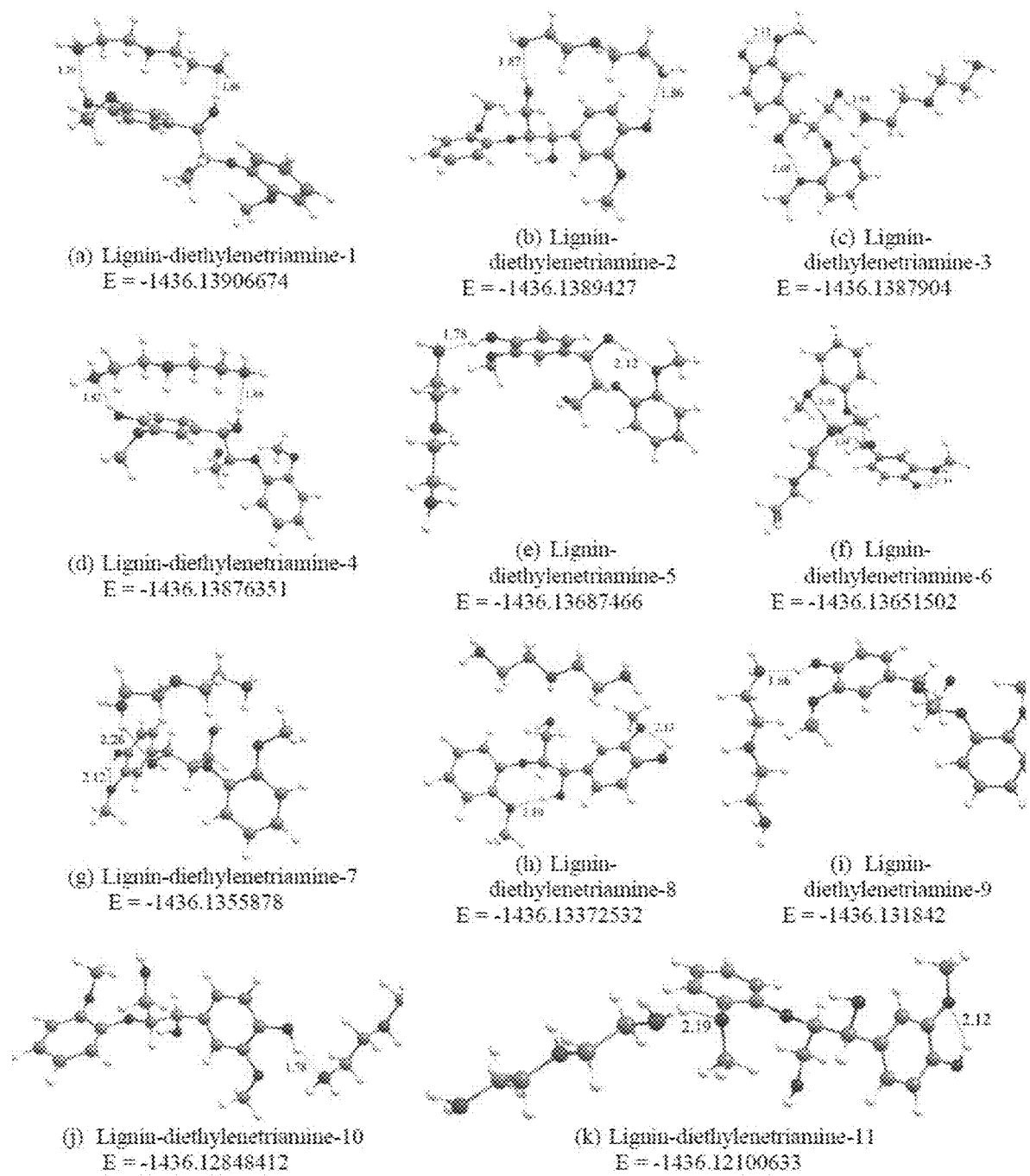
FIG. 29: The optimized configurations of lignin-diethylenetriamine-n (n=1-11) at B3LYP-GD3BJ/6-311+g(d,p) level. The hydrogen bonds are indicated by dashed lines and bond distances are given in A.
Figure 30:
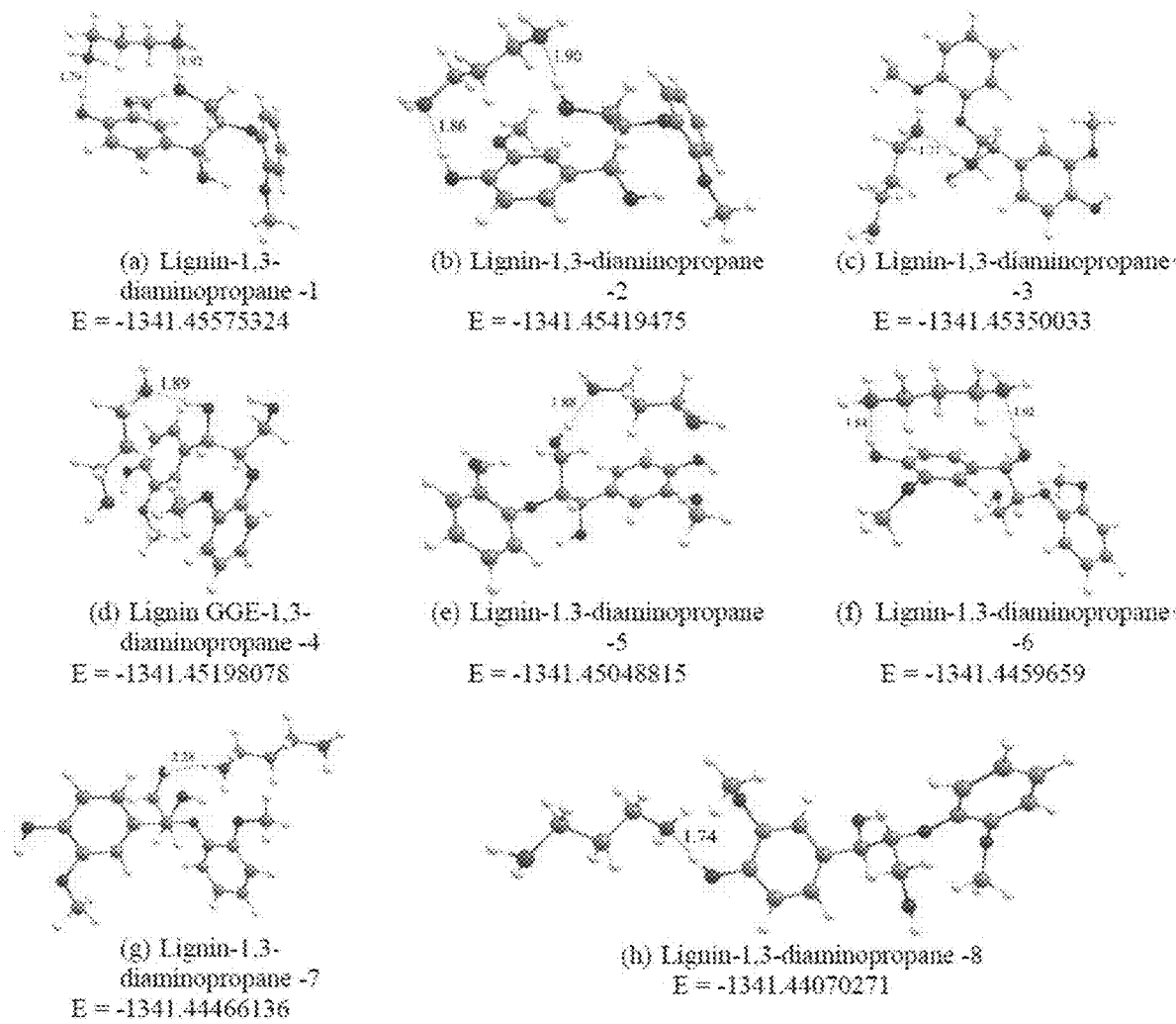
FIG. 30: The optimized configurations of lignin-1,3-diaminopropane-n (n=1-8) at B3LYP-GD3BJ/6-311+g(d,p) level. The hydrogen bonds are indicated by dashed lines and bond distances are given in A.
Figure 31:
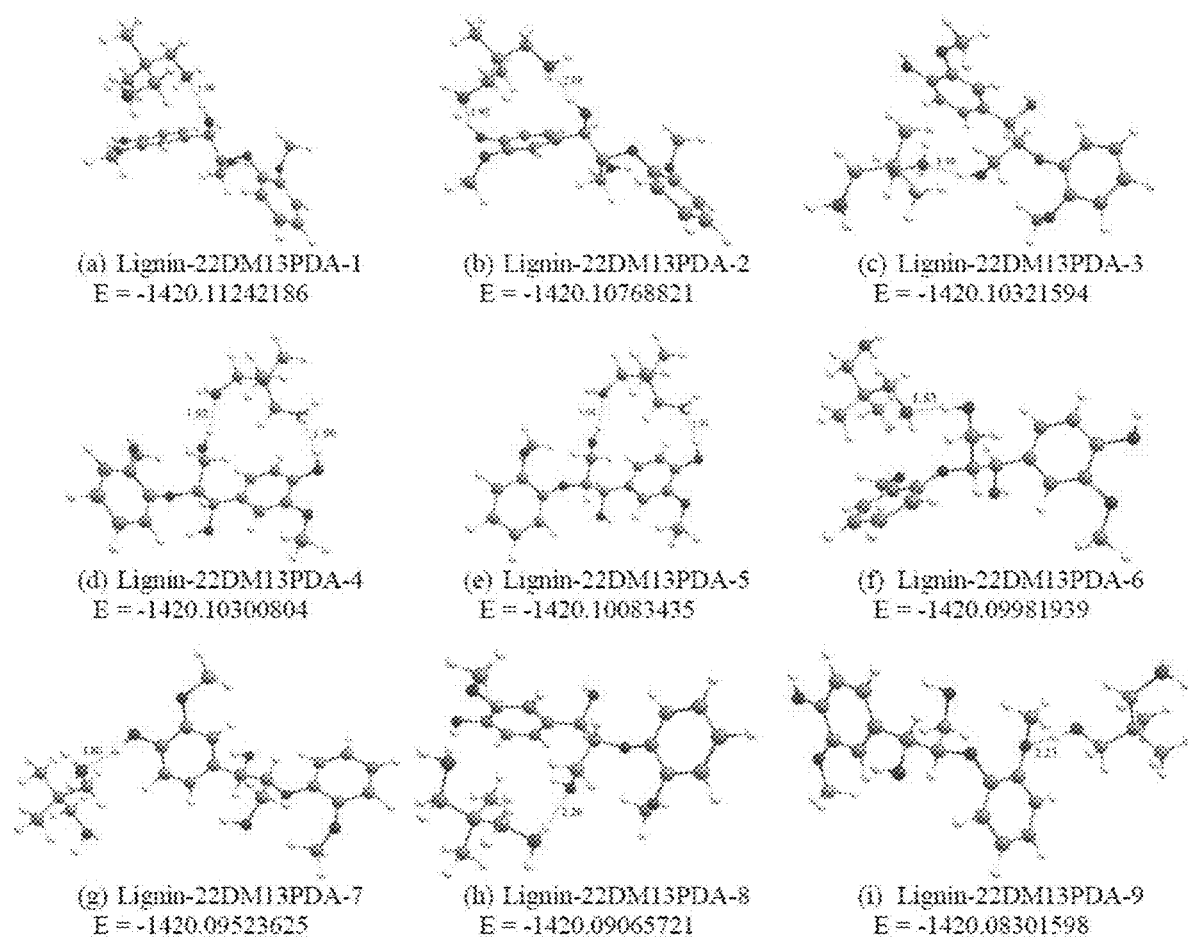
FIG. 31: The optimized configurations of lignin-2,2-dimethyl-1,3-propanediamine (22DM13PDA)-n (n=1-8) at B3LYP-GD3BJ/6-311+g(d,p) level. The hydrogen bonds are indicated by dashed lines and bond distances are given in Å.
Figure 32:
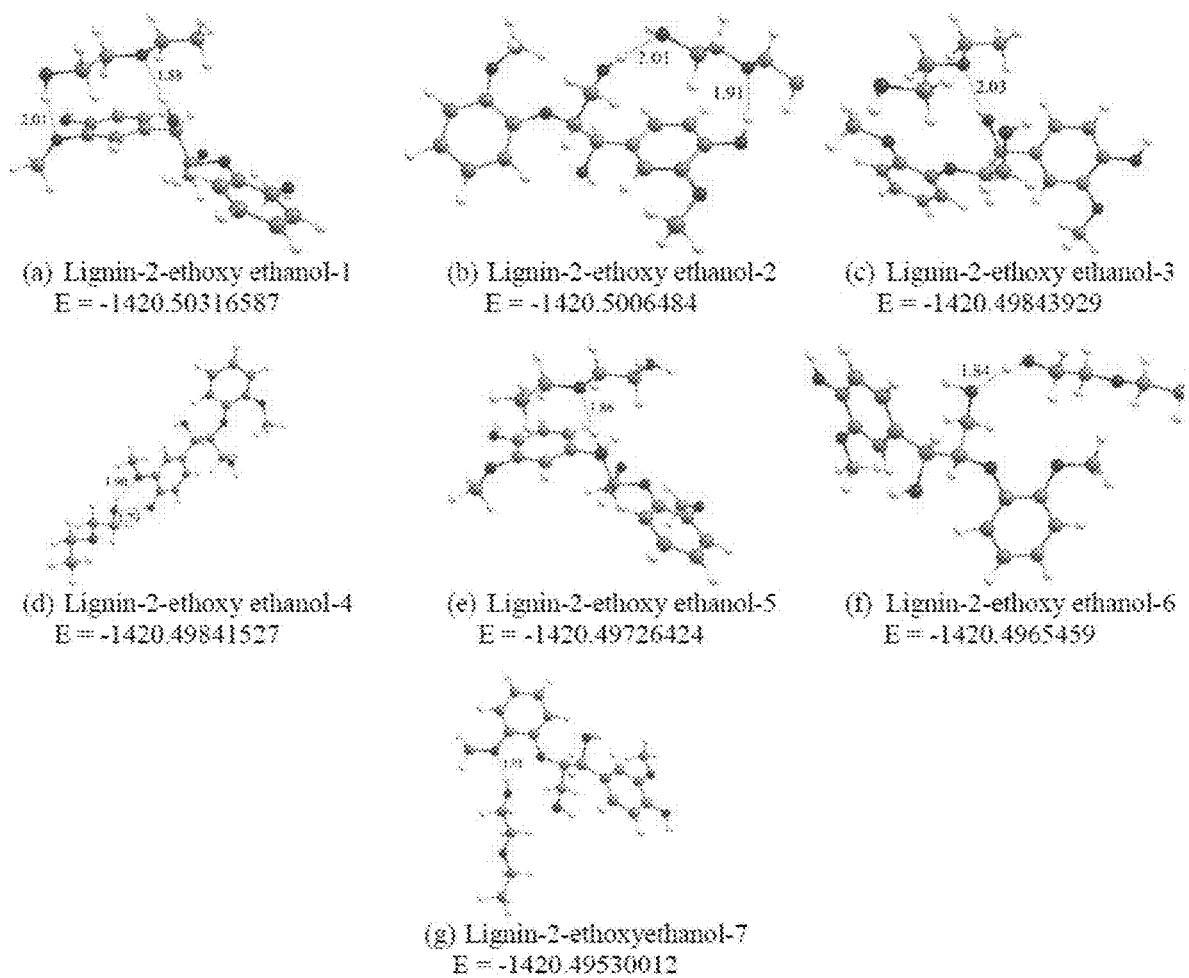
FIG. 32: The optimized configurations of lignin-2-ethoxyethanol-n (n=1-7) at B3LYP-GD3BJ/6-311+g(d,p) level. The hydrogen bonds are indicated by dashed lines and bond distances are given in A.
Figure 33:
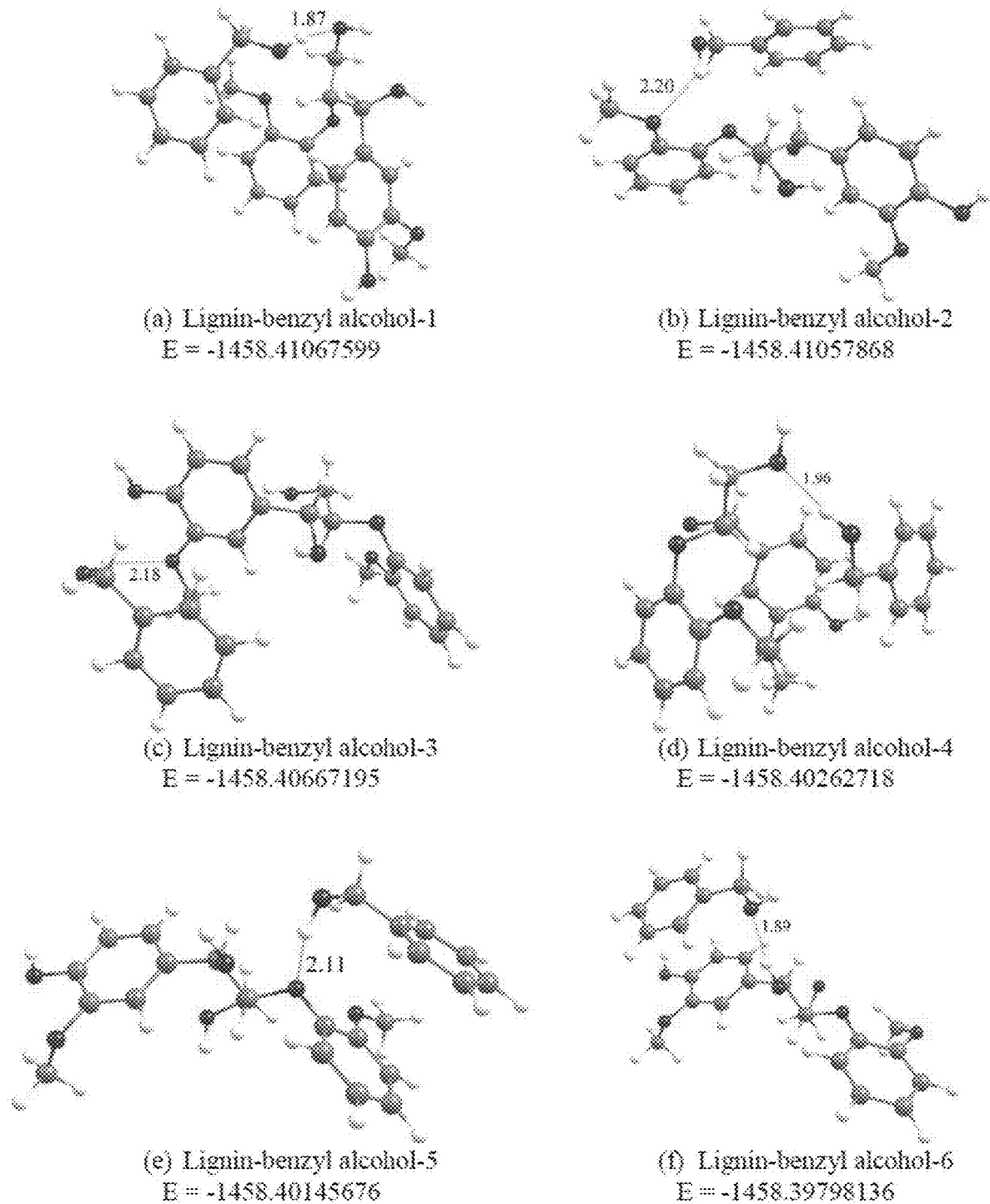
FIG. 33: The optimized configurations of lignin-benzyl alcohol-n (n=1-6) at B3LYP-GD3BJ/6-311+g(d,p) level. The hydrogen bonds are indicated by dashed lines and bond distances are given in A.
Figure 34:
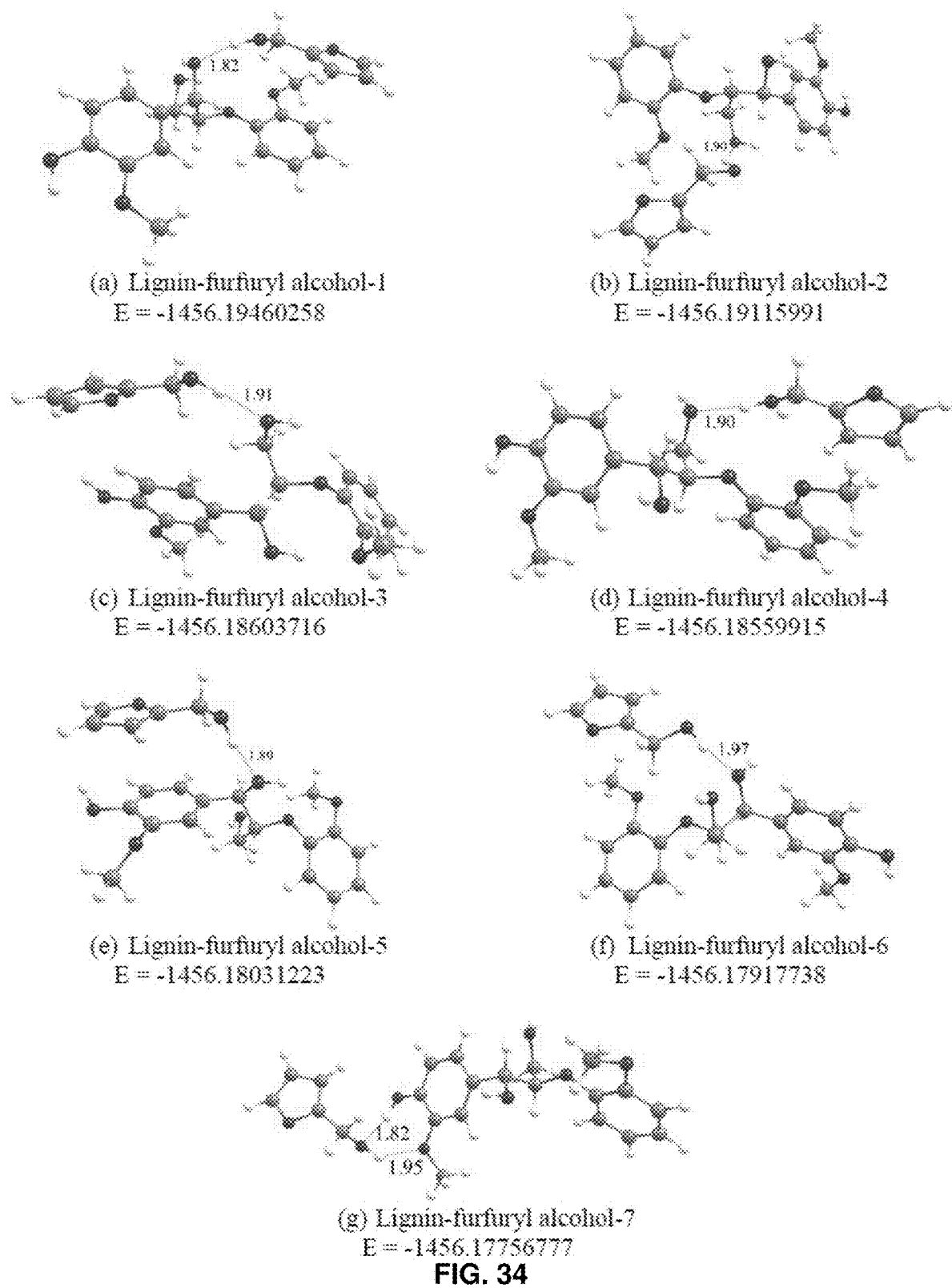
FIG. 34: The optimized configurations of lignin-furfuryl alcohol-n (n=1-7) at B3LYP-GD3BJ/6-311+g(d,p) level. The hydrogen bonds are indicated by dashed lines and bond distances are given in A.
Figure 35:
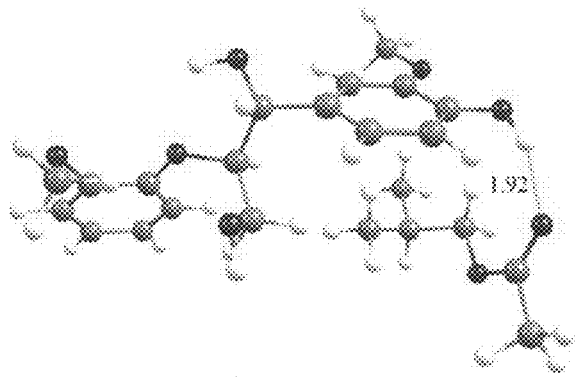
FIG. 35: The optimized configurations of lignin-isobutyl acetate-n (n=1-6) at B3LYP-GD3BJ/6-311+g(d,p) level. The hydrogen bonds are indicated by dashed lines and bond distances are given in Å.
Figure 35:
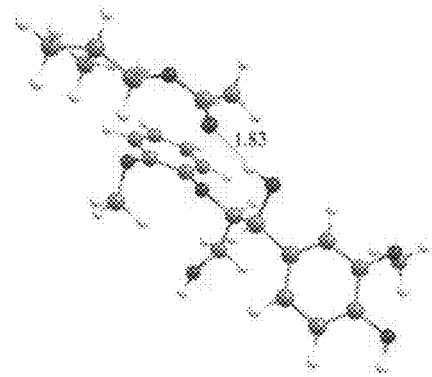
Figure 35:
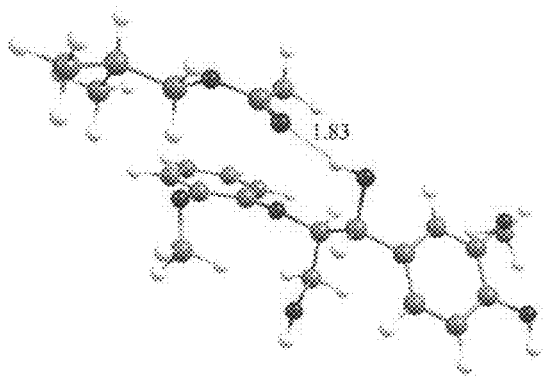
Figure 35:
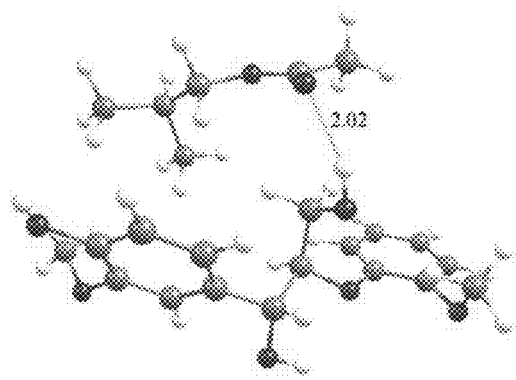
Figure 35:
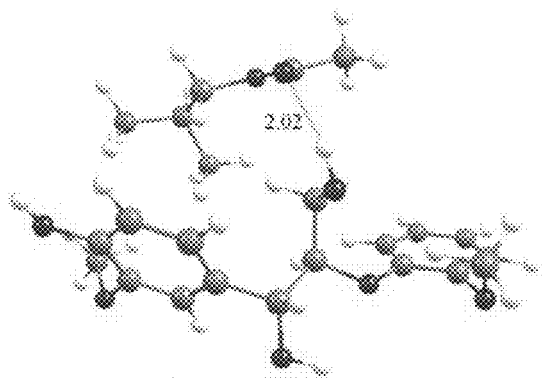
Figure 35:
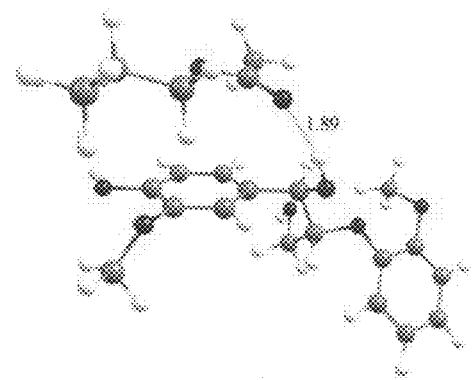

To study the structural changes in the polymers that occur during pretreatment, PXRD was utilized to determine the polymorph of cellulose and the proportions of crystalline and non-crystalline components in the biomass sample. The untreated sorghum displays diffraction patterns characteristic to the cellulose I polymorph, which is typical for native cellulose that is found in untreated lignocellulosic biomass (FIGS. 9 and 21) with a crystallinity content of 83.3%. Note: This is higher than that previously reported for sorghum (~50-55%) due to the different radiation source used in these measurements (Cobalt vs. Copper). Nevertheless, we can compare the results qualitatively to determine the impact of pretreatment on the biomass. When 1,2-diaminoethane was utilized to pretreat the biomass, a change in the polymorph was observed. The identified peaks in the diffractogram match what has been previously reported as cellulose III and depicted a lower crystallinity index (70.3%) (FIGS. 9 and 22). This observation is in line with previous reports associated with amine pretreatment. Qin et. al. showed that using 1,2-diaminoethane (also known as ethylenediamine) resulted in biomass modification to cellulose III especially when high temperatures are used followed by soaking and washing in ethanol (unlike water). On the other hand, the biomass recovered after pretreatment with the polyamine-spermine displayed mixed polymorphism. The diffractogram shows peaks analogous to both cellulose I and III, although the majority of the crystalline peaks are from cellulose I polymorph (FIGS. 9 and 23). Nevertheless, the recovered biomass has the highest amorphous character with a crystallinity index of 65.7%.

The recovered biomass (after pretreatment) was subjected to saccharification and yielded an average sugar (glucose/xylose) of 68.6% and 85.4% for spermine and ethylenediamine respectively. Although ethylenediamine had a slightly higher crystallinity index, it resulted in the higher sugar yields. Therefore the crystallinity index alone is not the sole factor for improving biomass digestibility. In conjunction with polymorph transformation, amine pretreatment can significantly reduce the crystallinity index, which can impact the cellulose digestibility. In their previous work, researchers reveal that ethylenediamine molecules penetrate the hydrophilic edges of the stacked sheets and enlarge cellulose III volume in their (010) direction. These changes have been reported to increase the enzymatic saccharification rate by 5 times, while other studies found that initial rates of digestion were strongly correlated with amorphous content, not the allomorph type.

Although celluloses having a higher amorphous content are typically easy to digest (enzymatically), it is unclear whether the crystallinity index alone gives a direct correlation to the digestibility of a biomass sample. In general, the accessibility of the plant cell-wall to the various exo- and endo-cellulases seems to be the most important factor in determining hydrolysis rate. While enzyme accessibility could be affected by crystallinity, it is also known to be affected by the lignin and hemicellulose contents/distribution, the particle size, and the porosity of the biomass. This is more in line with our observed results where lignin and hemicellulose removal for ethylenediamine were much higher (83.9% and 32.5%) than that of spermine (66.1% and 29.7%). It is well known that lignin plays a more important role than cellulose crystallinity on the digestibility of lignocellulose, and both the chemistry and physical barrier of lignin characteristics can lead to the inhibition of enzymatic hydrolysis. Therefore, this factor (lignin solubilization and removal) remains our main point of optimization for this study.

To better understand the dissolution mechanism of lignin in the molecular solvents, quantum chemical (QC) simulations were performed. QC calculation is a prevailing computational technique for investigating the underlying molecular interactions of solvent/solute systems. These calculations can be used to investigate different types of interactions between solvents and solutes and help researchers to understand which interactions drive a solvent's ability to dissolve a solute. It is computationally difficult to conduct QC calculations with large macromolecules such as polymeric type lignin structure, so to simplify our analysis, we chose a representative lignin dimer, guaiacyl glycerol-p-guaiacyl ether (GGE) as a model molecule since it has the most common β-O-4 monomer-monomer linkage found in lignin. These complex systems can adopt many different conformations, which complicates analysis, so the most stable energy conformer structures of lignin GGE-molecular solvents were obtained for understanding several aspects of their interactions in more detail. According to Boltzmann distribution, the conformers with the lowest energy would stand the maximum proportion of distribution. The lowest energy conformers are used to construct the initial structures for the geometry optimization between lignin-amines and lignin-organic solvents. All of the lignin-amine/organic solvent conformers with relative energies are provided in the supporting information (FIGS. 14-32 and Table 5-13) and the most stable conformers are depicted in FIGS. 9 and 21. All of the optimized conformers show that the ideal interaction site for lignin-amine interaction is the α-OH, γ-OH, and phenol-OH group of lignin. Further, interaction energies, non-covalent interactions, critical bonding topological characteristics, and assessing the strength of the electron donor-acceptor orbital interactions have been performed for only the most stable lowest energy conformers.

TABLE 5

Hydrogen bonds, relative optimized complex energy ($\Delta E_{relative}$), and Fi-SAFT predicted interaction energy (I.E.) between the different conformers of lignin and spermidine.

| Lignin-spermidine | H-bonding | Distance (Å) | $\Delta E_{relative}^{a}$, (kJ/mol) | I. E., (kJ/mol) |
|---|---|---|---|---|
| Conformer 1 | O23-H42 ... N43 | 1.80 | 0.00 | −133.37 |
| | O13-H32 ... N47 | 1.87 | | |
| | N52-H64 ... O8 | 2.28 | | |
| Conformer 2 | O23-H42 ... N43 | 1.80 | 2.93 | −131.61 |
| | O13-H32 ... N47 | 1.85 | | |

TABLE 5-continued

Hydrogen bonds, relative optimized complex energy ($\Delta E_{relative}$), and Fi-SAFT predicted interaction energy (I.E.) between the different conformers of lignin and spermidine.

| Lignin-spermidine | H-bonding | Distance (Å) | $\Delta E_{relative}^{a}$, (kJ/mol) | I. E., (kJ/mol) |
|---|---|---|---|---|
| Conformer 3 | O23-H43 ... N53 | 1.81 | 24.16 | −95.29 |
| Conformer 4 | O23-H42 ... N52 | 1.83 | 30.41 | −138.36 |
| | O11-H31 ... N47 | 1.81 | | |
| Conformer 5 | O11-H31 ... N43 | 1.82 | 33.07 | −81.00 |
| | N47-H71 ... O13 | 2.26 | | |
| | N43-H53 ... O8 | 2.26 | | |
| Conformer 6 | O23-H42 ... N52 | 1.79 | 45.10 | −107.82 |
| | N47-H71 ... O11 | 2.19 | | |
| | N43-H53 ... O8 | 2.17 | | |
| Conformer 7 | O13-H32 ... N42 | 1.86 | 57.12 | −70.95 |
| Conformer 8 | O23-H42 ... N52 | 1.74 | 77.17 | −59.88 |

$^{a}\Delta E_{relative}$ (kJ/mol) = ($E_{conformer1} - E_{conformer\ (1\ to\ n)}$) × 2625.5

TABLE 6

Hydrogen bonds, relative optimized complex energy ($\Delta E_{relative}$), and Fi-SAFT predicted interaction energy (I.E.) between the different conformers of lignin and 1,5-diaminopentane.

| Lignin-1,5-diaminopentane | H-bonding | Distance (Å) | $\Delta E_{relative}^{a}$, (kJ/mol) | I. E., (kJ/mol) |
|---|---|---|---|---|
| Conformer 1 | O23-H43 ... N44 | 1.79 | 0.00 | −122.45 |
| | O13-H32 ... N50 | 1.85 | | |
| Conformer 2 | O11-H31 ... N44 | 1.87 | 26.89 | −106.28 |
| | O23-H43 ... N50 | 1.82 | | |
| Conformer 3 | O13-H32 ... N50 | 1.89 | 40.87 | −70.77 |
| Conformer 4 | O13-H32 ... N44 | 1.88 | 50.04 | −62.30 |
| Conformer 5 | O13-H32 ... N44 | 1.87 | 56.00 | −58.87 |
| Conformer 6 | O23-H43 ... N44 | 1.79 | 65.91 | −52.77 |
| Conformer 7 | N44-H52 ... O11 | 2.25 | 75.29 | −38.68 |
| Conformer 8 | — | — | 88.35 | −27.12 |
| Conformer 9 | N44-H51 ... O8 | 2.27 | 95.71 | −22.16 |

$^{a}\Delta E_{relative}$ (kJ/mol) = ($E_{conformer1} - E_{conformer\ (1\ to\ n)}$) × 2625.5

TABLE 7

Hydrogen bonds, relative optimized complex energy ($\Delta E_{relative}$), and Fi-SAFT predicted interaction energy (I.E.) between the different conformers of lignin and diethylenetriamine.

| Lignin-diethylene-triamine | H-bonding | Distance (Å) | $\Delta E_{relative}^{a}$, (kJ/mol) | I. E., (kJ/mol) |
|---|---|---|---|---|
| Conformer 1 | O11-H31 ... N50 | 1.86 | 0.00 | −114.94 |
| | O23-H43 ... N44 | 1.79 | | |
| Conformer 2 | O23-H43 ... N44 | 1.86 | 0.33 | −92.71 |
| | O13-H32 ... N50 | 1.87 | | |
| Conformer 3 | O13-H32 ... N44 | 1.84 | 0.73 | −49.82 |
| Conformer 4 | O23-H43 ... N50 | 1.82 | 0.80 | |
| | O11-H31 ... N44 | 1.88 | | |
| Conformer 5 | O23-H43 ... N50 | 1.78 | 5.75 | −45.78 |
| Conformer 6 | O11-H31 ... N50 | 1.84 | 6.70 | −60.67 |
| | N50-H63 ... O8 | 2.20 | | |
| Conformer 7 | N44-H52 ... O11 | 2.26 | 9.13 | −48.87 |
| Conformer 8 | — | — | 14.02 | −29.47 |
| Conformer 9 | O23-H43 ... N50 | 1.86 | 18.96 | −50.62 |
| Conformer 10 | O23-H43 ... N44 | 1.78 | 27.77 | −43.33 |
| Conformer 11 | N44-H51 ... O8 | 2.19 | 47.39 | −18.45 |

$^{a}\Delta E_{relative}$ (kJ/mol) = ($E_{conformer1} - E_{conformer\ (1\ to\ n)}$) × 2625.5

TABLE 8

Hydrogen bonds, relative optimized complex energy ($\Delta E_{relative}$), and Fi-SAFT predicted interaction energy (I.E.) between the different conformers of lignin and 1,3-diaminopropane.

| Lignin-1,3-diaminopropane | H-bonding | Distance (Å) | $\Delta E_{relative}^{a}$, (kJ/mol) | I. E., (kJ/mol) |
|---|---|---|---|---|
| Conformer 1 | O23-H43 . . . N48 | 1.79 | 0.00 | −90.26 |
|  | O13-H32 . . . N44 | 1.92 |  |  |
| Conformer 2 | O23-H43 . . . N48 | 1.86 | 4.09 | −83.02 |
|  | O13-H32 . . . N44 | 1.90 |  |  |
| Conformer 3 | O11-H31 . . . N44 | 1.77 | 5.91 | −74.70 |
| Conformer 4 | O11-H31 . . . N48 | 1.89 | 9.90 |  |
| Conformer 5 | O13-H32 . . . N48 | 1.88 | 13.82 | −65.86 |
| Conformer 6 | O23-H43 . . . N44 | 1.84 | 25.68 | −98.69 |
|  | O11-H31 . . . N48 | 1.92 |  |  |
| Conformer 7 | N48-H55 . . . O13 | 2.28 | 29.11 | −26.17 |
| Conformer 8 | O23-H43 . . . N48 | 1.74 | 39.50 | −57.90 |

$^{a}\Delta E_{relative}$ (kJ/mol) = ($E_{conformer1} - E_{conformer\ (1\ to\ n)}$) × 2625.5

TABLE 9

Hydrogen bonds, relative optimized complex energy ($\Delta E_{relative}$), and Fi-SAFT predicted interaction energy (I.E.) between the different conformers of lignin and 2,2-dimethyl-1,3-propanediamine (2,2-DM-1,3-PDA).

| Lignin-(2,2-dimethyl-1,3-propanediamine) | H-bonding | Distance (Å) | $\Delta E_{relative}^{a}$, (kJ/mol) | I. E., (kJ/mol) |
|---|---|---|---|---|
| Conformer 1 | O11-H31 . . . N44 | 1.90 | 0.00 | −60.58 |
| Conformer 2 | O23-H43 . . . N48 | 1.92 | 12.42 | −90.16 |
|  | N48-H55 . . . O20 | 2.28 |  |  |
|  | O11-H31 . . . N44 | 2.08 |  |  |
| Conformer 3 | O13-H32 . . . N48 | 1.88 | 24.16 | −56.03 |
| Conformer 4 | O13-H32 . . . N44 | 1.92 | 24.70 | −80.24 |
|  | O23-H43 . . . N48 | 1.96 |  |  |
| Conformer 5 | O13-H32 . . . N44 | 1.94 | 30.41 | −80.93 |
|  | O23-H43 . . . N48 | 1.91 |  |  |
| Conformer 6 | O13-H32 . . . N48 | 1.83 | 33.07 | −64.82 |
| Conformer 7 | O23-H43 . . . N48 | 1.80 | 45.10 | −56.20 |
| Conformer 8 | N48-H55 . . . O13 | 2.26 | 57.12 | −37.61 |
| Conformer 9 | N44-H61 . . . O8 | 2.23 | 77.17 | −20.48 |

$^{a}\Delta E_{relative}$ (kJ/mol) = ($E_{conformer1} - E_{conformer\ (1\ to\ n)}$) × 2625.5

TABLE 10

Hydrogen bonds, relative optimized complex energy ($\Delta E_{relative}$), and Fi-SAFT predicted interaction energy (I.E.) between the different conformers of lignin and 2-ethoxy ethanol.

| Lignin-2-ethoxy ethanol | H-bonding | Distance (Å) | $\Delta E_{relative}^{a}$, (kJ/mol) | I. E., (kJ/mol) |
|---|---|---|---|---|
| Conformer 1 | O11-H31 . . . O46 | 1.88 | 0.00 | −69.48 |
|  | O50-H59 . . . O20 | 2.01 |  |  |
| Conformer 2 | O23-H43 . . . O46 | 1.91 | 6.61 | −66.11 |
|  | O13-H32 . . . O57 | 2.01 |  |  |
| Conformer 3 | O11-H31 . . . O46 | 2.03 | 12.40 | −45.90 |
| Conformer 4 | O23-H43 . . . O57 | 1.79 | 12.47 | −38.10 |
|  | O57-H59 . . . O20 | 1.90 |  |  |
| Conformer 5 | O11-H31 . . . O46 | 1.86 | 15.49 | −51.66 |
| Conformer 6 | O57-H59 . . . O13 | 1.84 | 17.37 | −43.75 |
| Conformer 7 | O57-H59 . . . O8 | 1.91 | 20.64 | −42.46 |

$^{a}\Delta E_{relative}$ (kJ/mol) = ($E_{conformer1} - E_{conformer\ (1\ to\ n)}$) × 2625.5

TABLE 11

Hydrogen bonds, relative optimized complex energy ($\Delta E_{relative}$), and Fi-SAFT predicted interaction energy (I.E.) between the different conformers of lignin and benzyl alcohol.

| Lignin-benzyl alcohol | H-bonding | Distance (Å) | $\Delta E_{relative}^{a}$, (kJ/mol) | I. E., (kJ/mol) |
|---|---|---|---|---|
| Conformer 1 | O51-H59 . . . O13 | 1.87 | 0.00 | −65.90 |
| Conformer 2 | O51-H59 . . . O8 | 2.20 | 0.26 | −67.40 |
| Conformer 3 | O51-H59 . . . O20 | 2.18 | 10.51 | −50.42 |
| Conformer 4 | O51-H59 . . . O13 | 1.96 | 21.12 | −65.16 |
| Conformer 5 | O51-H59 . . . O1 | 2.11 | 24.19 | −59.60 |
| Conformer 6 | O11-H31 . . . O51 | 1.89 | 33.31 | −55.21 |

$^{a}\Delta E_{relative}$ (kJ/mol) = ($E_{conformer1} - E_{conformer\ (1\ to\ n)}$) × 2625.5

TABLE 12

Hydrogen bonds, relative optimized complex energy ($\Delta E_{relative}$), and Fi-SAFT predicted interaction energy (I.E.) between the different conformers of lignin and furfuryl alcohol.

| Lignin-furfuryl alcohol | H-bonding | Distance (Å) | $\Delta E_{relative}^{a}$, (kJ/mol) | I. E., (kJ/mol) |
|---|---|---|---|---|
| Conformer 1 | O50-H56 . . . O11 | 1.82 | 0.00 | −63.51 |
| Conformer 2 | O50-H56 . . . O13 | 1.90 | 9.03 | −64.35 |
| Conformer 3 | O50-H56 . . . O13 | 1.91 | 22.48 | −53.37 |
| Conformer 4 | O50-H56 . . . O13 | 1.90 | 23.63 | −59.64 |
| Conformer 5 | O50-H56 . . . O11 | 1.89 | 37.50 | −60.56 |
| Conformer 6 | O50-H56 . . . O11 | 1.97 | 40.48 | −66.95 |
| Conformer 7 | O23-H43 . . . O50 | 1.82 | 44.70 | −44.01 |
|  | O50-H56 . . . O20 | 1.95 |  |  |

$^{a}\Delta E_{relative}$ (kJ/mol) = ($E_{conformer1} - E_{conformer\ (1\ to\ n)}$) × 2625.5

TABLE 13

Hydrogen bonds, relative optimized complex energy ($\Delta E_{relative}$), and Fi-SAFT predicted interaction energy (I.E.) between the different conformers of lignin and isobutyl acetate.

| Lignin-isobutyl acetate | H-bonding | Distance (Å) | $\Delta E_{relative}^{a}$, (kJ/mol) | I. E., (kJ/mol) |
|---|---|---|---|---|
| Conformer 1 | O23-H43 . . . O46 | 1.92 | 0.00 | −56.61 |
| Conformer 2 | O11-H31 . . . O46 | 1.83 | 6.16 | −53.87 |
| Conformer 3 | O11-H31 . . . O46 | 1.83 | 6.16 | −53.87 |
| Conformer 4 | O13-H32 . . . O46 | 2.02 | 7.09 | −49.05 |
| Conformer 5 | O13-H32 . . . O46 | 2.02 | 7.09 | −49.05 |
| Conformer 6 | O11-H31 . . . O46 | 1.89 | 17.95 | −52.81 |

$^{a}\Delta E_{relative}$ (kJ/mol) = ($E_{conformer1} - E_{conformer\ (1\ to\ n)}$) × 2625.5

Figure 10:
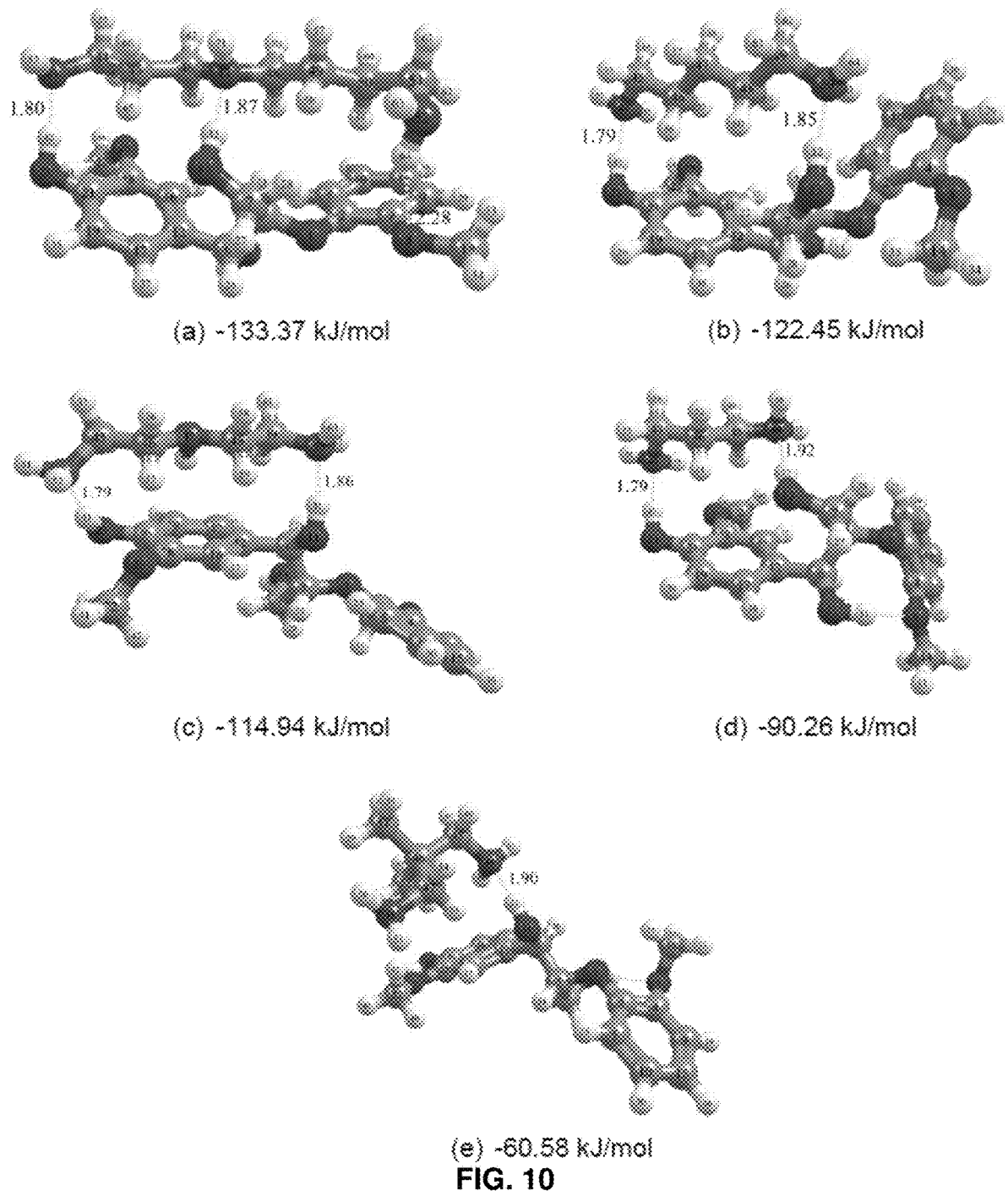
FIG. 10 Optimized geometries for lignin GGE-amines (a) spermidine, (b) 1,5-diaminopentane, (c) diethylenetriamine, (d) 1,3-diaminopropane, and (e) 2,2-dimethyl-1,3-propanediamine. The H-bonds are indicated by dotted lines, the bond lengths are in Angstrom (A) and given with corresponding atom numbers. The color scheme used for different atoms is C (gray), O (red), N (blue), and H (white), respectively.

2.5.1. Optimized Geometries and Interaction Energies of Lignin-Amines/Organic Solvents We first set out to determine the optimized geometries of lignin GGE dissolved in various molecular solvents and assess their interaction energies, which will bring insights into how strongly the solvents interact with the lignin through H-bonding and how that might impact lignin dissolution (FIGS. 10 and 21). From these figures, it appears that the amines (except 2,2-dimethyl-1,3-propanediamine) form stronger H-bonds O—H . . . N (1.79 Å-1.92 Å) with lignin than the non-amine organic solvents (2-ethoxy ethanol, furfuryl alcohol, isobutyl acetate, and benzyl alcohol) O—H . . . O (1.88 Å-2.02 Å), thereby resulting in higher interaction energies between amines and lignin. Moreover, amines form multiple hydrogen bonds with the lignin molecule. Thus, we speculated that intermolecular H-bonds between the amines and lignin might be a vital factor in promoting the higher solubility of lignin in these solvents. A comparison of the interaction energies of amines indicates that spermidine has the highest interaction energies with lignin, followed by 1,5-diaminopentane, diethylenetriamine, and 1,3-diaminopropane.

Figure 11:
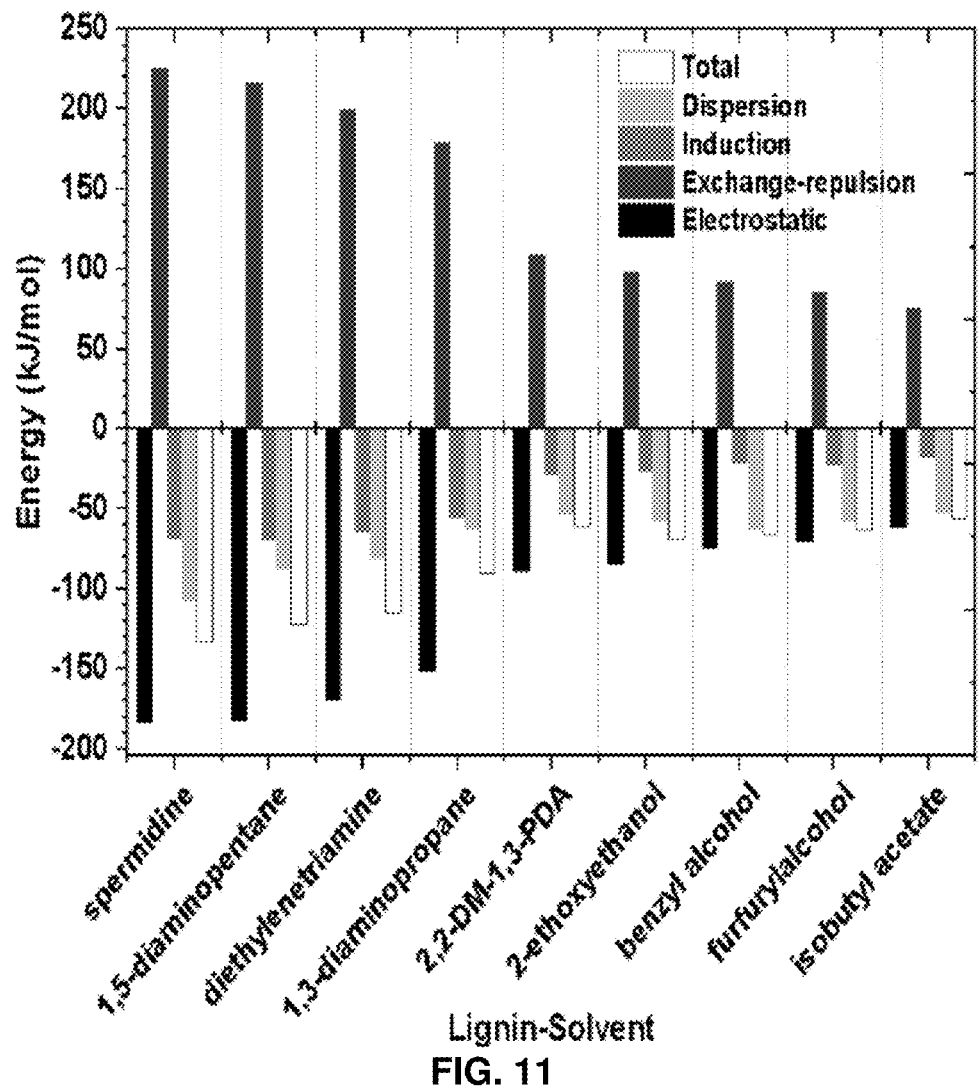
FIG. 11 Functional group intramolecular symmetry adapted perturbation theory (FI-SAPT) decomposition of the non-bonded interaction energies between lignin and molecular solvents.

On a fundamental level, the total interaction energy of a solvent with lignin is decomposed into four chemically meaningful contributors: electrostatic, exchange-repulsion, induction, and dispersion (see FIG. 11). The electrostatic energy corresponds to the classic electrostatic interaction between the promoted fragments as they are brought to their positions in the final complexes, the term exchange repulsion accounts for Pauli repulsion between closed-shell fragments and is perpetually positive. The induction term, sometimes referred to as the orbital interaction or the polarization energy, arises from the orbital relaxation and the orbital mixing between the fragments (charge transfer). Dispersion energy which represents the amount of energy required to promote the fragments from their equilibrium geometry to the structure they will take up in the combined molecule. The stronger the interaction energy (more negative magnitude) between lignin and molecular solvents, the higher the anticipated lignin dissolution capacity. Analysis of these four contributors illustrates that the electrostatic interaction is the dominating attractive component between lignin and the amine, while dispersion and induction energies play a minor role in stabilizing the lignin-amine complexes. In the case of non-amine organic solvent systems, dispersion interactions are almost equal to the electrostatic interactions. Also, the induction interactions are significant in lignin-amine complexes relative to those calculated for the non-amine organic solvent complexes. This higher induction energy in lignin-amine complexes indicates that a substantial charge transfer occurred between lignin and amines. In terms of magnitude, all of the energy components are greater in the lignin-amine complexes than the lignin-organic solvent complexes. The order of attractive interactions in lignin-amine complexes is electrostatic>dispersion>induction. Overall, the QC calculated interaction energies are in good agreement with the COSMO-RS predicted interactions and lignin solubility. The QC and COSMO-RS results can be used to suggest the solubility of lignin is lower in these types of organic solvents due to the weaker interactions.

2.5.2. Reduced Density Gradient (RDG) Analysis of Lignin-Amines/Organic Solvents RDG analysis was carried out to examine the strength of the non-covalent interactions (NCIs) between the lignin and amines/organic solvents. This method can be used to visualize the different interaction energy contributions, such as hydrogen bond, van der Waals, and steric repulsion. NCIs are assessed using the normalized and dimensionless reduced density gradient (equation (4))

$$RDG = \frac{1}{\left[2(3\pi^2)^{\frac{1}{3}}\right]} \frac{|\nabla \rho(r)|}{\rho(r)^{\frac{4}{3}}} \quad (4)$$

Regions where the RDG and electron densities are low representing the non-covalent interactions. Therefore, the isosurface of RDG at lower electron densities was used to visualize the position and nature of NCIs in 3D space. This is done by plotting the RDG vs sign of second Hessian eigenvalue ($\lambda_2$) multiplied with the electron density ($\rho(r)$) (sign($\lambda_2$)·$\rho(r)$) in a scatter plot.

Figure 12:
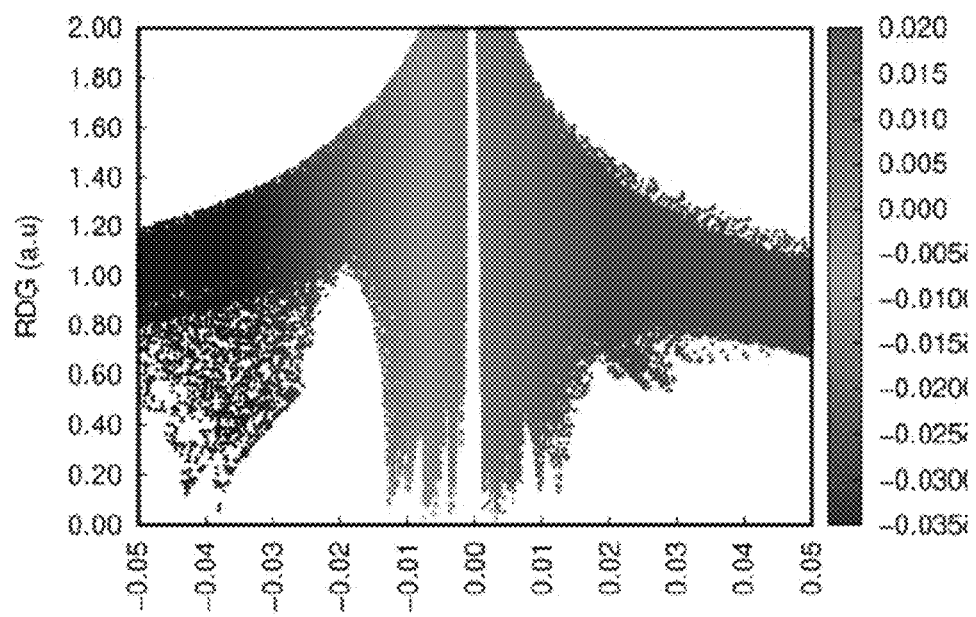
FIG. 12 RDG scatter and NCI plots (isovalue 0.5 a.u.) of (a) lignin-spermidine (RDG), (b) lignin-spermidine (NCI), (c) lignin-furfuryl alcohol (RDG), and (d) lignin-furfuryl alcohol (NCI). The RDG/NCI plots are colored on a blue-green-red scale according to values of sign($\lambda_2$)$\rho(r)$, ranging from −0.045 to 0.025. Blue indicates strong attractive interactions, green indicates the vdW interaction, and red indicated steric repulsions. The color scheme used for different atoms is C (cyan), O (red), N (blue), and H (white), respectively.
Figure 12:
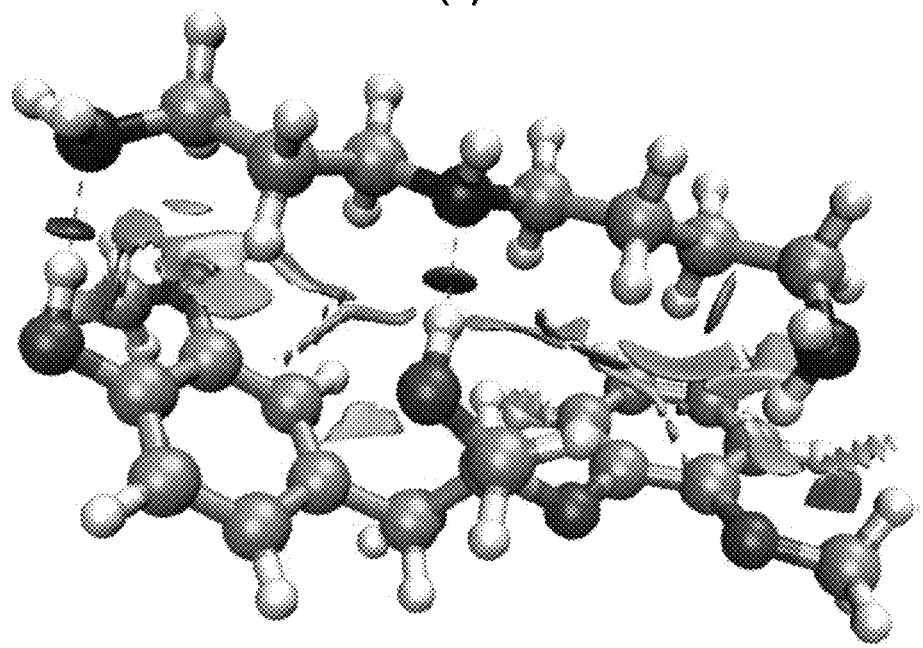
Figure 12:
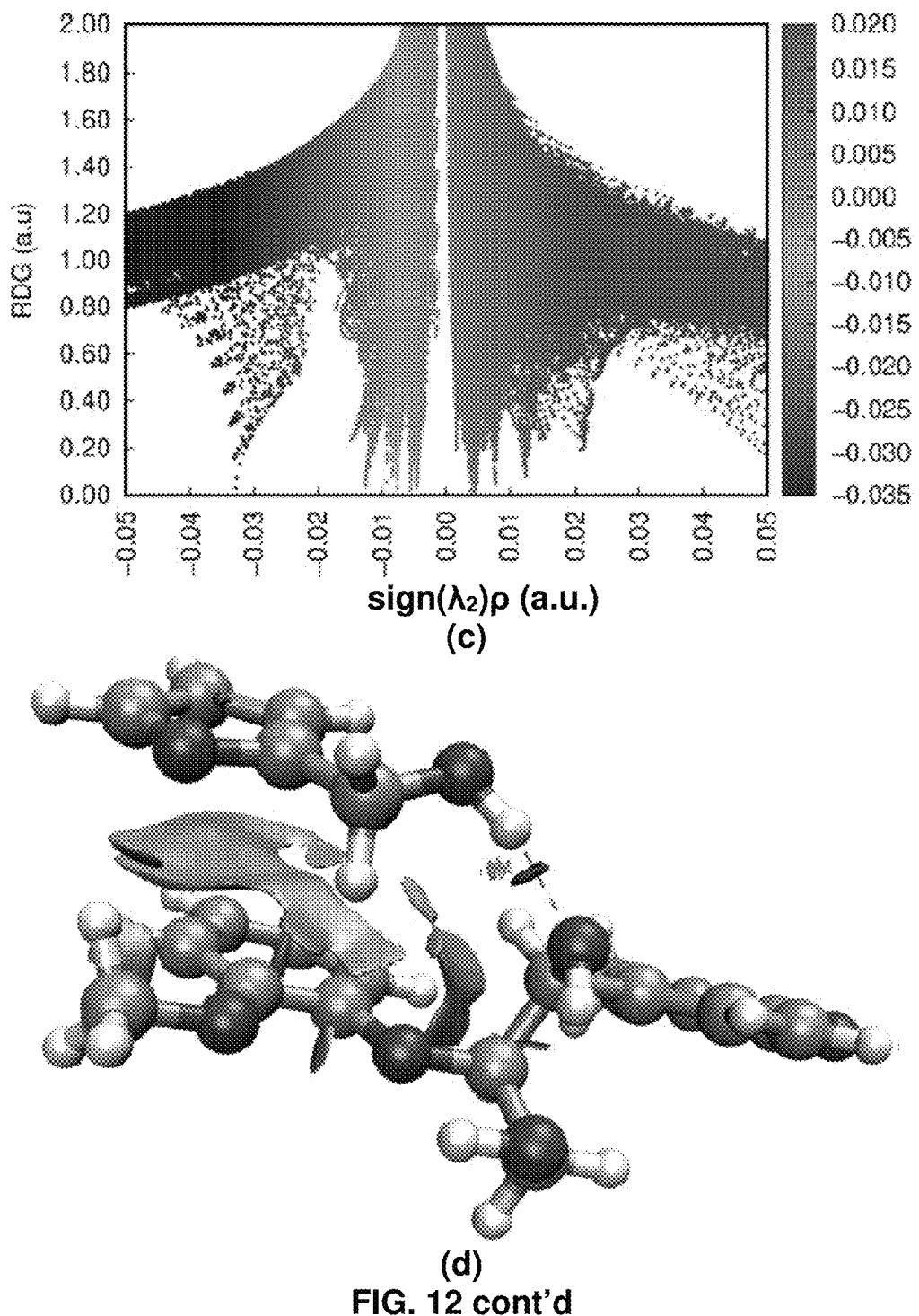

Two representative solvents, spermidine (amine) and furfuryl alcohol (one non-amine), were selected to explore this analysis in detail (FIG. 12 (Panels a and c)) and plots of the remaining solvents are provided in FIG. 22. Scanning across sign($\lambda_2$)·$\rho(r)$ from positive to negative values, there are several spikes in RDG scatter plot that correspond to the steric repulsion (red color), van der Waal (green color) interaction, and hydrogen bonding (blue color). In FIG. 12 (Panels b and d), the interactions are visualized, and colored surfaces correspond to the respective colors in the respective NCI scatter plots. Examination of the NCI plots show that the amine-based solvents have spikes in the negative region of sign($\lambda_2$)·$\rho(r)$ that are more negative (O—H . . . N: −0.032<sign($\lambda_2$)·$\rho(r)$<−0.044) than the non-amine organic solvents (O—H . . . O: sign($\lambda_2$)·$\rho(r)$>−0.03), which indicates that the strength of the H-bond interactions (blue region) are much stronger between lignin and amines. On the other hand, in the attractive region, multiple spikes are observed for lignin-amine interactions which are consistent with the geometrical analysis. Also, in the lignin-amine systems, the major steric repulsions (red color) occurred within the lignin molecule while it occurred between the lignin and solvent in the lignin-organic solvents, weakening their interaction and potentially explaining the lower lignin solubility observed in non-amine solvents (FIG. 13 (Panels b and d)).

2.5.3. QTAIM Analysis of Lignin-Amines/Organic Solvents

To gain deeper insights into the intermolecular interactions between lignin and amine or organic solvents, we conducted quantum theory of atom in molecule (QTAIM) analysis. QTAIM analysis is used to examine critical bonding topological characteristics, such as electron density $\rho(r)$, Laplacian energy density $\nabla^2\rho(r)$, energy density $H_{BCP}(r)$, and H-bonding energies ($E_{HB}$). The interatomic interactions are quantitatively represented by using signs of $\rho(r)>0$, $\nabla^2\rho(r)>0$, and $H_{BCP}(r)<0$ at bond critical points (BCPs) and classified as closed-shell interactions, which include the H-bonding and van der Waals interactions. The positive sign of $\rho(r)$ corresponds to the strength of the hydrogen bond, a positive sign of $\nabla^2\rho(r)$ represents the characteristic of hydrogen bonds (non-covalent type), and $H_{BCP}(r)$ corresponds to the nature of the hydrogen bonds (a positive sign corresponds to non-covalent and a negative sign corresponds to covalent). According to Koch and Popelier, the $\rho(r)$ and $\nabla^2\rho(r)$ at the BCP for hydrogen bond interactions must be in the range of 0.002-0.035 a.u. and 0.014-0.139 a.u., respectively.[48,49] As mentioned above, the $\rho(r)$ for the vdW region tends to be smaller (0.002-0.009 a.u.) than hydrogen bonding and steric repulsion.

Table 3 reports the $\rho(r)$, $\nabla^2\rho(r)$, and $H_{BCP}(r)$ of hydrogen bond critical points for the lignin-amine (O—H . . . N) and lignin-organic solvent (O—H . . . O) systems. For the lignin-amine system, the values of p(r) are in the range of 0.036-0.044 a.u., which is higher than the Koch and Popelier proposed range for electron densities for the hydrogen bond. Whereas, in the case of lignin-organic solvents, the values of $\rho(r)$ and $\nabla^2\rho(r)$ lies within the Koch and Popelier proposed ranges (0.002-0.035 a.u. and 0.014-0.139 a.u.). From these electron densities, the O—H . . . N bond between lignin and the amine solvent is predicted to be stronger than the O—H . . . O bond between lignin and non-amine solvents. The Laplacian electron densities at the BCP show positive values for both lignin-amines/organic solvent systems, implying that the characteristics of H-bonding interactions are non-covalent. Further examining energy densities ($H_{BCP}(r)$), they are negative for O—H . . . N and positive for O—H . . . O at the BCP, indicating the amine-lignin interactions are more covalent in nature while the non-amine solvents have more non-covalent or weak interactions.

These calculations (ρ(r), ∇²ρ(r), and H$_{BCP}$(r))) help in explain why the organic solvents exhibit lower interactions with lignin.

TABLE 3

Topological electron density (a.u.) properties of H-bonded (H . . . N & H . . . O) complexes at bond critical points (BCPs) for the interaction of lignin-amine/organic solvent systems and H-bond energies (E$_{HB}$) calculated at the B3LYP-GD3/6-311 + G(d, p) Level of Theory. Atom notations are given in FIGS. 10 and 21.

| Amine/Organic Solvent | H-Bond | Distance (Å) | ρ(r) | ∇² ρ(r) | H$_{BCP}$(r) | E$_{HB}$ (kJ/mol) |
|---|---|---|---|---|---|---|
| Spermidine | O23-H42 . . . N43 | 1.80 | 0.0436 | 0.0957 | −0.0059 | −46.84 |
|  | O13-H32 . . . N47 | 1.87 | 0.0382 | 0.093 | −0.0032 | −38.84 |
|  | N52-H64 . . . O8 | 2.28 | 0.0128 | 0.0435 | 0.0013 | −10.76 |
| 1,5-diaminopentane | O23-H43 . . . N44 | 1.79 | 0.045 | 0.0957 | −0.0067 | −48.94 |
|  | O13-H32 . . . N50 | 1.85 | 0.0393 | 0.0947 | −0.0037 | −40.68 |
|  | N44-H52 . . . O20 | 2.38 | 0.0124 | 0.0424 | 0.0011 | −10.89 |
| Diethylenetriamine | O11-H31 . . . N50 | 1.86 | 0.038 | 0.095 | −0.0032 | −39.49 |
|  | O23-H43 . . . N44 | 1.79 | 0.045 | 0.099 | −0.0062 | −48.94 |
| 1,3-diaminopropane | O23-H43 . . . N48 | 1.79 | 0.0449 | 0.0994 | −0.0065 | −49.73 |
|  | O13-H32 . . . N44 | 1.92 | 0.0334 | 0.0898 | −0.0011 | −32.28 |
|  | N44-H55 . . . O20 | 2.37 | 0.0124 | 0.0441 | 0.0014 | −10.89 |
| 2,2-dimethyl-1,3-propaneamine | O11-H31 . . . N44 | 1.90 | 0.0347 | 0.0895 | −0.0018 | −34.12 |
| 2-ethoxy ethanol | O11-H31 . . . O46 | 1.88 | 0.030 | 0.101 | 0.0008 | −31.10 |
|  | O57-H59 . . . O20 | 2.01 | 0.020 | 0.078 | 0.0023 | −19.42 |
| Benzyl alcohol | O51-H59 . . . O13 | 1.87 | 0.0306 | 0.1049 | 0.0008 | −32.28 |
| Furfuryl alcohol | O50-H56 . . . O11 | 1.82 | 0.033 | 0.1184 | 0.0006 | −37.13 |
| Isobutyl acetate | O23-H43 . . . O46 | 1.92 | 0.0247 | 0.0953 | 0.0023 | −25.19 |

$H_{BCP}(r) = G_{BCP}(r) + V_{BCP}(r);$ $E_{HB}(kJ/mol) = \frac{1}{2}V(r) \times 2624.25;$ G$_{BCP}$(r) is the Lagrangian kinetic energy density; V$_{BCP}$(r) is the potential energy density.

Additionally, hydrogen bonding energies (E$_{HB}$) are also calculated using the potential energy densities V$_{BCP}$(r). The hydrogen bonding energy of O—H . . . N (lignin-amine) is much stronger than the O—H . . . O bond energy. It is worthwhile to mention that 2,2-dimethyl-1,3-propanediamine showed similar electronic properties (ρ(r), ∇²ρ(r), and E$_{HB}$) as the organic solvents, which is consistent with the low solubility of lignin observed with this solvent. In addition to the aforementioned discussions, there is a strong correlation between Hessian second eigenvalue (λ$_2$) and E$_{HB}$ values (FIG. 23). The lower the λ$_2$ value, the stronger the hydrogen bonding energy. Overall, the electronic properties clearly indicate that the amine solvents are highly effective solvents for the lignin removal and have much stronger hydrogen bonding energies than the organic solvents.

2.5.4. Natural Bonding Orbital (NBO) Analysis

NBO analysis was performed to understand the strength of the electron donor-acceptor orbital interactions between lignin and the solvents. The electron donor-acceptor bond energies are reported in Table 3. The larger the electron donor-acceptor bond energy (E$^{(2)}$*), the stronger the interaction. In the lignin-solvent systems, the lone pair (LP) electrons of the amine (nitrogen atom) or organic solvent (oxygen atom) interact with the anti-bonding orbital (BD* or σ*) of the lignin dimer (hydroxyl proton). These electron donor-acceptor orbitals are responsible for the formation of strong H-bonds between them. In the complex systems, the amine/organic solvent moieties act as an electron donor and lignin moiety is the electron acceptor. Examining the lignin-organic solvents, 2-ethoxyethanol and benzyl alcohol show the strongest electron donor-acceptor (LP(O)→σ*(O11-H31)) orbital energies. In the case of lignin-amines complexes, the electron donor-acceptor (LP(N)→σ*(O—H)) orbital energies are two to three-time stronger than the organic solvent systems. These results are consistent with the QTAIM and COSMO-RS predictions.

In addition, the π-π and CH-π stacking interactions in the lignin-solvent complexes were also examined, where applicable. π-π interactions are observed in the benzyl alcohol and furfuryl alcohol lignin complexes whereas CH-π stacking interactions were observed in the isobutyl acetate, 2-ethoxyethanol, and amine-lignin complexes. Overall, the strength of CH-π interactions was predicted to be relatively stronger than π-π. However, compared to LP (O)→σ* orbital energies, the CH-n stacking interactions are not significant and therefore less relevant to lignin dissolution. Overall, the QC calculations indicate that hydrogen bonding interactions are playing a vital role in the dissolution of lignin. Organic solvents also exhibit significant hydrogen bonding energies, but due to the strong steric repulsions and weaker polarity, the net result is lower lignin solubility.

TABLE 3

The electron donor and acceptor orbitals with their corresponding second-order interaction energies $E^{(2)}*$ (NBO analysis) of lignin-amine/organic solvent systems. Atom notations are given in FIGS. 10 and 21.

| Amine Organic Solvent | H-bond interaction | | | π-stacking interaction | | |
|---|---|---|---|---|---|---|
| | Donor | Acceptor | $E^{(2)}*$ (kJ/mol) | Donor | Acceptor | $E^{(2)}*$ (kJ/mol) |
| Spermidine | LP (1) N43 | σ* O23-H42 | 101.87 | π C18-C21 | σ* C45-H65 | 1.46 |
| | LP (1) N47 | σ* O13-H32 | 71.39 | π C2-C5 | σ* C50-H59 | 1.42 |
| | LP (2) O8 | σ* N52-H64 | 5.31 | | | |
| 1,5-diaminopentane | LP (1) N44 | σ* O23-H43 | 107.73 | π C18-C21 | σ* C46-H56 | 0.71 |
| | LP (1) N50 | σ* O13-H32 | 86.32 | | | |
| Diethylenetriamine | LP (1) N44 | σ* O23-H43 | 101.96 | π C12-C17 | σ* C49-H60 | 1.30 |
| | LP (1) N50 | σ* O11-H31 | 80.34 | π C19-C21 | σ* C47-H57 | 2.38 |
| 1,3-diaminopropane | LP (1) N48 | σ* O23-H43 | 102.92 | π C19-C21 | σ* C46-H51 | 1.09 |
| | LP (1) N44 | σ* O13-H32 | 66.92 | π U16-C18 | σ* C45-H50 | 0.59 |
| 2,2-dimethyl-1,3-propaneamine | LP (1) N44 | σ* O11-H31 | 69.92 | π C16-C18 | σ* C52-H64 | 2.51 |
| | LP (1) N48 | σ* C22-H42 | 8.53 | | | |
| 2-ethoxy ethanol | LP (1) O46 | σ* O11-H31 | 13.68 | π C12-C17 | σ* C45-H49 | 0.88 |
| | LP (2) O46 | σ* O11-H31 | 30.28 | | | |
| | LP (1) O20 | σ* O57-H59 | 8.11 | | | |
| | LP (1) O20 | σ* O57-H59 | 10.66 | | | |
| Benzyl alcohol | LP (1) O13 | σ* O51-H59 | 8.28 | π C4-C9 | σ* C47-C48 | 1.17 |
| | LP (2) O13 | σ* O51-H59 | 41.23 | π C47-C48 | σ* C14-H35 | 1.21 |
| Furfuryl alcohol | LP (1) O11 | σ* O50-H56 | 13.01 | π C4-C9 | σ* C45-C46 | 1.13 |
| | LP (2) O11 | σ* O50-H56 | 39.02 | π C47-C48 | σ* C4-C9 | 1.17 |
| Isobutyl acetate | LP (1) O46 | σ* O23-H43 | 17.90 | π C16-C18 | σ* C50-H60 | 1.42 |
| | LP (2) O46 | σ* O23-H43 | 11.33 | | | |

3. Materials and Methods

3.1. Materials

In this study, Sorghum (*Sorghum bicolor*) biomass was obtained from Idaho National Labs (Idaho Falls, Idaho, USA) and used as a raw material. The acquired biomass samples were milled (Thomas-Wiley Model 4, Swedesboro, NJ) and sieved to attain a homogeneous particle size of 2 mm, and finally oven-dried (40° C., 24 h). The resulting biomass was then placed in an airtight plastic bag and stored in a cool dry place until further use. The following solvents were purchased from Sigma Aldrich (St. Louis, MO) and used as received: 2,2-dimethyl-1,3-propanediamine (purity: 99%), ethylenediamine (≥99), spermidine (≥99%), spermine (≥99%), 1,2-diaminopropane (99%), 1,3-diaminopropane (≥99%), 1,4-diaminobutane (99%), 1,5-diaminopentane (95%), diethylenetriamine (99%), pentylamine (99%). 2-ethoxyethanol (≥99%), 2-pyrrolidone (≥99%), trimethyl phosphate (97%), furfuryl alcohol (98%), guaiacol (≥98%), benzyl alcohol (99%), isobutyl acetate (99%), aniline, (≥99.5%), furfural (99%), dipropylene glycol (99%), citric acid (ACS reagent≥99.5%), sodium citrate tribasic dihydrate (ACS reagent, ≥99.0%) and sodium azide. Sulfuric acid (72% and 95-98%) was purchased from VWR), and sugar standards glucose (≥99.5%), xylose (≥99%), and arabinose (≥98%) were procured from Sigma-Aldrich for high-performance liquid chromatography (HPLC) analysis. Commercial cellulase (Cellic® CTec3) and hemicellulase (Cellic® HTec3) mixtures were provided by Novozymes, North America (Franklinton, NC).

3.2. Pretreatment of Sorghum Biomass

The pretreatment of biomass sorghum was carried out using the conventional method that involves early separation (or washing) to remove the solvent after pretreatment. In a typical experiment, 1 g of the biomass was mixed with the 4 g of solvent and loaded into an ace pressure tube (50 mL, Ace Glass Inc., Vineland, NJ) and mixed well prior to the experiments. The pretreatment experiments were performed at 140° C. for 3 h of reaction time at a solid loading of 20 wt %. Post pretreatment, 25 mL of ethanol was added to the slurry before being transferred to a 50 mL Falcon tube and centrifuged at 4500 rpm to separate solids from liquid. The recovered solid was further washed with a mixture of ethanol and water (1:1) to remove any residual organic solvents. Finally, the recovered solid fractions were lyophilized before enzymatic hydrolysis (EH) and compositional analysis (CA). All the experiments were performed in duplicate and the average values are reported here. The solid recovery (% SR) after pretreatment was calculated based on the following equation.

$$\% \text{ Solid Recovery (\% } SR) = \frac{\text{Weight of biomass recovered after pretreatment}}{\text{Weight of biomass used for pretreatment}} \times 100 \quad (5)$$

3.3. Enzymatic Hydrolysis

The enzymatic saccharification of pretreated and untreated biomass was carried out using commercially available enzymes, Cellic® Ctec3 and Htec3 (9:1 v/v) from Novozymes, at 50° C. in a rotary incubator (Enviro-Genie, Scientific Industries, Inc.). All reactions were performed at 5 wt % biomass loading in a 15 mL centrifuge tube (using 0.25 g of the pretreated or untreated biomass). The pH of the mixture was adjusted to 5 with 50 mM sodium citrate buffer supplemented with 0.02 wt % sodium azide to prevent microbial contamination. The total reaction volume included a total protein content of 10 mg per g biomass. The amount of sugars released was analyzed on an Agilent HPLC 1260 infinity system (Santa Clara, California, United States) equipped with a Bio-Rad Aminex HPX-87H column (300× 7.8 mm$^2$) and a Refractive Index detector. An aqueous solution of sulfuric acid (4 mM) was used as the eluent (0.6 mL min$^{-1}$, column temperature 60° C.). All enzymatic saccharification was conducted in duplicate. The sugar yield was calculated as an overall process yield using the formula below (equation 6), which accounts for sugars/oligosaccharides lost during pretreatment/washing.

$$\% \text{ Sugar Yield (Process)} = \qquad (6)$$
$$\% \ SR \times \frac{\text{Weight sugars released after hydrolysis}}{\text{Weight of sugars in the original biomass}} \times 100$$

3.4. Compositional Analysis

The compositional analysis of pretreated and untreated biomass sorghum was performed to determine the glucan, xylan, lignin and ash content following the two-step acid hydrolysis procedure previously described by NREL.[50] In summary, 300 mg of the dry extractive-free biomass was exposed to 3 mL of 72% w/w $H_2SO_4$ and incubated at 30° C. for 1 hr. Subsequently, the mixture was taken through secondary hydrolysis at 4% w/w $H_2SO_4$ at 121° C. for 1 hr. After the two-step acid hydrolysis, the hydrolysates were filtered using medium porosity filtering crucibles. The filtrates were spectrophotometrically analyzed for the acid-insoluble lignin (ASL) (NanoDrop 2000, Thermo Fisher Scientific, Waltham, MA) using the absorbance at 240 nm. Additionally, monomeric sugars (glucose and xylose) were determined by HPLC using an Agilent 1200 series instrument equipped with a refractive index detector and Bio-Rad Aminex HPX-87H column, coupled with a guard column assembly. Product separation was obtained at 60° C. with 4 mM $H_2SO_4$ as a mobile phase at a flow rate of 0.6 mL/min. Finally, the Klason lignin (acid-insoluble lignin—ASL) was determined gravimetrically by subtracting the weight of the oven-dried residual solids (105° C.) and the ash content (575° C.). All compositional analyses were conducted in duplicate. The amount of lignin removed can be calculated using the formula below (equation 7). Note: % Lignin=% AIL+% ASL.

$$\% \text{ Lignin Removal} = 100 - \% \ SR \times \frac{\% \ \text{Lignin}_{after \ biomass \ pretreatment}}{\% \ \text{Lignin}_{original \ biomass}} \qquad (7)$$

3.5. Structural Characterization (P-XRD Analyses)

The cellulose allomorph and crystallinity index was measured using in the 2θ range from 5 to 60° and an exposure time of 300 s with a voltage of 40 kV and current of 20 mA using Co-Kα radiation (λ=1.7891 nm). Note: The diffraction angle was converted to the analogous Cu-Kα (λ=1.5418 nm) for peak identification and analysis using previously assigned spectra. The peak deconvolution of the resulting diffractogram was performed using software PeakFit (Sea-Solve Software Inc.). Gaussian/Lorentzian functions were applied in curve fitting analysis and iterations were repeated until the maximum F number was obtained. In all cases, the F number was >10,000, which corresponds to a $R^2$ value>0.99. Estimation of the content of cellulose I, cellulose III, and amorphous cellulose in the cellulosic samples was established by using the peak areas of cellulose I, cellulose III, and amorphous cellulose, respectively. According to previously defined diffractogram, the Bragg angles of peak (110), (1͞10), (020), and (004) belonging to cellulose I are ~[14.8°, 16.3°, 22.3°, and 34.5°], respectively. The Bragg angles of peak (110) and (020) belonging to cellulose III are 11.30 and 20.0°, respectively. The Bragg angle of the amorphous peak is around 19.5-20.5°. The crystallinity index was also calculated according to the method of Segal et. al., where the ratio of the height of the 002 peak ($I_{002}$) and the height of the minimum ($I_{AM}$) between the 002 and the 101 peaks.

3.6. Computational Details

3.6.1 COSMO-RS Calculations

The COSMO-RS calculations were carried out to develop the lignin dissolution model in the molecular solvents. First, the structures of cellulose, lignin, and molecular solvents (see Scheme 1 and 2) are drawn in the Avogadro freeware software.[51] Initially, the structures of all the investigated molecules were optimized by using Gaussian09 package at B3LYP (Becke 3-parameter hybrid functional combined with the Lee-Yang-Parr correlation) theory and 6-311+G(d, p) basis set. To confirm the energy minima of the optimized structure and verify the presence of any imaginary frequency, frequency calculations have been performed at the same level of theory and no imaginary frequencies were present after optimization.

After a successful geometry optimization step, further, the COSMO file was generated using the BVP86/TZVP/DGA1 level of theory. [40,52,53] The ideal screening charges on the molecular surface were computed using the same level of theory i.e., BVP86 through the "scrf=COSMORS" keyword. [54,55] The generated COSMO files were then used as an input in the COSMOtherm (version 19.0.1, COSMO-logic, Leverkusen, Germany) package. [56,57] BP_TZVP_19 parametrization was used to predict the sigma potentials, viscosity, excess enthalpy, and logarithmic activity coefficients of the isolated and mixture of molecular systems. In COSMO-RS calculations, the molar fraction of lignin was set as 0.2, whereas the molar fraction of solvents was set to 0.8 to mimic the experimental pretreatment setup.

The excess enthalpy of a binary mixture can be predicted by using the following expression (equation 8):[53]

$$H_M^E = \Sigma x_i H_i^E = \Sigma x_i [H_{(i,mixture)} - H_{(i,pure)}] \qquad (8)$$

where, $H_M^E$ is the excess enthalpy of solute in the mixture and defined as the enthalpy difference between component i in the mixture and in the pure state. On the other hand, excess enthalpy of a mixture is an algebraic sum of the three contributors (equation 9) such as electrostatic misfit, hydrogen bonding, and van der Waals interactions.

$$H_M^E = H_M^E(\text{misfit}) + H_M^E(H\text{-bond}) + H_M^E(vdW) \qquad (9)$$

The activity coefficient of component i is associated with the chemical potential pi and expressed as [58] (equation 10):

$$\ln(\gamma_i) = \left(\frac{\mu_i - \mu_i^0}{RT}\right) \qquad (10)$$

where $\mu_i^0$ is the chemical potential of the pure component i, R is the real gas constant and T is the absolute temperature. The details of COSMO-RS calculation in predicting the sigma potential, excess enthalpies, and activity coefficients are provided in the COSMOtherm's user manual. 57

3.6.2. Quantum Chemical Calculations and Quantum Theory of Atom in Molecular (QTAIM) Analysis In addition to COSMO-RS calculations, the quantum chemical (QC) calculations were performed to understand the mechanistic behavior of lignin dissolution in the investigated molecular solvents. For QC simulations, the complex structures of lignin and molecular solvent are combined and drawn using Avogadro freeware software.[51] The geometries of the complex molecular systems were fully optimized at hybrid B3LYP/6-311+G(d,p) function corrected for dispersion interaction using Grimme's dispersion damping (GD3) empirical term.[59] It is known that the combination of B3LYP level of theory and 6-311+G(d,p) basis set is an excellent compromise between the computational cost and accuracy of the computational results.[31,60] All the optimized geometries were obtained without the presence of any imaginary frequencies.

From QC calculations, the interaction energy ($\Delta E_{total}$) is calculated by following the equation 11.[38,61]

$$\text{I.E. (kJ/mol)} = E_{complex} - \Sigma(E_{isolated\ molecules}) \quad (11)$$

where, $E_{complex}$ is the total energy of the complex system (i.e., lignin-solvent) in kJ/mol. $E_{isolated}$ molecules are the individual energies of the lignin or molecular solvent in kJ/mol. Further, SAPT (symmetry-adapted perturbation theory) calculations were performed to study the decomposition of total interaction energies into more meaningful components using the PSI4 program.[57,58]

$$\Delta E_{total}\text{(kJ/mol)} = \Delta E_{elec} + \Delta E_{exch} + \Delta E_{ind} + \Delta E_{disp} \quad (12)$$

$\Delta E_{elec}$, $\Delta E_{exch}$, $\Delta E_{ind}$, and $\Delta E_{disp}$ terms corresponding to the classic electrostatic, exchange-repulsion, induction, and dispersion interactions.

NBO analysis was employed to understand the strength of the electron donor-acceptor interactions involved in the system. The electron donor i-j acceptor delocalized stabilization energies ($E^{(2)*}$) were estimated from the second-order perturbation approach and are expressed in the equation 13 below.[62,63]

$$E^{(2)*} = \Delta E_{ij} = q_i \frac{F(i,j)^2}{\varepsilon_j - \varepsilon_i} \quad (13)$$

where $\varepsilon_i$ and $\varepsilon_j$ are the diagonal elements. $q_i$ is the donor orbital occupancy and $F(i,j)$ is the off-diagonal Fock matrix. The larger value of the $E^{(2)*}$, the more electron tends to transfer from donor to the acceptor.

In addition to the NBO analysis, QTAIM[64] analysis at the bond critical point (BCP) was performed to understand the strength (electron density, $\rho(r)$), characterization (Laplacian energy density ($\nabla^2 \rho(r)$), and nature (energy density $H(r)$) of the H-bond presented in lignin-molecular solvent systems using AllAIM (version 19.10.12) software.[65] The H-bond energy ($E_{HB}$) was calculated using Espinosa's equation: $E_{HB} = 1/2 \times V_{BCP}(r)$, in which $V_{BCP}(r)$ is the potential energy density at the BCP of the measured H-bond.[66] Further, to examine the nature of intermolecular interactions in the complex systems, reduced density gradient non-covalent interactions (RDG-NCI) were analyzed using Multiwfn[67] and VMD[68] packages.

3.6.3. Calculation of Solubility Parameters

The solubility parameter, defined as the square root of the cohesive energy density, is one of the key parameters that measure the polarity and quantify the 'like-dissolves-like' principle.[26] The solubility parameters of the molecular solvents under study were calculated by COSMOquick program.[69] The detailed calculation procedure of HSP using COSMOquick is reported elsewhere.[70,71] Based on the cohesive energy density assumptions, Hansen has broken the total solubility parameters ($\delta_t$) into the three contributors such as polar ($\delta_p$), hydrogen-bonded ($\delta_h$), and dispersion ($\delta_d$) forces.[26]

$$\delta_t = \sqrt{(\delta_p^2 + \delta_h^2 + \delta_d^2)} \quad (14)$$

In addition to $\delta_t$, Hansen also proposed a parameter called relative energy difference (RED) that correlates the interaction between a solute and a solvent. The RED is defined as the ratio between the radius of interaction ($R_a$) to the 3D sphere radius of the solute ($R_0$) as shown in the below equations (15 and 16).[26,34,72,73]

$$R_a = \sqrt{4(\delta_p^{salute} - \delta_p^{solvent})^2 + (\delta_h^{salute} - \delta_h^{solvent})^2 + (\delta_d^{salute} - \delta_d^{solvent})^2} \quad (15)$$

$$RED = \frac{R_a}{R_0} \quad (16)$$

If the RED<1, then the affinity of the solvent towards the solute is said to be higher. While If the RED>1, the affinity between the solvent and solute is lower.

4. Conclusions

The current work demonstrates an effective framework for (1) discovering and predicting high performing solvents for the dissolution of lignin and (2) understanding the mechanistic factors that control the lignin dissolution capacity of a solvent. This framework relies on multiscale simulation approaches to develop a predictive model to identify potential solvents for lignocellulosic biomass pretreatment, which are then experimentally verified. To initiate the development of this framework, several molecular solvents were screened using HSP and COSMO-RS models and amines were predicted to be effective solvents. Next, amines with different chemical functionalities were experimentally tested and shown to promote higher lignin removal and fermentable sugar yields than several non-amine solvents. The solvents 1,5-diaminopentane and 1,2-diaminopropane were found to be the most effective at biomass pretreatment, extracting>82% of lignin from biomass and enabling>88% yields of fermentable sugars. COSMO-RS was then used to develop a predictive model for lignin removal based on the several influential quantities: $H^E$, $\ln(\gamma)$, $\eta$, and $pK_a$. Comparison of the predictive model and experimental results shows that they are in excellent agreement, with a deviation of less than 10%.

Once effective lignin solvents were identified, QC calculations and QTAIM analysis were employed to understand the mechanism that drive the lignin solvent interactions and determine why the amines are more effective lignin extraction solvents than the other non-amine solvents examined in this study. QC and QTAIM analysis indicate that amines that form multiple strong H-bond interactions with lignin are able to extract high amounts of lignin from biomass. The use of computational platforms to both develop predictive models to identify effective pretreatment solvents and to then gain deeper insights into the mechanism of lignin dissolution by these solvents will lead to the rapid expansion of the list of solvents that can be used for efficient lignocellulose pretreatment and deconstruction. There are numerous considerations that must be made to effectively integrate a pretreatment technology into a biorefinery, including effectiveness on a broad range of feedstocks, fractionation of lignocellulose components, solvent cost, solvent recycling, generation of biomass-derived enzyme and microbe inhibitors, etc., and an expansive list of pretreatment solvents identified though the predictive framework established in this study will provide researchers and industry more options to consider in the development of highly efficient, low-cost lignocellulose conversion technologies.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method to deconstruct a biomass, the method comprising: (a) introducing a solvent comprising a polyamine to a biomass to dissolve at least part of solid biomass in the solvent, wherein the polyamine is a Brønsted or Lewis base, and/or the polyamine is a hydrogen bond donor and/or acceptor; wherein the polyamine has the chemical structure:

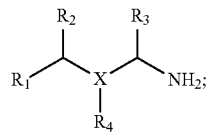

wherein X is C or N; and $R_1$, $R_2$, $R_3$, and $R_4$, are each independently —H, —$NH_2$, alkyl, alkenyl, alkynyl, aryl, alkyl amine, alkenyl amine, alkynyl amine, or aryl amine.

2. The method of claim 1, further comprising separating the polyamine from the solubilized biomass mixture by distillation.

3. The method of claim 1, wherein the polyamine is diamine, triamine, 1,5-diaminopentane, 1,4-diaminobutane, 1,3-diaminopropane, 1,2-diaminoethane, 1,2-diaminopropane, and 1,4-diaminobutane, ethylenediamine (ethane-1,2-diamine), diethylenetriamine, 1,3-diaminopropane (trimethylenediamine), 1,4-diaminobutane (putrescine), 1,5-diaminopentane (cadaverine), 1,2-diaminopropane, spermine (N1,N1'-(butane-1,4-diyl)bis(propane-1,3-diamine)), spermidine (N1-(3-aminopropyl)butane-1,4-diamine), 2,2-dimethyl-1,3-propanediamine, diethylenetriamine, spermine, or a mixture thereof.

4. The method of claim 1 wherein the solvent has a viscosity having a value equal to or less than about 50 cP at a temperature of about 90° C.

5. The method of claim 1 wherein the solvent has a boiling point having a value equal to or less than about 200° C.

* * * * *